United States Patent
MacKay et al.

(10) Patent No.: US 9,545,086 B2
(45) Date of Patent: Jan. 17, 2017

(54) BAFF, INHIBITORS THEREOF AND THEIR USE IN THE MODULATION OF B-CELL RESPONSE AND TREATMENT OF AUTOIMMUNE DISORDERS

(75) Inventors: Fabienne MacKay, Vaucluse (AU); Susan Kalled, Concord, MA (US)

(73) Assignee: Biogen MA Inc., Cambridge, MA (US)

( * ) Notice: Subject to any disclaimer, the term of this patent is extended or adjusted under 35 U.S.C. 154(b) by 1981 days.

(21) Appl. No.: 12/061,398

(22) Filed: Apr. 2, 2008

(65) Prior Publication Data
US 2009/0110676 A1    Apr. 30, 2009

Related U.S. Application Data

(60) Division of application No. 11/065,669, filed on Feb. 24, 2005, now abandoned, which is a continuation of application No. 10/045,574, filed on Nov. 7, 2001, now abandoned.

(51) Int. Cl.
| | |
|---|---|
| A61K 38/00 | (2006.01) |
| A01K 67/027 | (2006.01) |
| C07K 14/705 | (2006.01) |
| C07K 16/28 | (2006.01) |
| C12N 15/85 | (2006.01) |
| A61K 39/00 | (2006.01) |

(52) U.S. Cl.
CPC ....... *A01K 67/0275* (2013.01); *A01K 67/0278* (2013.01); *C07K 14/70575* (2013.01); *C07K 16/2875* (2013.01); *C07K 16/2878* (2013.01); *C12N 15/8509* (2013.01); *A01K 2207/15* (2013.01); *A01K 2217/00* (2013.01); *A01K 2217/05* (2013.01); *A01K 2227/105* (2013.01); *A01K 2267/03* (2013.01); *A01K 2267/0325* (2013.01); *A01K 2267/0331* (2013.01); *A01K 2267/0368* (2013.01); *A01K 2267/0375* (2013.01); *A01K 2267/0381* (2013.01); *A61K 38/00* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 5,595,721 A | 1/1997 | Kaminski et al. | |
| 5,969,102 A | 10/1999 | Bram et al. | |
| 6,297,367 B1 | 10/2001 | Tribouley | |
| 6,316,222 B1 | 11/2001 | Bram et al. | |
| 6,403,770 B1 | 6/2002 | Yu et al. | |
| 6,475,986 B1 | 11/2002 | Aggarwal | |
| 6,475,987 B1 | 11/2002 | Shu | |
| 6,541,224 B2 | 4/2003 | Yu et al. | |
| 6,623,941 B1 | 9/2003 | Ruben et al. | |
| 6,689,579 B1 | 2/2004 | Yu et al. | |
| 6,869,605 B2 | 3/2005 | Browning et al. | |
| 7,833,529 B1 * | 11/2010 | Gross | C07K 14/70578 424/143.1 |
| 8,071,092 B1 * | 12/2011 | Yu | C07H 21/04 424/130.1 |
| 2001/0010925 A1 | 8/2001 | Wiley | |
| 2002/0004587 A1 | 1/2002 | Miller et al. | |
| 2002/0037852 A1 | 3/2002 | Browning et al. | |
| 2002/0055624 A1 | 5/2002 | Wiley | |
| 2002/0064829 A1 | 5/2002 | Yu et al. | |
| 2002/0115112 A1 | 8/2002 | Yu et al. | |
| 2002/0165156 A1 | 11/2002 | Browning et al. | |
| 2002/0172674 A1 | 11/2002 | Jeffrey et al. | |
| 2003/0022239 A1 | 1/2003 | Baker et al. | |
| 2003/0023038 A1 | 1/2003 | Rennert | |
| 2003/0053984 A1 | 3/2003 | Tschopp et al. | |
| 2003/0082175 A1 | 5/2003 | Schneider et al. | |
| 2003/0095967 A1 | 5/2003 | MacKay et al. | |
| 2003/0100068 A1 | 5/2003 | Lam et al. | |
| 2003/0100074 A1 | 5/2003 | Yu et al. | |
| 2003/0108992 A1 | 6/2003 | Lenardo et al. | |
| 2003/0119149 A1 | 6/2003 | Reddy | |
| 2003/0148445 A1 | 8/2003 | Shu | |
| 2003/0148454 A1 | 8/2003 | Marshak-Rothstein et al. | |
| 2003/0166546 A1 | 9/2003 | Aggarwal | |
| 2003/0166864 A1 | 9/2003 | Yu et al. | |
| 2003/0175208 A1 | 9/2003 | Yu et al. | |
| 2003/0194743 A1 | 10/2003 | Beltzer et al. | |
| 2003/0194745 A1 | 10/2003 | McDowell et al. | |
| 2003/0198640 A1 | 10/2003 | Yu et al. | |
| 2003/0211509 A1 | 11/2003 | Wiley | |
| 2004/0013674 A1 | 1/2004 | Ambrose et al. | |
| 2004/0028658 A1 | 2/2004 | Faustman | |

(Continued)

FOREIGN PATENT DOCUMENTS

| | | |
|---|---|---|
| EP | 0 869 180 | 6/1999 |
| EP | 0 921 194 | 6/1999 |

(Continued)

OTHER PUBLICATIONS

Ngo et al.; in The Protein Folding Problem and Tertiary Structure Prediction,1994 Merz et al., (ed.), Birkhauser, Boston, MA, pp. 433 and 492-495.).*
Dang et al (J Immunol. 155(6):3205-3212, 1995).*
Dawson et al, Rheumatology, 44:449-455, 2005.*
Bacman et al, Investigative Opthalmology and visual Science, 42(2):321-327, 2001.*
Cohen in Fundamental Immunology, Paul ed, Lippincott-Raven Philadelphia, PA, 1999, chapter 33.*
Schwartz et al in Paul, "Fundamental Immunology", 1989, p. 837.*
Shevach, E. in Fundamental Immunology, Paul ed, Lippincott-Raven Philadelphia, PA, 1999, chapter 34.*
International Search Report, International Application No. PCT/US00/01788, WO 00/43032.
Partial International Search Report for International Application No. PCT/US01/28006, mailed Sep. 6, 2002, WO 02/024909.
International Search Report, International Application No. PCT/US01/28006, mailed Mar. 28, 2003, WO 02/024909.
Colman P.M., "Effects of amino acid sequence changes on antibody-antigen interaction," 55th Forum in Immunol., *Res. Immunol.*, 145(1): 33-36 (1994).
Dang et al., "SLE—Like Autoantibodies and Sjögren's Syndrome—Like Lymphoproliferation in TGF-β Knockout Mice," *J. Immunol.*, 155:3205-3212 (1995).

(Continued)

*Primary Examiner* — Patricia Duffy

(74) *Attorney, Agent, or Firm* — Finnegan, Henderson, Farabow, Garrett & Dunner, LLP

(57) ABSTRACT

The invention provides methods for treating or preventing disorders associated with expression of BAFF comprising BAFF and fragments thereof, antibodies, agonists and antagonists.

17 Claims, 44 Drawing Sheets

(56) References Cited

U.S. PATENT DOCUMENTS

| | | |
|---|---|---|
| 2004/0033511 A1 | 2/2004 | Pfizenmaier et al. |
| 2004/0038349 A1 | 2/2004 | Hilbert et al. |
| 2004/0072188 A1 | 4/2004 | Ambrose et al. |

FOREIGN PATENT DOCUMENTS

| | | |
|---|---|---|
| EP | 1 146 892 | 8/2003 |
| WO | WO 97/33902 | 9/1997 |
| WO | WO 98/18921 | 5/1998 |
| WO | WO 98/27114 | 6/1998 |
| WO | WO 98/39361 | 9/1998 |
| WO | WO 98/55620 | 12/1998 |
| WO | WO 98/55621 | 12/1998 |
| WO | WO 99/04001 | 1/1999 |
| WO | WO 99/11791 | 3/1999 |
| WO | WO 99/12964 | 3/1999 |
| WO | WO 99/12965 | 3/1999 |
| WO | WO 99/26463 | 6/1999 |
| WO | WO 99/33980 | 7/1999 |
| WO | WO 00/26244 | 5/2000 |
| WO | WO 00/39295 | 7/2000 |
| WO | WO 00/40716 | 7/2000 |
| WO | WO 00/43032 | 7/2000 |
| WO | WO 00/45836 | 8/2000 |
| WO | WO 00/47740 | 8/2000 |
| WO | WO 00/50597 | 8/2000 |
| WO | WO 00/50633 | 8/2000 |
| WO | WO 00/58362 | 10/2000 |
| WO | WO 00/60079 | 10/2000 |
| WO | WO 00/68378 | 11/2000 |
| WO | WO 00/77256 | 12/2000 |
| WO | WO 01/12812 | 2/2001 |
| WO | WO 01/24811 | 4/2001 |
| WO | WO 01/40466 | 6/2001 |
| WO | WO 01/42298 | 6/2001 |
| WO | WO 01/49318 | 7/2001 |
| WO | WO 01/58949 | 8/2001 |
| WO | WO 01/90304 | 11/2001 |
| WO | WO 01/96528 | 12/2001 |
| WO | WO 02/02641 | 1/2002 |
| WO | WO 02/08284 | 1/2002 |
| WO | WO 02/15930 | 2/2002 |
| WO | WO 02/18620 | 3/2002 |
| WO | WO 02/24909 | 3/2002 |
| WO | WO 02/38766 | 5/2002 |
| WO | WO 02/009262 | 11/2002 |
| WO | WO 03/001877 | 1/2003 |
| WO | WO 03/014294 | 2/2003 |
| WO | WO 03/022877 | 3/2003 |
| WO | WO 03/024991 | 3/2003 |
| WO | WO 03/033658 | 4/2003 |
| WO | WO 03/035846 | 5/2003 |
| WO | WO 03/040307 | 5/2003 |
| WO | WO 03/050134 | 6/2003 |
| WO | WO 03/055979 | 7/2003 |
| WO | WO 03/060071 | 7/2003 |
| WO | WO 03/060072 | 7/2003 |
| WO | WO 2004/016737 | 2/2004 |
| WO | WO 2004/035735 | 4/2004 |
| WO | WO 2005/005462 | 1/2005 |

OTHER PUBLICATIONS

Do et al., "Attenuation of Apoptosis Underlies B Lymphocyte Stimulator Enhancement of Humoral Immune Response," *J. Exp. Med.* 192(7):953-964 (2000).

Domingues, H.M. "Rational Design Strategies to Improve Cytokine Foldability and Minimization of a Functional Motif: The IL-4 Case," *Thesis University of Utrecht*, p. 48, line 25—p. 51, line 6, p. 94; table III (1999).

Furie et al., "Safety, Pharmacokinetic and Pharmacodynamic Results of a Phase 1 Single and Double Dose-Escalation Study of LymphoStat-B in SLE Patients," American College of Pheumatology (ACR), 67th Annual Scientific meeting, *Abstract.* 922 (Oct. 23-28, 2003).

Gallagher et al., "A multicenter, open-label, prospective, randomized, dose-ranging pharmacokinetic study of the anti-TNF-α antibody afelimomab in patients with sepsis syndrome," *Intensive Care Med.*, 27:1169-1178 (2001).

GenBank Accession No. AK008142, Published Feb. 8, 2001.

Gordon et al., "BAFF/Blys Receptor 3 Comprises a Minimal TNF Receptor-Like Module that Encodes a Highly Focused Ligand-Binding Site," *Biochemistry* 42:5977-5983 (2003).

Gras et al., "BCMAp: an integral membrane protein in the Golgi apparatus of human mature B lymphocytes," *Intl. Immunol.*, 7:1093-1106 (1995).

Gross et al., "TACI and BCMA are receptors for a TNF homologue implicated in B-cell autoimmune disease," *Nature*, 404:995-999 (2000).

Hahne et al., "APRIL, a New Ligand of the Tumor Necrosis Factor Family, Stimulates Tumor Cell Growth," *J. Exp. Med.*, 188:1185-1190 (1998).

Halpern et al., "Effects of LymphoStat-B, a BLyS Antagonist, when Administered Intravenously to Cynomolgus Monkeys," American College of Rheumatology (ACR), 67th Annual Scientific meeting, Abstract, 1537 (Oct. 23-28, 2003).

Harlow E. and Lane D., Antibodies A Laboratory Manual, Cold Spring Harbor Laboratory Press, pp. 141-155 (1988).

Kalled et al., "BAFF: B cell survival factor and emerging therapeutic target for autoimmune disorders," *Expert. Opin. Ther. Targets*, 7(1):115-123 (2003).

Kashii et al., "Constitutive Expression and Role of the TNF Family Ligands in Apoptotic Killing of Tumor Cells by Human Nk Cells," *J. Immunol.*, 163:5358-66 (2003).

Kayagaki et al., "BAFF/BlyS Receptor 3 Binds the B Cell Survival Factor BAFF Ligand through a Discrete Surface Loop and Promotes Processing of NF-κB2," *Immunity.*, vol. 10, 17(4):515-524 (2002).

Khare et al., "Severe B cell hyperplasia and autoimmune disease in TALL-1 transgenic mice," *PNAS USA*, 97:3370-3375 (2000).

Khare et al., "The role of TALL-1 and APRIL in immune regulations," *Trends Immunol.* 22(2):61-63 (2001).

Kogan et al., "A Single Amino Acid Residue Can Determine the Ligand Specificity of E-selectin," *J. Biol. Chem.*, 270(23):14047-55 (1995).

Kwon et al., "Single Amino Acid Substitutes of $\alpha_1$—Antitrypsin That Confer Enhancement in Thermal Stability," *J. Biol. Chem.* 269:9627-9631 (1994).

Kwon et al., "Functions of newly identified members of the tumor necrosis factor receptor/ligand superfamilies in lymphocytes," *Curr. Opinion in Immunol.*, 340-345 (1999).

Laabi et al., "A new gene, BCM, on chromosome 16 is fused to the interleukin 2 gene by a t(4;16)(q26;p13) translocation in a malignant T cell lymphoma," *EMBO J.*, 11:3897-3904 (1992).

Laabi et al., "The BCMA gene, preferentially expressed during B lymphoid maturation, is bidirectionally transcribed," *Nucleic Acids Res.*, 22:1147-1154 (1994).

Mackay et al., "Mice Transgenic for BAFF Develop Lymphocytic Disorders Along with Autoimmune Manifestations," *J. Exp. Med.*, 190:1697-1710 (1999).

Mackay, F. and Ambrose, C., "The TNF family members BAFF and APRIL: the growing complexity," *Cytokine & Growth Factor Reviews*, 14:311-324 (2003).

Madry et al., "The characterization of murine BCMA gene defines it as a new member of the tumor necrosis factor receptor superfamily," *Intl. Immunol.*, 10:1693-1702 (1998).

Marietta et al., "The level of BlyS (BAFF) correlates with the titre of autoantibodies in human Sjögren's syndrome," *Ann Rheum Dis.*, 62:168-171 (2003).

Marsters et al., "Interaction of the TNF Homologues Blys and APRIL with the TNF Receptor Homologues BCMA and TACI" *Curr. Biol.* 10:785-788 (2000).

Moore et al., "BLyS: Member of the Tumor Necrosis Factor Family and B Lymphocyte Stimulator," *Science*, 285:260-263 (1999).

Mukhopadhyay et al., "Identification and Characterization of a Novel Cytokine, THANK, a TNF Homologue That Activates Apoptosis, Nuclear Factor-κB, and c-Jun NH$_2$-Terminal Kinase," *J. Biol. Chem.*, 274:15978-15981 (1999).

(56) References Cited

OTHER PUBLICATIONS

Ngo et al., "Computational Complexity, Protein Structure Prediction, and the Levinthal Paradox," *Birkhauser*, ch. 14:491-494 (1994).
Parry et al., "Pharmacokinetics and Immunological Effects of Exogenously Administered Recombinant Human B Lymphocyte Stimulator (BlyS) in Mice," *Journ. Pharm. Exp. Ther.*, 296(2):396-404 (2001).
Pitti et al., "Genomic amplification of a decoy receptor for Fas ligand in lung and colon cancer," *Nature*, 396:699-703 (1998).
Schein, C.H., "Production of Soluble Recombinant Proteins in Bacteria," *Biotechnology* 7:1141-1149 (1989).
Schiemann et al., "An Essential Role for BAFF in the Normal Development of B Cells Through a BCMA-Independent Pathway" *Science* 293:2111-2114 (2001).
Schneider et al., "BAFF, a Novel Ligand of the Tumor Necrosis Factor Family, Stimulates B Cell Growth," *J. Exp. Med.*, 189:1747-1756 (1999).
Shu, H.B. and Johnson, H, "B cell maturation protein is a receptor for the tumor necrosis factor family member TALL-1," *PNAS USA*, 97:9156-9161 (1999).
Shu et al., "TALL-1 is a novel member of the TNF family that is down-regulated by mitogens," *J. Leukocyte Biol.* 65:680-683 (1999).
Stump et al., "Human Genome Sciences Initiates Trial of a New Drug for Systemic Lupus Erythematosus and Other Autoimmune Diseases," *HGS Press Release*, pp. 1-4 and *Human Genome Sciences Product Guides*, pp. 1-9 and pp. 1-13 (Nov. 2001).
Thompson et al., "BAFF Binds to the Tumor Necrosis Factor Receptor-like Molecule B Cell Maturation Antigen and is Important for Maintaining the Peripheral B Cell Population," *J. Exp. Med.*, 192:129-135 (2000).
Thompson et al., "BAFF interacts with the orphan receptor, BCMA," *Scandinavian J. of Immunol., Abstract*, 65 (2000).
Thompson, J.S. et al., "BAFF-R, A Newly Identified TNF Receptor That Specifically Interacts with BAFF," *Science* 293:2108-211 (2001).
Von Bulow & Bram, "NT-AT Activation Induced by a CAML-Interacting Member of the Tumor Necrosis Factor Receptor Superfamily," *Science* 278:138-141 (1997).
Von Bülow et al., "Regulation of the T-Independent Humoral Response by TACI," *Immunity*, 14:573-582 (2001).
Waldschmidt et al., "Long Live the Mature B Cell—A Baffling Mystery Resolved," *Science* 293:2012-2013 (2001).
Ward PA and Mulligan MS, "Blocking of adhesion molecules in vivo as anti-inflammatory therapy," *Ther Immunol*, 1:165-171 (1994).
Ware CF, "APRIL and BAFF Connect Autoimmunity and Cancer," *J Exp Med.*, 192(11):F35-37 (2000).
Wood et al., "Prolines and amyloidogenicity in Fragments of the Alzheimer's Peptide β/A4," *Biochemistry* 34:724-730 (1995).
Wu et al., "Tumor Necrosis Factor (TNF) Receptor Superfamily Member TACI is a High Affinity Receptor of TNF Family Members APRIL and BlyS," *J. Biol. Chem.* 275(45):35478-35485 (2000).
Xia et al., "TACI is a TRAF-interacting Receptor for TALL-1, a Tumor Necrosis Factor Family Member Involved in B Cell Regulation," *J. Exp. Med.*, 192:137-143 (2000).
Yan, M. et. al., "Identification of a novel receptor for B lymphocyte stimulator that is mutated in a mouse strain with severe B cell deficiency," *Curr. Biol.* 11:1547-1552 (2001).
Yu et al., "APRIL and TALL-1 and receptors BCMA and TACI: system for regulating humoral immunity," *Nat. Immun.*, 1:252-256 (2000).
Database Accession No. AI250289, XP002206618, Mar. 21, 1999.
Database Accession No. Z99716.4, XP002206619, Dec. 21, 1998.
EMBL Database entry, ID No. AA682496, Dec. 10, 1997.
EMBL Database entry, ID No. H58828, Oct. 7, 1995.

* cited by examiner

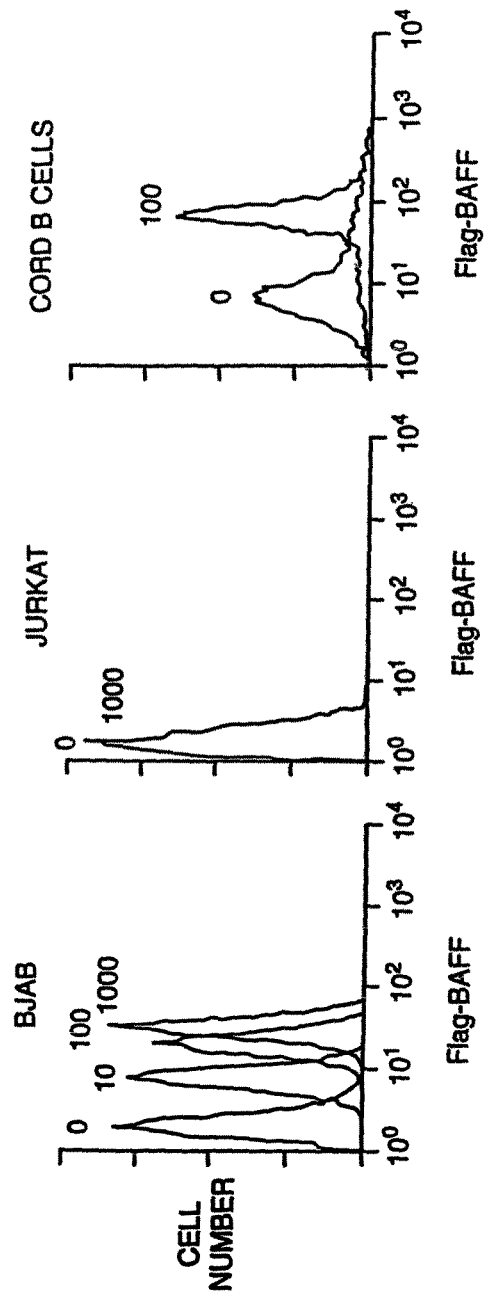

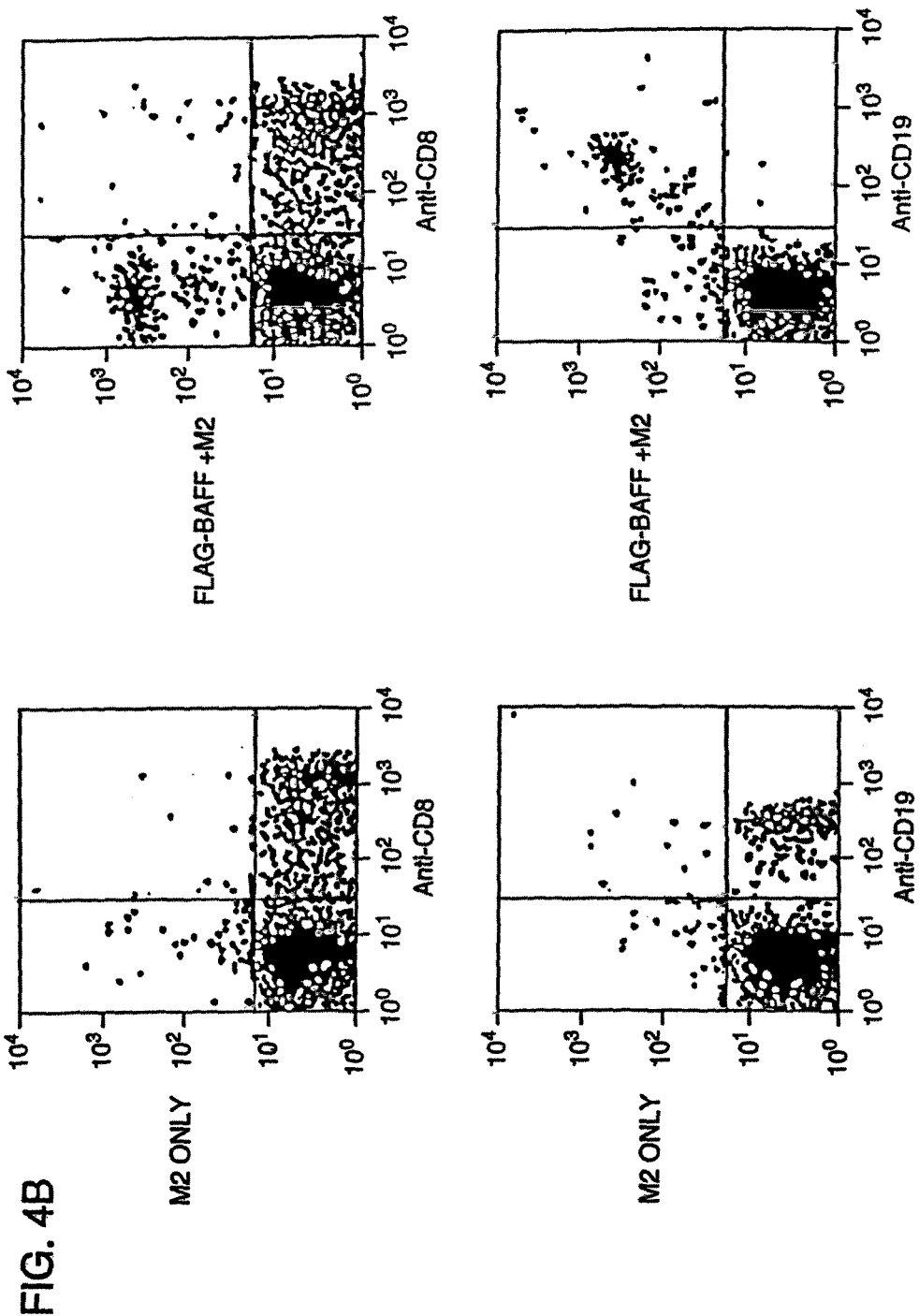

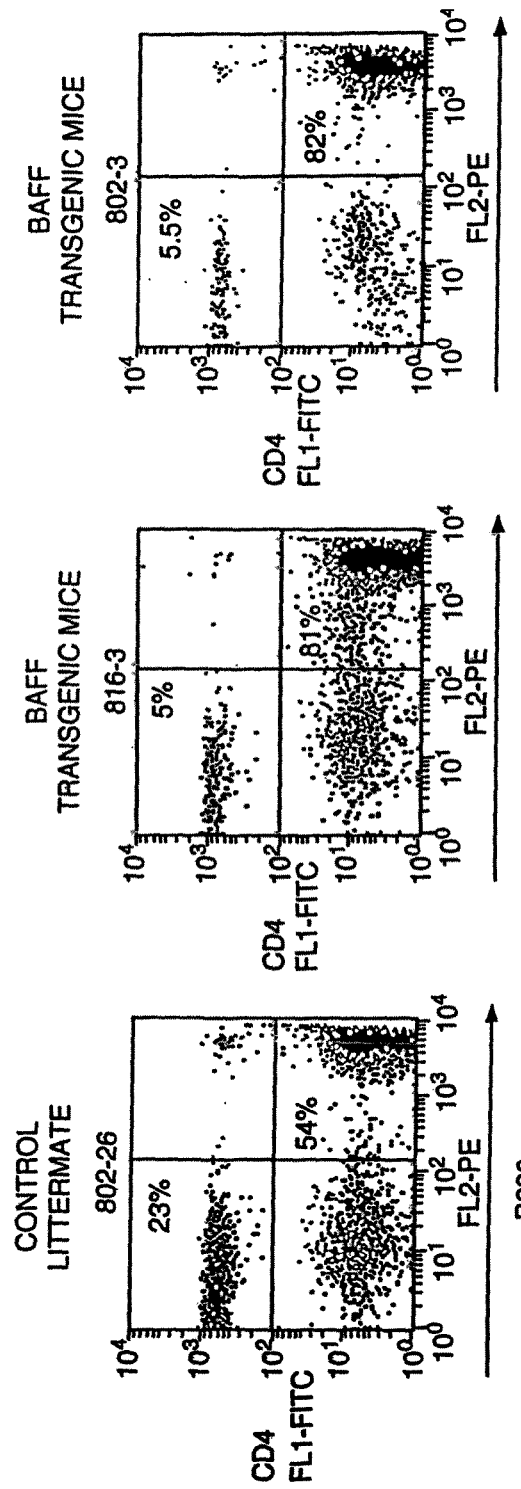

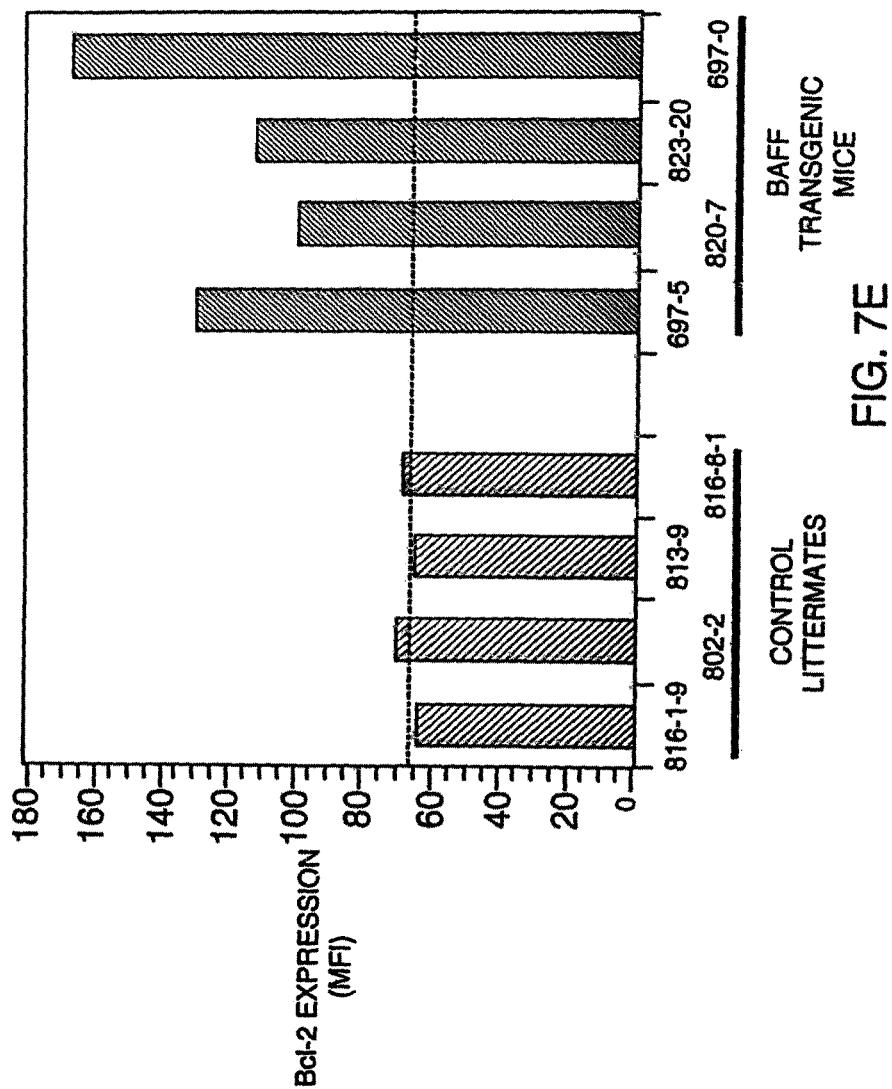

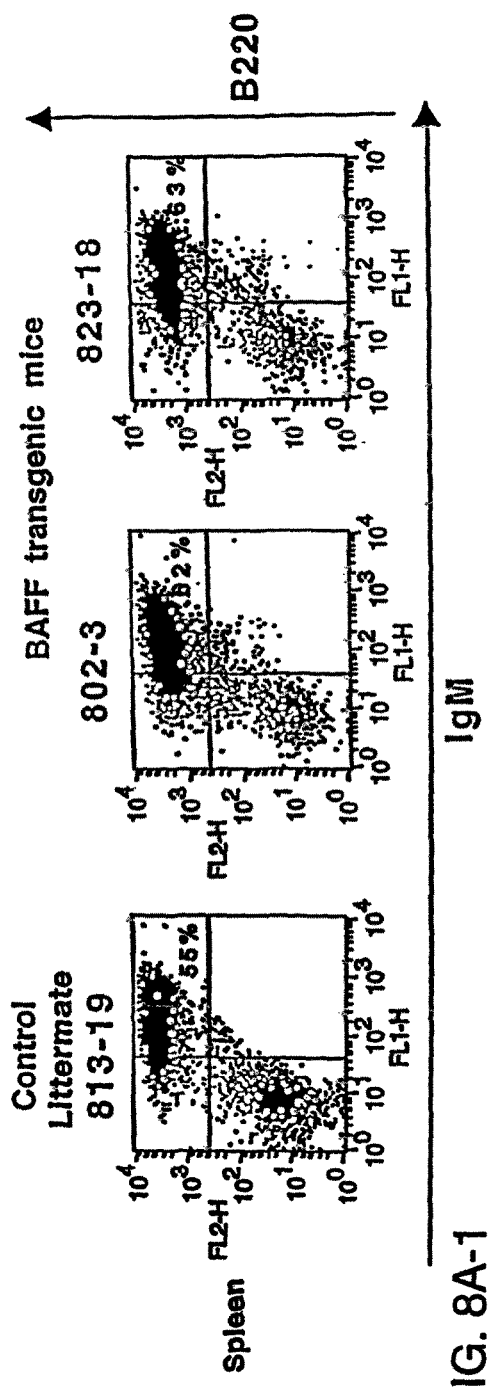
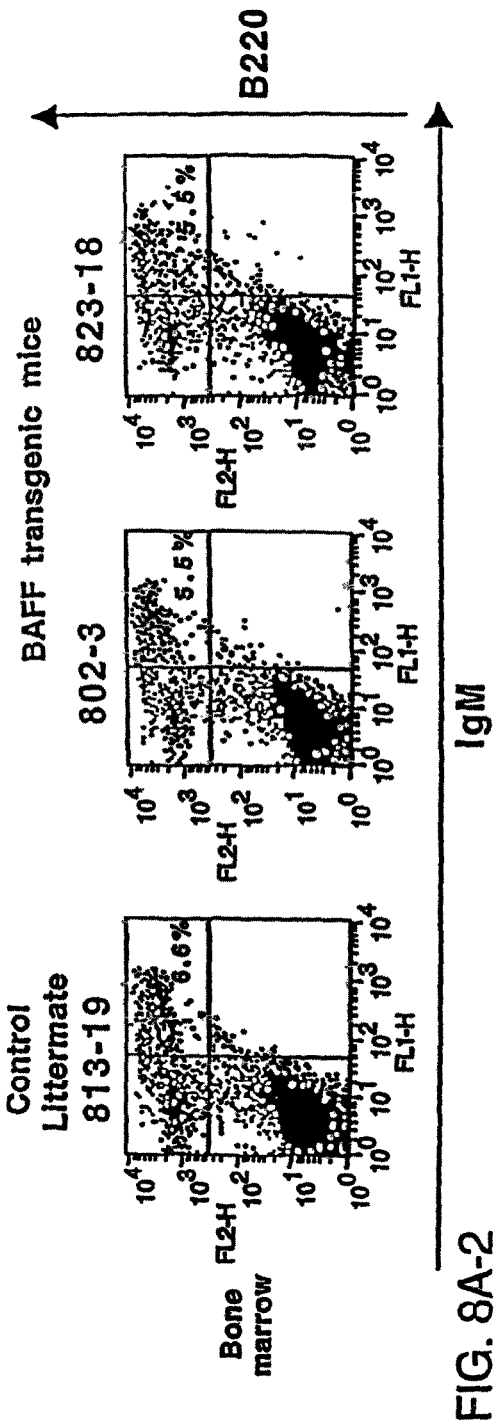
FIG. 8A-1
FIG. 8A-2

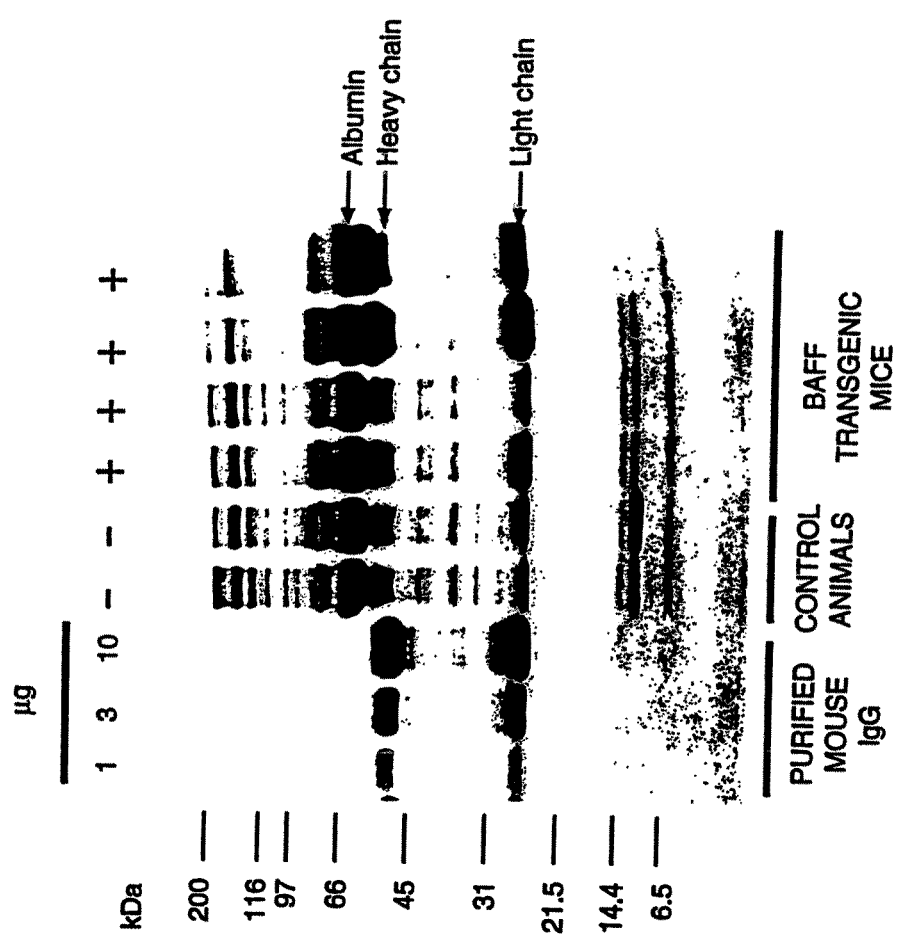

BAFF, INHIBITORS THEREOF AND THEIR USE IN THE MODULATION OF B-CELL RESPONSE AND TREATMENT OF AUTOIMMUNE DISORDERS

RELATED APPLICATIONS

This application is a divisional of application Ser. No. 11/065,669, filed Feb. 24, 2005, now abandoned which is a continuation of application Ser. No. 10/045,574, filed Nov. 7, 2001 (abandoned), all of which are incorporated herein by reference.

FIELD OF THE INVENTION

The present invention relates to the use of a ligand, BAFF, a β-cell activating factor belonging to the Tumor Necrosis Family and its blocking agents to either stimulate or inhibit the expression of B-cells and immunoglobulins. This protein and its receptor may have anti-cancer and/or immunoregulatory applications as well as uses for the treatment of immunosuppressive disorders such as HIV. Specifically, the ligand and its blocking agents may play a role in the development of hypertension and its related disorders. Furthermore, cells transfected with the gene for this ligand may be used in gene therapy to treat tumors, autoimmune diseases or inherited genetic disorders involving B-cells. Blocking agents, such as recombinant variants or antibodies specific to the ligand or its receptor, may have immunoregulatory applications as well. Use of BAFF as a B-cell stimulator for immune suppressed diseases including for example uses for patients undergoing organ transplantation (i.e. bone marrow transplant) as well as recovering from cancer treatments to stimulate production of B-cells are contemplated. Use of BAFF as an adjuvant and costimulator to boast and or restore B cells levels to approximate normal levels are also contemplated.

BACKGROUND OF THE INVENTION

The tumor-necrosis factor (TNF)-related cytokines are mediators of host defense and immune regulation. Members of this family exist in membrane-anchored forms, acting locally through cell-to-cell contact, or as secreted proteins capable of diffusing to more distant targets. A parallel family of receptors signals the presence of these molecules leading to the initiation of cell death or cellular proliferation and differentiation in the target tissue. Presently, the TNF family of ligands and receptors has at least 11 recognized receptor-ligand pairs, including: TNF:TNF-R; LT-α:TNF-R; LT-α/β: LT-β-R; FasL:Fas; CD40L:CD40; CD30L:CD30; CD27L: CD27; OX40L:OX40 and 4-1BBL:4-1BB. The DNA sequences encoding these ligands have only about 25% to about 30% identity in even the most related cases, although the amino acid relatedness is about 50%.

The defining feature of this family of cytokine receptors is found in the cysteine rich extracellular domain initially revealed by the molecular cloning of two distinct TNF receptors. This family of genes encodes glycoproteins characteristic of Type I transmembrane proteins with an extracellular ligand binding domain, a single membrane spanning region and a cytoplasmic region involved in activating cellular functions. The cysteine-rich ligand binding region exhibits a tightly knit disulfide linked core domain, which, depending upon the particular family member, is repeated multiple times. Most receptors have four domains, although there may be as few as three, or as many as six.

Proteins in the TNF family of ligands are characterized by a short N-terminal stretch of normally short hydrophilic amino acids, often containing several lysine or arginine residues thought to serve as stop transfer sequences. Next follows a transmembrane region and an extracellular region of variable length, that separates the C-terminal receptor binding domain from the membrane. This region is sometimes referred to as the "stalk". The C-terminal binding region comprises the bulk of the protein, and often, but not always, contains glycosylation sites. These genes lack the classic signal sequences characteristic of type I membrane proteins, type II membrane proteins with the C terminus lying outside the cell, and a short N-terminal domain residing in the cytoplasm. In some cases, e.g., TNF and LT-α, cleavage in the stalk region can occur early during protein processing and the ligand is then found primarily in secreted form. Most ligands, however, exist in a membrane form, mediating localized signaling.

The structure of these ligands has been well-defined by crystallographic analyses of TNF, LT-α, and CD40L. TNF and lymphotoxin-I (LT-I) are both structured into a sandwich of two anti-parallel β-pleated sheets with the "jelly roll" or Greek key topology. The rms deviation between the Cα and β residues is 0.61 C, suggesting a high degree of similarity in their molecular topography. A structural feature emerging from molecular studies of CD40L, TNF and LT-α is the propensity to assemble into oligomeric complexes. Intrinsic to the oligomeric structure is the formation of the receptor binding site at the junction between the neighboring subunits creating a multivalent ligand. The quaternary structures of TNF, CD40L and LT-α have been shown to exist as trimers by analysis of their crystal structures. Many of the amino acids conserved between the different ligands are in stretches of the scaffold β-sheet. It is likely that the basic sandwich structure is preserved in all of these molecules, since portions of these scaffold sequences are conserved across the various family members. The quaternary structure may also be maintained since the subunit conformation is likely to remain similar.

TNF family members can best be described as master switches in the immune system controlling both cell survival and differentiation. Only TNF and LTα are currently recognized as secreted cytokines contrasting with the other predominantly membrane anchored members of the TNF family. While a membrane form of TNF has been well-characterized and is likely to have unique biological roles, secreted TNF functions as a general alarm signaling to cells more distant from the site of the triggering event. Thus TNF secretion can amplify an event leading to the well-described changes in the vasculature lining and the inflammatory state of cells. In contrast, the membrane bound members of the family send signals though the TNF type receptors only to cells in direct contact. For example T cells provide CD40 mediated "help" only to those B cells brought into direct contact via cognate TCR interactions. Similar cell-cell contact limitations on the ability to induce cell death apply to the well-studied Fas system.

It appears that one can segregate the TNF ligands into three groups based on their ability to induce cell death. First, TNF, Fas ligand and TRAIL can efficiently induce cell death in many lines and their receptors mostly likely have good canonical death domains. Presumably the ligand to DR-3 (RAMP/WSL-1) would also all into this category. Next there are those ligands which trigger a weaker death signal limited to few cell types and TWEAK, CD30 ligand and LTa1b2 are examples of this class. How this group can trigger cell death in the absence of a canonical death domain is an interesting question and suggests that a separate weaker death signaling mechanism exists. Lastly, there are those members that cannot efficiently deliver a death signal. Probably all groups can have antiproliferative effects on some cell types consequent to inducing cell differentiation e.g. CD40. Funakoshi et al. (1994).

The TNF family has grown dramatically in recent years to encompass at least 11 different signaling pathways involving regulation of the immune system. The widespread expression patterns of TWEAK and TRAIL indicate that there is still more functional variety to be uncovered in this family. This aspect has been especially highlighted recently in the discovery of two receptors that affect the ability of rous sarcoma and herpes simplex virus to replicate as well as the historical observations that TNF has anti-viral activity and pox viruses encode for decoy TNF receptors. Brojatsch et al. (1996); Montgomery et al. (1996); Smith et al. (1994), 76 *Cell* 959-962; Vassalli et al. (1992), 10 *Immunol.* 411-452.

TNF is a mediator of septic shock and cachexia, and is involved in the egulation of hematopoietic cell development. It appears to play a major role as a mediator of inflammation and defense against bacterial, viral and parasitic infections as well as having antitumor activity. TNF is also involved in different autoimmune diseases. TNF may be produced by several types of cells, including macrophages, fibroblasts, T cells and natural killer cells. TNF binds to two different receptors, each acting through specific intracellular signaling molecules, thus resulting in different effects of TNF. TNF can exist either as a membrane bound form or as a soluble secreted cytokine.

LT-I shares many activities with TNF, i.e. binding to the TNF receptors, but unlike TNF, appears to be secreted primarily by activated T cells and some β-lymphoblastoid tumors. The heteromeric complex of LT-α and LT-β is a membrane bound complex which binds to the LT-β receptor. The LT system (LTs and LT-R) appears to be involved in the development of peripheral lymphoid organs since genetic disruption of LT-β leads to disorganization of T and B cells in the spleen and an absence of lymph nodes. The LT-β system is also involved in cell death of some adenocarcinoma cell lines.

Fas-L, another member of the TNF family, is expressed predominantly on activated T cells. It induces the death of cells bearing its receptor, including tumor cells and HIV-infected cells, by a mechanism known as programmed cell death or apoptosis. Furthermore, deficiencies in either Fas or Fas-L may lead to lymphoproliferative disorders, confirming the role of the Fas system in the regulation of immune responses. The Fas system is also involved in liver damage resulting from hepatitis chronic infection and in autoimmunity in HIV-infected patients. The Fas system is also involved in T-cell destruction in HIV patients. TRAIL, another member of this family, also seems to be involved in the death of a wide variety of transformed cell lines of diverse origin.

CD40-L, another member of the TNF family, is expressed on T cells and induces the regulation of CD40-bearing B cells. Furthermore, alterations in the CD40-L-gene result in a disease known as X-linked hyper-IgM syndrome. The CD40 system is also involved in different autoimmune diseases and CD40L is known to have antiviral properties. Although the CD40 system is involved in the rescue of apoptotic B cells, in non-immune cells it induces apoptosis. Many additional lymphocyte members of the TNF family are also involved in costimulation.

Generally, the members of the TNF family have fundamental regulatory roles in controlling the immune system and activating acute host defense systems. Given the current progress in manipulating members of the TNF family for therapeutic benefit, it is likely that members of this family may provide unique means to control disease. Some of the ligands of this family can directly induce the apoptotic death of many transformed cells e.g. LT, TNF, Fas ligand and TRAIL. Nagata (1997) 88 *Cell* 355-365. Fas and possibly TNF and CD30 receptor activation can induce cell death in nontransformed lymphocytes which may play an immunoregulatory function. Amakawa et al. (1996) 84 *Cell* 551-562; Nagata (1997) 88 *Cell* 355-365; Sytwu et al. (1996); Zheng et al. (1995) 377 *Nature* 348-351. In general, death is triggered following the aggregation of death domains which reside on the cytoplasmic side of the TNF receptors. The death domain orchestrates the assembly of various signal transduction components which result in the activation of the caspase cascade. Nagata (1997) 88 *Cell* 355-365. Some receptors lack canonical death domains, e.g. LTb receptor and CD30 (Browning et al. (1996); Lee et al. (1996)) yet can induce cell death, albeit more weakly. It is likely that these receptors function primarily to induce cell differentiation and the death is an aberrant consequence in some transformed-cell lines, although this picture is unclear as studies on the CD30 null mouse suggest a death role in negative selection in the thymus. Amakawa et al. (1996) 84 *Cell* 551-562. Conversely, signaling through other pathways such as CD40 is required to maintain cell survival. Thus, there is a need to identify and characterize additional molecules which are members of the TNF family thereby providing additional means of controlling disease and manipulating the immune system.

Sjögren's syndrome (SS) is a chronic inflammatory disorder characterized by the destruction of exocrine glands such as salivary and lacrimal glands, leading to symptoms of dry mouth (xerostomia) and eyes keratoconjunctivitis sicca). Jonsson et al. (2000) Sjogren's syndrome in *Arthritis and allied conditions* 1826-1849. SS is regarded as an autoimmune disease characterized by the presence of large mononuclear cell infiltrates in exocrine glands, B cell hyperreactivity and various serum autoantibodies. Jonsson et al. (2000); Manoussakis et al. (1998) Sjogren's syndrome in *The autoimmune diseases*. Academic Press, 3814. SS can develop alone or in association with other autoimmune disorders such as systemic lupus erythematosus (SLE) and rheumatoid arthritis (RA). Jonnson et al. (2000); Manoussakis et al. (1998).

Abnormal B cell activity is a predominant feature of SS, which is manifested by massive polyclonal B cell activation and elevated secretion of autoantibodies such as rheumatoid factors (RF), anti-Ro (SS-A), anti-La (SS-B) and anti-λ-fodrin autoantibodies. Jonnson et al. (2000); Manoussakis et al. (1998); MacSween et al. (1967) *Ann. Rheum. Dis.* 26: 402-411; Haneji et al. (1997) *Science* 276; 604-607. Intense B cell activity such as germinal center reactions occur in exocrine glands of some patients, placing them in a high risk category for the development of lymphomas. Jonsson et al. (2000); Stott et al. (1998) *J. Clin. Invest.* 102:938-946. However, the role of B cells and autoantibodies in the pathogenesis of SS still remains unclear.

SUMMARY OF THE INVENTION

Here we characterize the functional properties of a new ligand of the TNF cytokine family. The new ligand, termed BAFF (B cell activating factor belonging to the TNF family), appears to be expressed by T cells and dendritic cells for the purpose of B-cell costimulation and may therefore play an important role in the control of B cell function. In addition, we have generated transgenic mice overexpressing BAFF under the control of a liver-specific promoter. These mice have excessive numbers of mature B cells, spontaneous germinal center reactions, secrete autoantibodies, and have high plasma cell numbers in secondary lymphoid organs and Ig deposition in the kidney.

The BAFF Tg mice develop as they age a secondary condition to their lupus-like disease, showing interesting similarities with that of SS in humans. We also identified a new and potentially pathogenic B cell population with MZ-like features infiltrating salivary glands of BAFF Tg mice.

Accordingly, the present invention is directed to the use of BAFF-ligands, blocking agents and antibodies for the ligand, to either stimulate or inhibit the growth of B-cells and the secretion of immunoglobulin. The claimed invention may be used for therapeutic applications in numerous diseases and disorders, as discussed in more detail below, as well as to obtain information about, and manipulate, the immune system and its processes. Further, this invention can be used as a method of stimulating or inhibiting the growth of B-cells and the secretion of immunoglobulins. BAFF associated molecules, as described by this invention, may also have utility in the treatment of autoimmune diseases, disorders relating to B-cell proliferation and maturation, BAFF ligand regulation and inflammation. The invention may be involved in the regulation or prevention of hypertension and hypertension-related disorders of the renal and cardiovascular tissue.

Additional features and advantages of the invention will be set forth in the description which follows, and in part will be apparent from the description, or may be learned by practice of the invention. The objectives and other advantages of the invention will be realized and attained by the methods particularly pointed out in the written description and claims hereof, as well as in the appended drawings.

Thus, to achieve these and other advantages, and in accordance with the purpose of the invention, as embodied and broadly described herein, the invention includes a method of effecting B-cell growth and secretion of immunoglobulins through the administration of various BAFF ligands and related molecules.

The invention also contemplates stimulating B-cell growth through the use of BAFF ligands or active fragments of the polypeptide. The polypeptide may be use alone or with a CD40 ligand or an anti-murine antibody.

In other embodiments, the invention relates to methods of stimulation of dendritic cell-induced Bell growth and maturation through the use of BAFF ligands or active fragments of BAFF. Again, the polypeptide may be used alone or with CD40 ligand or anti-µ antibodies.

In other embodiments, blocking agents of BAFF and the BAFF receptor have been used to inhibit B-cell growth and immunoglobulin secretion. These agents an be inoperative, recombinant BAFF, BAFF specific antibodies, BAFF-receptor specific antibodies or an anti-BAFF ligand molecule.

In yet other embodiments, the invention relates to the use of BAFF, BAFF related molecules and BAFF blocking agents to treat hypertension, hypertension related disorders, immune disorders, autoimmune diseases, inflammation and B-cell lympho-proliferate disorders. In another aspect, the invention relates to the use of BAFF, BAFF-related molecules and BAFF blocking agents to treat Sjogren's syndrome.

In a preferred embodiment, the invention relates to methods for treating or reducing the advancement, severity or effects of Sjogren's syndrome in a patient by administering a pharmaceutical preparation comprising a therapeutically effective amount of a BAFF blocking agent and a pharmaceutically acceptable carrier. In some embodiments, the BAFF blocking agent may be a soluble BAFF receptor molecule, an antibody directed against BAFF-ligand or an antibody directed against a BAFF receptor. The BAFF receptor may be BCMA, TACI, or BAFF R.

The invention encompasses the use of BAFF and BAFF-related molecules as either agonists or antagonists in effecting immune responses by effecting the growth and/or maturation of B-cells and secretion of immunoglobulin.

The invention relates in other embodiments to soluble constructs comprising BAFF which may be used to directly trigger BAFF mediated pharmacological events. Such events may have useful therapeutic benefits in the treatment of cancer, tumors or the manipulation of the immune system to treat immunologic diseases.

Additionally, in other embodiments the claimed invention relates to antibodies directed against BAFF ligand, which can be used, for example, for the treatment of cancers, and manipulation of the immune system to treat immunologic disease.

In yet other embodiments the invention relates to methods of gene therapy using the genes for BAFF.

The pharmaceutical preparations of the invention may, optionally, include pharmaceutically acceptable carriers, adjuvants, fillers, or other pharmaceutical compositions, and may be administered in any of the numerous forms or routes known in the art.

It is to be understood that both the foregoing general description and the following detailed description are exemplary and explanatory, and are intended to provide further explanation of the invention as claimed.

The accompanying drawings are included to provide a further understanding of the invention, and are incorporated in, and constitute a part of this specification, illustrate several embodiments of the invention, and together with the description serve to explain the principles of the invention.

Concentrated supernatants containing Flag-tagged BAFFs and APRIL were deglycosylated and analyzed by Western blotting using polyclonal anti-BAFF antibodies or anti-Flag M2, as indicated. All bands except processed BAFF also reacted with anti-Flag M2 (data not shown). (C) Full length BAFF is processed to a soluble form 293T-ells were transiently transfected with full length BAFF. Transfected cells and their concentrated supernatants were analyzed by Western blotting using polyclonal anti-BAFF antibodies. Supernatants corresponding to 10× the amount of cells were loaded onto the gel. (D) Size exclusion chromatography of soluble BAFF on Superdex-200. Concentrated supernatants containing soluble BAFF/short were fractionated on a Superdex-200 column and the eluted fractions analyzed by Western blotting using anti-Flag M2 antibody. The migration positions of the molecular mass markers (in kDa) are indicated on the left-hand side for SDS-PAGE and at the top of the figure for size exclusion chromatography.

Figures 3, 8A:
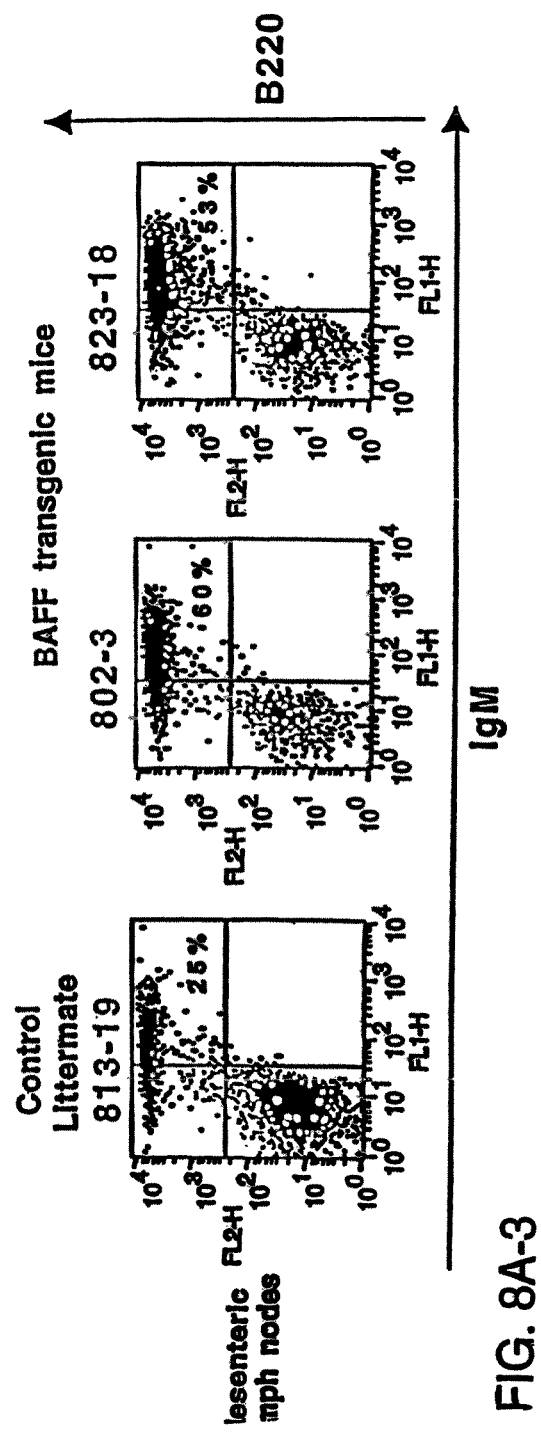

FIG. 3 depicts expression of BAFF (A) Northern blots (2 μg poly A$^+$ RNA per lane) of various human tissues were probed with BAFF antisense mRNA. (B) Reverse transcriptase amplification of BAFF, IL-2 receptor alpha chain and actin from RNA of purified blood T cells at various time points of PHA activation, E-rosetting negative blood cells (B cells and monocytes), in vitro derived immature dendritic cells, 293 cells, and 293 cells sterilely transfected with full length BAFF (293-BAFF). Control amplifications were performed in the absence of added cDNA. IL-2 receptor alpha chain was amplified as a marker of T cell activation.

FIG. 4 depicts BAFF binding to mature B cells. (A) Binding of soluble BAFF to BJAB and Jurkat cell lines, and to purified CD19$^+$ cells of cord blood. Cells were stained with the indicated amount (in ng/50 μl) of Flag-BAFF and analyzed by flow cytometry. (B) Binding of soluble BAFF to PBLs. PBLs were stained with anti-C8-FITC or with anti-19-FITC (horizontal axis) and with Flag-BAFF plus M2-biotin and avidin-PE (vertical axis). Flag-BAFF was omitted in controls.

FIG. 5 depicts BAFF costimulates B cell proliferation. (A) Surface expression of BAFF in stably transfected 293 cells 293-BAFF and 293 wild-type cells were stained with anti-BAFF mAb 43.9 and analyzed by flow cytometry. (B) Costimulation of PBLs by 293-BAFF cells. PBLs ($10^5$/well) were incubated with 15.000 glutaraldehyde-fixed 293 cells (293 wt or 293-BAFF) in the presence or absence of anti-B cell receptor antibody (anti-μ). Fixed 293 cells alone incorporated 100 cpm. (C) Dose dependent costimulation of PBL proliferation by soluble BAFF in the presence of anti-μ. Proliferation was determined after 72 h incubation by [$^3$H]-thymidine incorporation. Controls include cells treated with BAFF alone, with heat-denatured BAFF or with an irrelevant isotype matched antibody in place of anti-μ. (D) Comparison of (co)stimulatory effects of sCD40L and sBAFF on PBL proliferation. Experiment was performed as described in panel C. (E) BAFF costimulates Ig secretion of preactivated human B cells. Purified CD19$^+$ B cells were activated by coculture with EL-4 T cells and activated T cell supernatants for 5-6 d, then re-isolated and cultured for another 7 days in the presence of medium only (−) or containing 5% activated T cell supernatants (T-SUP) or a blend of cytokines (IL-2, IL-4, IL-10). The columns represent means of Ig concentrations for cultures with or without 1 μg/ml BAFF. Means±SD in terms of "fold increase" were 1.23±0.11 for medium only, 2.06±0.18 with T cell supernatants (4 experiments) and 1.45±0.06 with IL-2, IL-4 and IL-10 (2 experiments). These were performed with peripheral blood (3 experiments) or cord blood B cells (one experiment; 2.3 fold increase with T cell supernatants, 1.5 fold increase with IL-2, IL-4 and IL-10). (F) Dose-response curve for the effect of BAFF in cultures with T cell supernatants, as shown in panel D. Mean±SD of 3 experiments.

Figure 6:
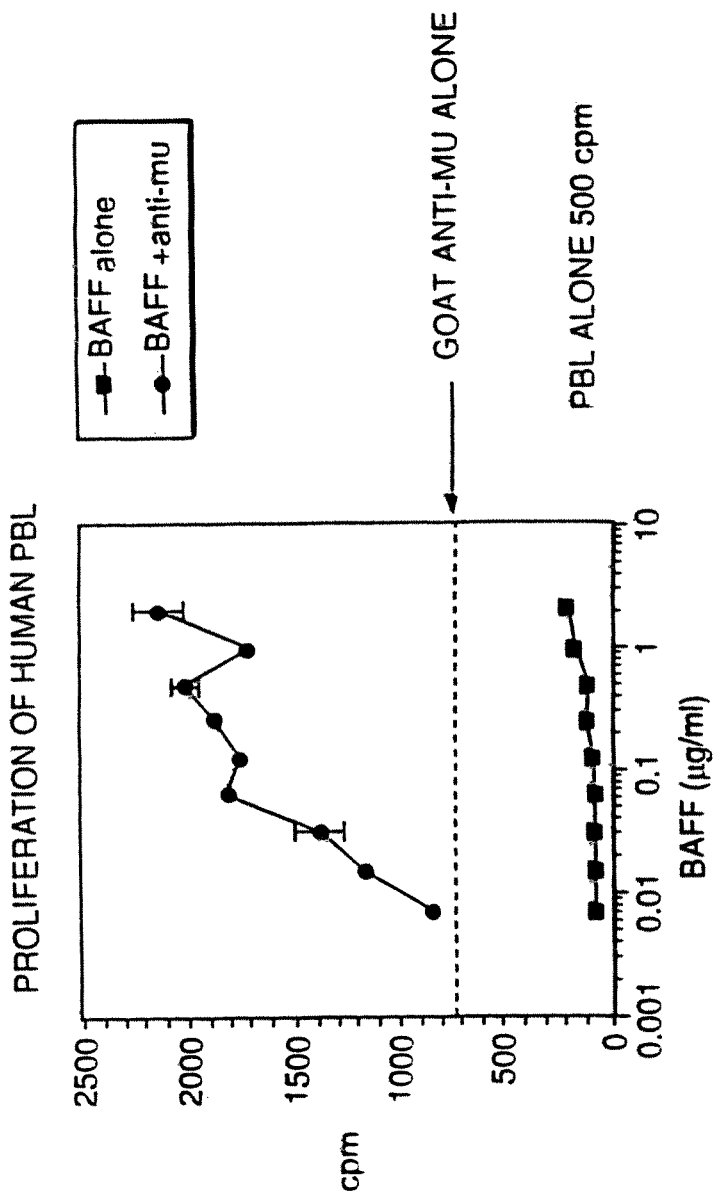

FIG. 6 depicts that BAFF acts as a cofactor for B cell proliferation. The proliferation of human PBL was measured alone (500 cpm), with the presence of BAFF ligand alone, with the presence of goat anti-murine (mu) alone, and with both BAFF ligand and anti-mu. The combination of both anti-mu and BAFF significantly raised proliferation of PBL as the concentration of BAFF increased suggesting BAFF's cofactor characteristics.

FIG. 7 depicts increased B cell numbers in BAFF Tg nice.
(A) Increased lymphocytes counts in BAFF Tg mice. The graph compares 12 control littermates (left panel) with 12 BAFF Tg mice (right panel). Lymphocytes counts are shown with circles and granulocytes (including neutrophils, eosinophils, basophils) with diamonds.

(B) Increased proportion of B cells in PBL from BAFF Tg mice. PBL were stained with both anti-B220-FITC and anti-CD4-PE for FACS analysis and gated on live cells using the forward side scatter. Percentages of CD4 and B220 positive cells are indicated. One control mouse (left) and two BAFF Tg mice (right) are shown and the results were representative of 7 animals analysed in each group.

(C) FACS analysis of the ratio of B to T cells in PBL. The difference between control animals and BAFF Tg mice in (A) and (C) was statistically significant (P<0.001).

(D) Increased MHC class II expression on B cells from BAFF T-g mice PBL MHC class II expression was analysed by FACS.

(E) Increased Bcl-2 expression in B cells from BAFF Tg mice PBL. Bcl-2 expression was measured by intracytoplasmic staining and cells were analysed by FACS. In both (D) and (E live cells were gated on the forward side scatter. Four control littermates (white bars) and 4 BAFF Tg mice are shown and are representative of at least 12 animals analysed for each group. MFI: mean of fluorescence intensity. The difference between control animals and BAFF Tg mice was statistically significant (P<0.005).

(F) Increased expression of effector T cells in BAFF Tg mice. PBL were stained with anti-CD4-Cychrome, anti-CD44-FITC and anti-L selectin-PE. Are shown CD4$^+$-gated cells. Percentages of CD44$^{hi}$/L-selectin$^{lo}$ cells are indicated. One control mouse (left) and two BAFF Tg mice (right) are shown and the results were representative of 8 animals analysed in each group.

FIG. 8 depicts increased B cell compartments in the spleen but not in the bone marrow of BAFF Tg mice.

(A) FACS staining for mature B cells using both anti-IgM-FITC and anti-B220-PE, in spleen (top panel), bone marrow (medium panel) and MLN (bottom panel). Percentages of B220+/IgM+ mature B cells are indicated.

(B) FACS staining for preB cells (B220+/CD43−) and proB cells (B220+/CD43+) in the bone marrow using anti-CD43-FITC, anti-B220-Cy-chrome and anti-IgM-PE simultaneously. Are shown cells gated on the IgM negative population. Percentages of preB cells (B220+/CD43−) and proB cells (B220+/CD43+) cells are indicated.

For all figures (A and B) one control mouse (left) and two BAFF Tg mice (right) are shown and results are representative of 7 animals analysed for each group.

FIG. 9 depicts increased Ig, RF and CIC levels in BAR Tg mice
(A) SDS-PAGE of two control sera (−) and 4 sera from BAFF Tg mice (+) side by side with the indicated amount of a purified mouse IgG for reference. The intensity of the albumin band in similar in all lanes indicating that the material loaded on the gel is equivalent for each sample. ELISA-based analysis of total mouse Ig (B), RF (C) and CIC (D) in the sera of 19 control littermates (white bars) and 21 BAFF Tg mice (Black bars). In the absence of a proper RF control, the titer (log base 2) for RF is defined as the dilution of the sera giving an O.D. 3 times higher than that of background. The quantity of CIC is defined as the quantity of PAP required to generate an O.D. equivalent to that obtained with the tested serum. The difference between control animals and BAFF Tg mice was statistically significant ($P<0.001$ in (B) and (C), $P<0.003$ in (D)).

FIG. 10 depicts the presence of anti-ssDNA and anti-dsDNA autoantibodies in some BAFF Tg mice.

(A) Analysis by ELISA of anti-ssDNA autoantibodies in 19 control littermates (gray bars) and 21 BAFF Tg mice (black bars).

(B) Analysis by ELISA of anti-ssDNA autoantibodies in 5 control littermates and the 5 animals showing levels of anti-ssDNA autoantibodies from (A).

(C) Paraffin sections of kidneys from a control mouse (left) and a BAFF Tg mouse (right), stained with goat anti-mouse Ig-HRP. Ig deposition is shown by a brown staining. These pictures are representative of 6 BAFF Tg mice analysed.

Figure 11:
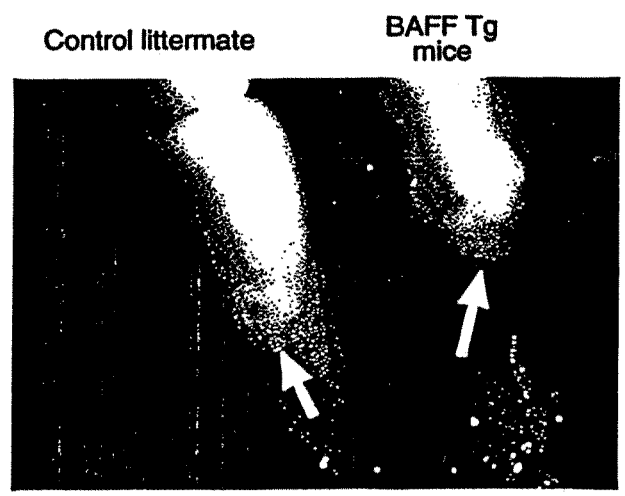

FIG. 11 depicts enlarged Peyer's patches in BAFF Tg mice. Photography of Peyers patches (indicated with an arrow) on the small intestine of a control mouse (left) and a BAFF Tg mouse (right). This pictures is representative of at least 12 mice sacrificed for each group. Magnification 5×

Figure 12:
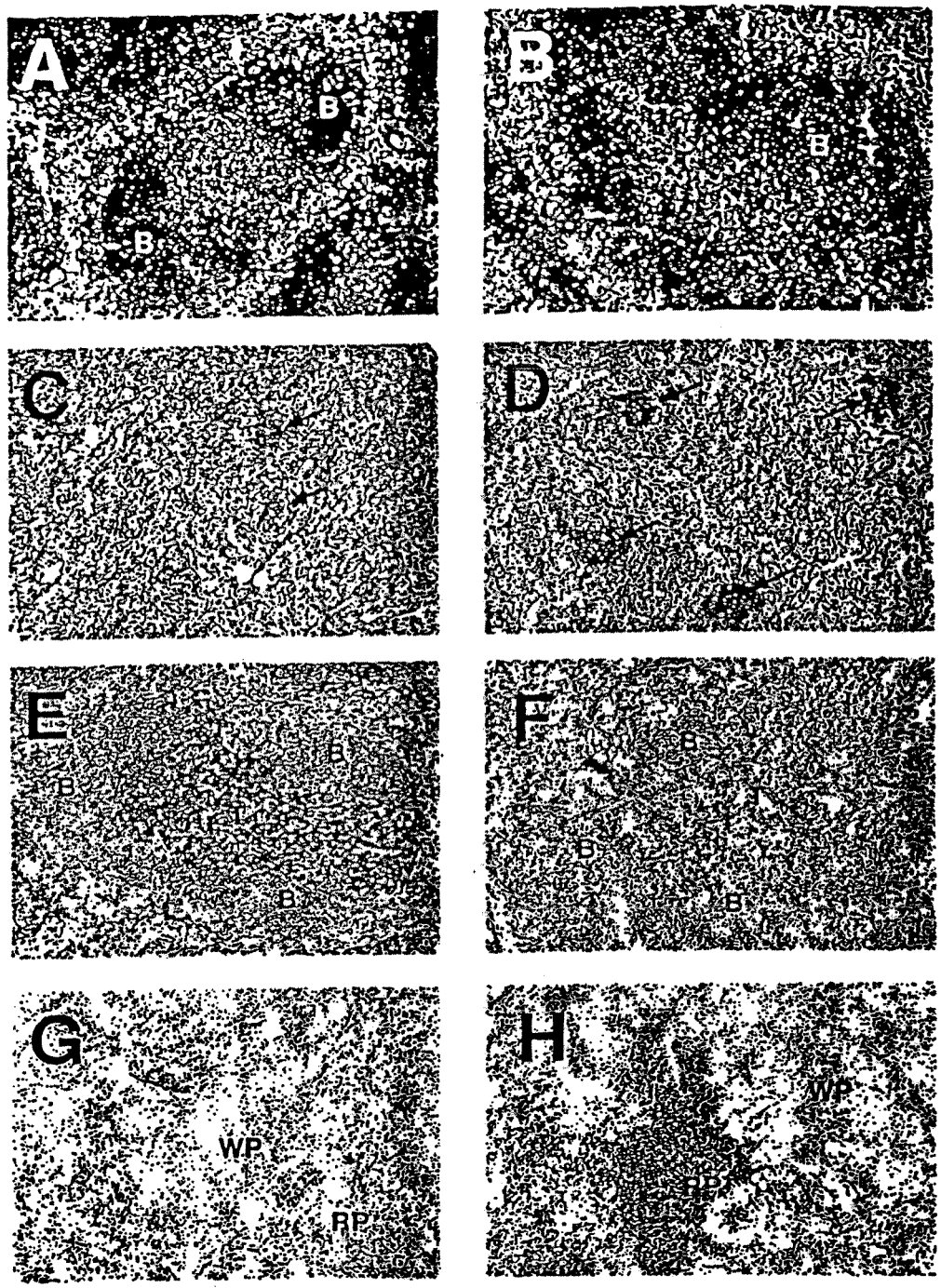

FIG. 12 depicts disrupted T and B cell organization, intense germinal center reactions, decreased number of dendritic cells and increased number of plasma cells in the spleen of BAFF Tg mice.

A control mouse is shown in A, C, E and G and a BAFF Tg in B, D, F, and H. B cells are blue and T cells brown (A and B). Germinal centers are shown with an arrow (C and D). Only few residual germinal centers are seen in control mice (C). CD11c positive dendritic cells are brown and appear in the T cell zone, bridging channels and the marginal zone (E). Very few are present in BAFF Tg mice (F). Syndecan-1-positive plasma cells were only detectable in the red pulp of BAFF Tg mice (H) but not control mice (CG).

These pictures are representative of at least 12 BAFF Tg mice analysed and 12 control mice. The magnification is 100× for all pictures except C and D which are 50×. B: B cell follicle, T: PALS, WP: white pulp, RP: red pulp.

Figure 13:
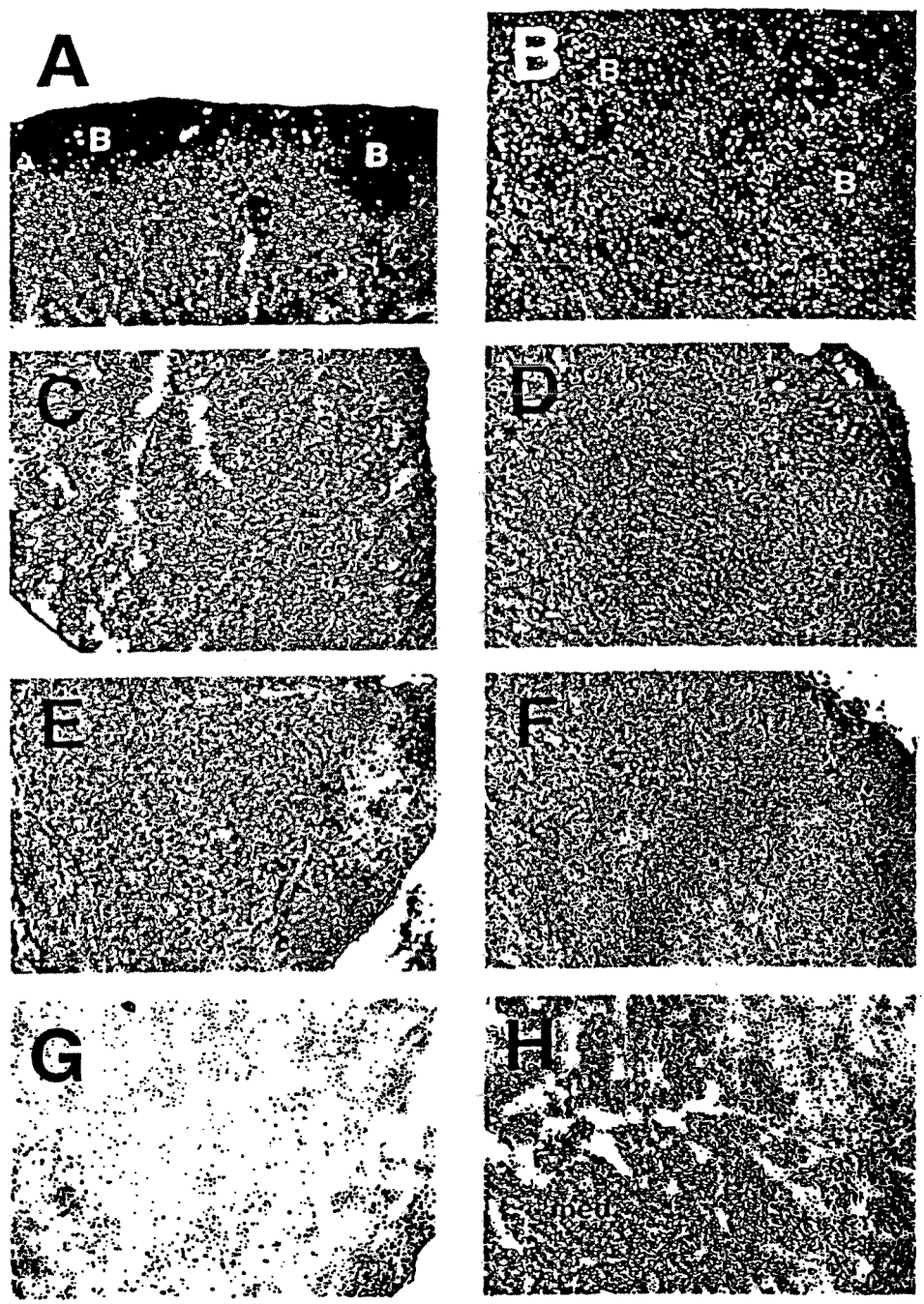

FIG. 13 depicts disrupted T and B cells organization, intense germinal center reactions and large number of plasma cells in the M of BAFF Tg mice.

The control mouse is shown in A, C, E and G and the BAFF Tg mouse is shown in B, D, F, and H. The immunohistochemistry was performed as described in FIG. 6. T and B cell staining is shown in A and B, germinal centers in C and D, dendritic cells E and F and plasma cells in G and H. GC: germinal center. Magnification 100×.

FIG. 14 depicts enlarged and inflamed salivary glands in BAFF Tg mice. (A) Mice 15-17 months old, 4 control littermates (white bar) and 4 BAFF Tg mice (grey bar) were sacrificed the same day for organ collection. Both right and left submaxillary glands were collected and weighted. The data shows the mean±standard deviation of weight for both glands. These results are representative of at least 4 separate groups of age-matched animals dissected. (B) Paraffin sections of submaxillary glands from a control littermate (left panel) and two BAFF Tg mice (middle and right panel) were stained with H&E. Arrows indicate ducts and acinar cells in the left and right panels. The arrow in the middle panel is showing acinar destruction. White stars indicate periductal infiltrates (foci). Magnification 100×. (C) Paraffin sections of submaxillary glands from 7 control mice and 22 BAFF Tg mice (age 12-17 months) were prepared as shown in (B) and scored for the disease as described in materials and methods. The mean score of disease is indicated with a bar. * $p<0.05$, ** $p<0.03$.

Figure 15:
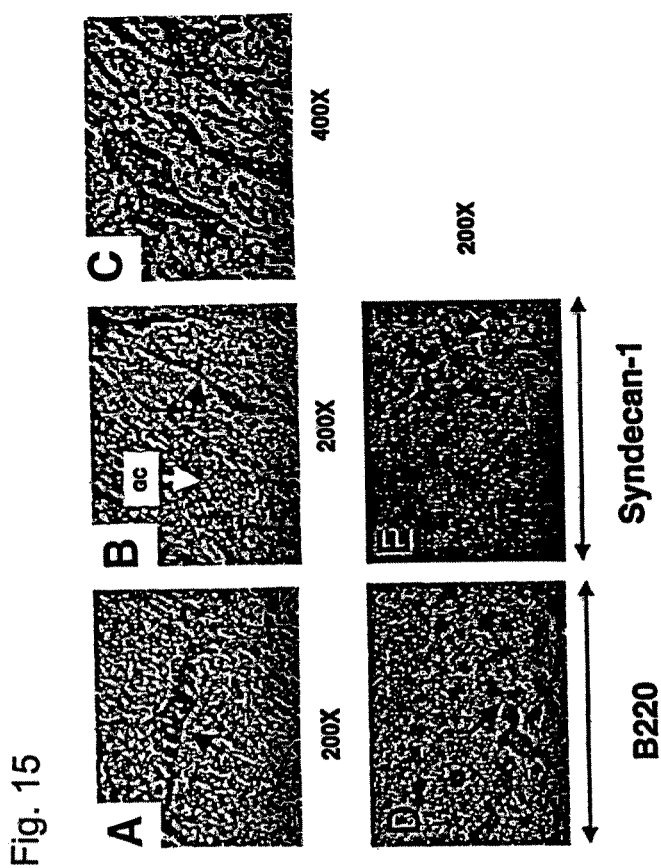

FIG. 15 depicts tumor-like clusters of B-lymphoid cells in a submaxillary tumor or infiltrates present in submaxillary glands of BAFF Tg mice. Frozen sections of submaxillary glands (A and C) or a submaxillary tumor (B, D and E) were stained with H&E (A, B and C) or Biotin-labelled anti-mouse B220 (D) or anti-mouse syndecan-1 (E), followed by Streptavidin-HRP (brown staining in D and E). Arrows in A, B, C and D indicate the tumor-like clusters, arrow in E shows the presence of syndecan-1 positive plasma cells whereas the stars indicate the location of tumor-like clusters. Note that tumor-like clusters and plasma cells do not colocalize. Panels (A) and (C) are representative of 4 animals in which these clusters were detected as cells infiltrating submaxillary glands. Panels (B), (D) and (E) are representative of 3 submaxillary tumors analysed. Magnification is indicated for each panel. A germinal center (GC) is also indicated in panel (B).

FIG. 16 depicts identification of a MZ-like B cell population infiltrating salivary glands of BAFF Tg mice. Submaxillary glands from 13-17 months old BAFF Tg mice and age-matched control littermates were digested with collagenase for purification of infiltrating lymphocytes as described in materials and methods. Using four-color flow cytometry analysis, cells were stained with anti-B220, anti-CD5, anti-IgM and anti-D43. (A) shows the gating on $B220^{hi}$ and $B220^{lo/int}$ B cells on control (left) and BAFF Tg mice (right) as indicated. (B) shows four dot plots for expression of IgM and CD5 on $B220^{hi}$ cells (left) and $B220^{lo/int}$ (right) from BAFF Tg mice and control mice as indicated. The $IgM^{hi}$ B cell gate on $B220^{hi}$ cells (left) and the B-1a and B-1b gates on $B220^{lo/int}$ cells are shown. (C) shows histograms for the expression of CD43 on gated $IgM^{hi}/B220^{hi}$ cells (left) and gated B-1a and B-1b cells (right) from BAFF Tg mice as indicated. (D) Lymphocytes prepared from submaxillary glands (left panel) and inguinal lymph nodes (right panel) of a BAFF Tg mouse were stained with anti-B220, anti-IgM and anti-L-selectin, using a four-color flow cytometry procedure. Cells from submaxillary glands were gated on $B220^{hi}/IgM^{hi}$ (left panel) and on $IgM^+$ (right panel). A histogram of L-selectin expression is shown in each panel. (E) Lymphocytes from a BAFF Tg mice (right) and a control littermate (left) were prepared as in A and stained with anti-B220, anti-IgM and either anti-IgD, anti-CD23, anti-CD21, anti-CD1, anti-HSA, using a three color flow cytometry procedure. Cells were gated on $B220^{hi}$ and $IgM^{hi}$ cells as indicated on the top histograms and expression of IgD, CD23, CD1, CD21 and HSA on these gated cells is shown on histograms for control (left) and Tg mice (right) as indicated. In (C), (D) and A), mean of fluorescence intensity (MFI) and a bar delineating the area in which the negative control histogram is located are indicated in each histogram. (F) Schematic representation of the common and distinct markers expressed on MZ (right circle), B-1 (left circle) and T1 B cells (lower circle). The phenotype of the B cells infiltrating submaxillary glands of BAFF Tg mice is indicated by an oval with a dotted line. These results are representative of at least 12 BAFF Tg and 7 control mice analysed.

Figure 17:
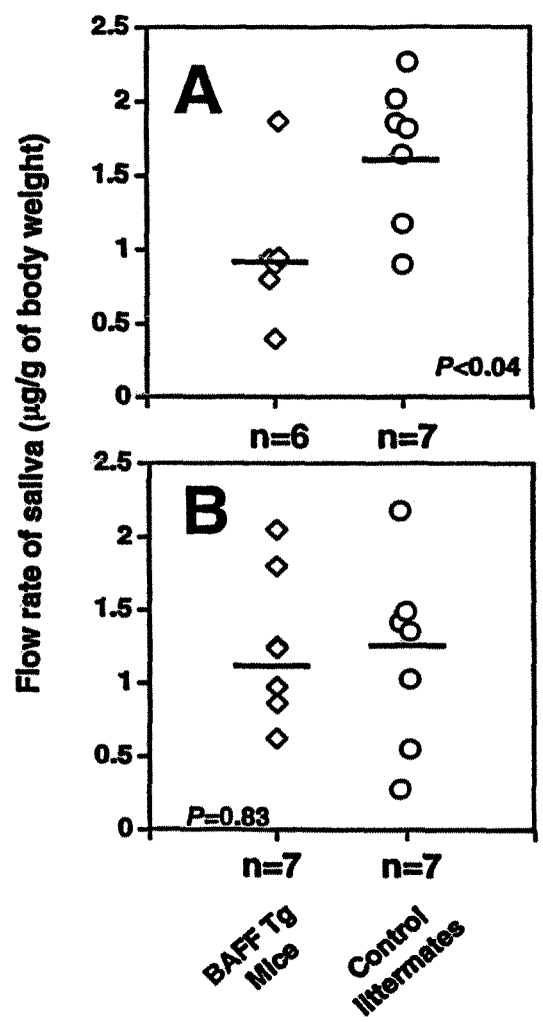

FIG. 17 depicts decreased saliva flow in older BAFF Tg mice. 13 BAFF Tg mice (diamonds) and 14 control littermates (circles) were injected with pilocarpine prior to saliva collection as described in materials and methods. Mice 13-15.5 months old are shown in (A) and mice 8-10 months old are shown in (B). Means of saliva flow are shown with a bar and p values are indicated in each panel.

FIG. 18 depicts elevated levels of BAFF in sera and salivary gland tissues from patients suffering from primary SS but lack of correlation of these levels with levels of total IgG, RF and presence of anti-Ro/a autoantibodies. (A) individual BAFF levels in 39 healthy controls (square), 41 patients with primary SS (diamond), 53 patients with SLE (circle) and 53 patients with RA (triangle) were measured in sera by ELISA and BAFF levels plotted on a log scale. Controls were drawn from normal healthy donors. The horizontal black bars indicates the average for each group: normal 10.4±13 (ng/ml), SS patients 53±67 (ng/ml), SLE patients 12.7±24.4 (ng/ml) and RA patients 23±147 (ng/ml). Some individuals did not have detectable amount of BAFF in their serum and do not appear on the log scale, this includes 16 normals, 6 SS, 20 SLE and 10 RA patients. The dotted line delineates the range of normal BAFF levels. * $p<0.04$, the p value was determined by ANOVA t test. (B) and (C) show the correlation of BAFF levels in the sera of patients with SS with the corresponding levels of IgG (B) and RF (C) in each serum r and p values calculated by ANOVA are shown. (D) shows the levels of BAFF in patients with detected anti-Ro and anti-La (left), anti-Ro only (middle) or no precipitin detected (right). (E) Paraffin sections of a human labial salivary gland biopsy from a patient with SS were stained with a rat anti-human BAFF antibody (right) or an isotype-matched control antibody (left). Staining of normal human labial salivary gland with rat anti-human BAFF antibody is also shown (bottom left, magnification 100×). The staining was revealed using biotin-labeled anti-rat Ig followed by Streptavidin-HRP. The staining a brown on the sections. Magnification 200×. These pictures are representative of 4 patients with primary SS and 3 control tissues analysed.

DETAILED DESCRIPTION OF THE INVENTION

Reference will now be made in detail to the present preferred embodiments of the invention. This invention relates to the use of BAFF and BAFF related molecules to effect the growth and maturation of B-cells and the secretion of immunoglobulin. The invention relates to the use of BAFF and BAFF related molecules to effect responses of the immune system, as necessitated by immune-related disorders. Additionally, this invention encompasses the treatment of cancer and immune disorders through the use of a BAFF, BAFF blocking agents, or BAFF related gene through gene therapy methods.

The BAFF ligand and homologs thereof produced by hosts transformed with the sequences of the invention, as well as native BAFF purified by the processes known in the art, or produced from known amino acid sequences, are useful in a variety of methods for anticancer, antitumor and immunoregulatory applications. They are also useful in therapy and methods directed to other diseases.

"BAFF blocking agents" refers to agents that can diminish BAFF ligand binding to BAFF receptors, or can diminish BAFF receptor signalling, or, that can influence how the BAFF receptor signal is interpreted within the cell.

A BAFF blocking agent that acts by diminishing ligand-receptor binding can inhibit BAFF ligand binding by at least 20%. Examples of BAFF blocking agents include soluble BAFF receptor-Fc molecules, anti-BAFF ligand antibodies and anti-BAFF receptor antibodies.

"BAFF receptors" have been identified and characterized and include TACI (see, e.g., U.S. Pat. No. 5,969,102 and WO98/39361, incorporated herein by reference), BCMA (see, e.g., WO01/12812, incorporated herein by reference), and BAFFR (e.g., GenBank™ accession No. AF373846 for human BAFF-R (SEQ ID NO:27) and accession No. AF373847 for murine BAFF-R (SEQ ID NO:28); see, also, e.g., Thompson et al. (2001) Science 293:2108, incorporated herein by reference).

Another aspect of the invention relates to the use of the polypeptide encoded by the isolated nucleic acid encoding the BAFF-ligand in "antisense" therapy. As used herein, "antisense" therapy refers to administration or in situ generation of oligonucleotides or their derivatives which specifically hybridize under cellular conditions with the cellular mRNA and/or DNA encoding the ligand of interest, so as to inhibit expression of the encoded protein, i.e. by inhibiting transcription and/or translation. The binding may be by conventional base pair complementarity, or, for example, in the case of binding to DNA duplexes, through specific interactions in the major groove of the double helix. In general, "antisense" therapy refers to a range of techniques generally employed in the art, and includes any therapy which relies on specific binding to oligonucleotide sequences.

An antisense construct of the present invention can be delivered, for example, as an expression plasmid, which, when transcribed in the cell, produces RNA which is complementary to at least a portion of the cellular mRNA which encodes Kay-ligand. Alternatively, the antisense construct can be an oligonucleotide probe which is generated ex vivo. Such oligonucleotide probes are preferably modified oligonucleotides which are resistant to endogenous nucleases, and are therefor stable in vivo. Exemplary nucleic acids molecules for use as antisense oligonucleotides are phosphoramidates, phosphothioate and methylphosphonate analogs of DNA (See, e.g., U.S. Pat. No. 5,176,996; U.S. Pat. No. 5,264,564; and U.S. Pat. No. 5,256,775). Additionally, general approaches to constructing oligomers useful in antisense therapy have been reviewed, for example, by Van Der Krol et al., (1988) *Biotechniques* 6:958-976; and Stein et al. (1988) *Cancer Res* 48: 2659-2668, specifically incorporated herein by reference.

A. BAFF-Ligand

The BAFF-ligand of the invention, as discussed above, is a member of the TNF family and is described in PCT application number PCT/US98/19037 (WO99/12964) and is incorporated in its entirety herein. The protein, fragments or homologs thereof may have wide therapeutic and diagnostic applications.

The BAFF-ligand is present primarily in the spleen and in peripheral blood lymphocytes, strongly indicating a regulatory role in the immune system. Comparison of the claimed BAFF-ligand sequences with other members of the human TNF family reveals considerable structural similarity. All the proteins share several regions of sequence conservation in the extracellular domain.

Although the precise three-dimensional structure of the claimed ligand is not known, it is predicted that, as a member of the TNF family, it may share certain structural characteristics with other members of the family.

The novel polypeptides of the invention specifically interact with a receptor, which has not yet been identified. However, the peptides and methods disclosed herein enable the identification of receptors which specifically interact with the BAFF-ligand or fragments thereof.

The claimed invention in certain embodiments includes methods of using peptides derived from BAFF-ligand which have the ability to bind to their receptors. Fragments of the BAFF-ligands can be produced in several ways, e.g., recombinantly, by PCR, proteolytic digestion or by chemical synthesis. Internal or terminal fragments of a polypeptide can be generated by removing one or more nucleotides from one end or both ends of a nucleic acid which encodes the polypeptide. Expression of the mutagenized DNA produces polypeptide fragments.

Polypeptide fragments can also be chemically synthesized using techniques known in the art such as conventional Merrifield solid phase f-moc or t-boc-chemistry. For example, peptides and DNA sequences of the present invention may be arbitrarily divided into fragments of desired length with no overlap of the fragment, or divided into overlapping fragments of a desired length. Methods such as these are described in more detail below.

B. Generation of Soluble Forms of BAFF-Ligand and BAFF-Receptors

Soluble forms of the BAFF-ligand can often signal effectively and hence can be administered as a drug which now mimics the natural membrane form. It is possible that the BAFF-ligand claimed herein are naturally secreted as soluble cytokines, however, if not, one can reengineer the gene to force secretion. To create a soluble secreted form of BAFF-ligand or BAFF receptor, one would remove at the DNA level the N-terminus transmembrane regions, and some portion of the stalk region, and replace them with a type I leader or alternatively a type II leader sequence that will allow efficient proteolytic cleavage in the chosen expression system. A skilled artisan could vary the amount of the stalk region retained in the secretion expression construct to optimize both receptor binding properties and secretion efficiency. For example, the constructs containing all possible stalk lengths, i.e. N-terminal truncations, could be prepared such that proteins starting at amino acids 81 to 139 would result. The optimal length stalk sequence would result from this type of analysis.

Soluble forms of BAFF receptors can be prepared using techniques well-known to those of ordinary skill in the art. Immunoglobulin Fc portions may be fused to the BAFF receptor protein to increase the half-life of the soluble BAFF receptor. Production of such soluble BAFF receptor proteins is described, for example, in WO 01/12812, WO 01/24811, and PCT/US01/40626, the entire disclosures of which are incorporated herein by reference.

C. Generation of Antibodies Reactive with the BAFF-Ligand and BAFF Receptors

The invention also includes antibodies specifically reactive with the claimed BAFF-ligand or its receptors. Anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal such as a mouse, a hamster or rabbit can be immunized with an immunogenic form of the peptide. Techniques for conferring immunogenicity on a protein or peptide include conjugation to carriers, or other techniques, well known in the art.

An immunogenic portion of BAFF-ligand or its receptors can be administered in the presence of an adjuvant. The progress of immunization can be monitored by detection of antibody titers in plasma or serum. Standard ELISA or other immunoassays can be used with the immunogen as antigen to assess the levels of antibodies.

In a preferred embodiment, the subject antibodies are immunospecific for antigenic determinants of BAFF-ligand or its receptors, (e.g. antigenic determinants of a polypeptide of SEQ. ID. NO.: 2, said sequence as described in PCT application number PCT/US98/19037 (WO99/12964) and is incorporated in its entirety herewith), or a closely related human or non-human mammalian homolog (e.g. 70, 80 or 90 percent homologous, more preferably at least 95 percent homologous). In yet a further preferred embodiment of the present invention, the anti-BAFF-ligand or anti-BAFF-ligand-receptor antibodies do not substantially cross react (i.e. react specifically) with a protein which is e.g., less than 80 percent homologous to SEQ. ID. NO.: 2 or 6 said sequence as described in PCT application number PCT/US98/19037 (WO99/12964) and is incorporated in its entirety herewith; preferably less than 90 percent homologous with SEQ. ID. NO.: 2 said sequence as described in PCT application number PCT/US98/19037 (WO99/12964) and is incorporated in its entirety herewith; and, most preferably less than 95 percent homologous with SEQ. ID. NO.: 2 said sequence as described in PCT application number PCT/US98/19037 (WO99/12964) and is incorporated in its entirety herewith. By "not substantially cross react", it is meant that the antibody has a binding affinity for a non-homologous protein which is less than 10 percent, more preferably less than 5 percent, and even more preferably less than 1 percent, of the binding affinity for a protein of SEQ. ID. NO.: 2 said sequence as described in PCT application number PCT/US98/19037 (WO99/12964) and is incorporated in its entirety herewith.

Production of exemplary anti-BAFF receptor antibodies is described, for example, in WO 01/12812, WO 01/24811 and PCT/US01/40626, the entire disclosures of which are incorporated herein by reference.

The term antibody as used herein is intended to include fragments thereof which are also specifically reactive with BAFF-ligand, or its receptors. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibodies of the present invention are further intended to include biospecific and chimeric molecules having anti-BAFF-ligand or anti-BAFF-ligand-receptor activity. Thus, both, monoclonal and polyclonal antibodies (Ab) directed against BAFF-ligand, Tumor-ligand and their receptors, and antibody fragments such as Fab' and F(ab')$_2$, can be used to block the action of the Ligand and their respective receptor.

Various forms of antibodies can also be made using standard recombinant DNA techniques. Winter and Milstein (1991) *Nature* 349: 293-299, specifically incorporated by reference herein. For example, chimeric antibodies can be constructed in which the antigen binding domain from an animal antibody is linked to a human constant domain (e.g. Cabilly et al., U.S. Pat. No. 4,816,567, incorporated herein by reference). Chimeric antibodies may reduce the observed immunogenic responses elicited by animal antibodies when used in human clinical treatments.

In addition, recombinant "humanized antibodies" which recognize BAFF-ligand or its receptors can be synthesized. Humanized antibodies are chimeras comprising mostly human IgG sequences into which the regions responsible for specific antigen-binding have been inserted. Animals are immunized with the desired antigen, the corresponding antibodies are isolated, and the portion of the variable region sequences responsible for specific antigen binding are removed. The animal-derived antigen binding regions are then cloned into the appropriate position of human antibody genes in which the antigen binding regions have been deleted. Humanized antibodies minimize the use of heterologous (i.e. inter species) sequences in human antibodies, and thus are less likely to elicit immune responses in the treated subject.

Construction of different classes of recombinant antibodies can also be accomplished by making chimeric or humanized antibodies comprising variable domains and human constant domains (CH1, CH2, CH3) isolated from different classes of immunoglobulins. For example, antibodies with increased antigen binding site valencies can be recombinantly produced by cloning the antigen binding site into vectors carrying the human:chain constant regions. Arulanandam et al. (1993) *J. Exp. Med.*, 177: 1439-1450, incorporated herein by reference.

In addition, standard recombinant DNA techniques can be used to alter the binding affinities of recombinant antibodies with their antigens by altering amino acid residues in the vicinity of the antigen binding sites. The antigen binding affinity of a humanized antibody can be increased by mutagenesis based on molecular modeling. Queen et al., (1989) *Proc. Natl. Acad. Sci.* 86: 10029-33 incorporated herein by reference.

D. Generation of Analogs: Production of Altered DNA and Peptide Sequences

Analogs of the BAFF-ligand can differ from the naturally occurring BAFF-ligand in amino acid sequence, or in ways that do not involve sequence, or both. Non-sequence modifications include in vivo or in vitro chemical derivatization of the BAFF-ligand. Non-sequence modifications include, but are not limited to, changes in acetylation, methylation, phosphorylation, carboxylation or glycosylation.

Preferred analogs include BAFF-ligand biologically active fragments thereof, whose sequences differ from the sequence given in SEQ. ID NO. 2 said sequence as described in PCT application number PCT/US98/19037 (WO99/12964) and is incorporated in its entirety herewith, by one or more conservative amino acid substitutions, or by one or more non-conservative amino acid substitutions, deletions or insertions which do not abolish the activity of BAFF-ligand. Conservative substitutions typically include the substitution of one amino acid for another with similar characteristics, e.g. substitutions within the following groups: valine, glycine; glycine, alanine; valine, isoleucine, leucine; aspartic acid, glutamic acid; asparagine, glutamine; serine, threonine; lysine, arginine; and, phenylalanine, tyrosine.

E. Materials and Methods of the Invention

The anti-Flag M2 monoclonal antibody, biotinylated anti-Flag M2 antibody and the anti-Flag M2 antibody coupled to agarose were purchased from Sigma Cell culture reagents were obtained from Life Sciences (Basel, Switzerland) and Biowhittaker (Walkersville, Md.). Flag-tagged soluble human APRIL (residues $K_{110}$-$L_{250}$) was produced in 293 cells as described (10, 11). FITC-labeled anti-CD4, anti-CD8 and anti-CD19 antibodies were purchased from Pharmingen (San Diego, Calif.). Goat F(ab')$_2$ specific for the $Fc_{5\mu}$ fragment of human IgM were purchased from Jackson ImmunoResearch (West Grove, Pa.). Secondary antibodies were obtained from either Pharmingen or from Jackson ImmunoResearch and used at the recommended dilutions.

Human embryonic kidney 293 T (12) cells and fibroblast cell lines (Table 1) were maintained in DMEM containing 10% heat-inactivated fetal calf serum (FCS). Human embryonic kidney 293 cells were maintained in DMEM-nutrient mix F12 (1:1) supplemented with 2% FCS. T cell lines, B cell lines, and macrophage cell lines (Table 1) were grown in RPMI supplemented with 10% FCS. Molt-4 cells were cultivated in Iscove's medium supplemented with 10% FCS. Epithelial cell lines were grown in MEM-alpha medium containing 10% FCS, 0.5 mM non-essential amino acids, 10 mM Na-Hepes and 1 mM Na pyruvate. HUVECs were maintained in M199 medium supplemented with 20% YCS, 100 µg/ml of epithelial cell growth factor (Collaborative Research, Inotech, Dottikon, Switzerland) and 100 µg/ml of heparin sodium salt (Sigma). All media contained penicillin and streptomycin antibiotics. Peripheral blood leukocytes were isolated from heparinized blood of healthy adult volunteers by Ficoll-Paque (Pharmacia, Uppsala, Sweden) gradient centrifugation and cultured in RPMI, 10% FCS.

T cells were obtained from non-adherents PBLs by rosetting with neuraminidase-treated sheep red blood cells and separated from non-rosetting cells (mostly B cells and monocytes) by Ficoll-Paque gradient centrifugation. Purified T cells were activated for 24 h with phytohemagglutinin (Sigma) (1 µg/ml), washed and cultured in RPMI, 10% FCS, 20 U/ml of IL-2. CD14$^+$ monocytes were purified by magnetic cell sorting using anti-CD14 antibodies, goat anti-mouse-coated microbeads and a Minimac™ device (Miltenyi Biotech), and cultivated in the presence of GM-CSF (800 U/ml, Leucomax®, Essex Chemie, Luzern, Switzerland) and IL-4 (20 ng/ml, Lucerna Chem, Luzern, Switzerland) for 5 d, then with GM-CSF, IL-4 and TNFα(200 U/ml, Bender, Vienna, Austria) for an additional 3 d to obtain a CD83$^+$, dentritic cell-like population. Human B cells of >97% purity were isolated from peripheral blood or umbilical cord blood using anti-CD19 magnetic beads (M450, Dynal, Oslo, Norway) as described (13).

Northern Blot Analysis

Northern blot analysis was carried out using Human Multiple Tissue Northern Blots I and II (Clontech #7760-1 and #7759-1). The membranes were incubated in hybridization solution (50% formamide, 2.5×Denhardt's, 0.2% SDS, 10 mM EDTA, 2×SSC, 50 mM NaH$_2$PO$_4$, pH 6.5, 200 µg/ml sonicated salmon sperm DNA) for 2 h at 60° C. Antisense RNA probe containing the nucleotides corresponding to amino acids 136-285 of hBAFF was heat-denatured and added at 2×10$^6$ cpm/ml in fresh hybridization solution. The membrane was hybridized 16 h at 62° C., washed once in 2×SSC, 0.05% SDS (30 min at 25° C.), once in 0.1×SSC, 0.1% SDS (20 min at 65° C.) and exposed at −70° C. to X-ray films.

Characterization of BAFF cDNA

A partial sequence of human BAFF cDNA was contained in several EST clones—(e.g., GenBank Accession numbers T87299 and AA166695) derived from fetal liver and spleen and ovarian cancer libraries. The 5' portion of the cDNA was obtained by 5'-RACE-PCR (Marathon-Ready cDNA, Clonetech, Palo Alto, Calif.) amplification with oligonucleotides AP1 and JT1013 (5'-ACTGTTTCTTCTGGACCCT-GAACGGC-3') [SEQ ID. NO.: 9] using the provided cDNA library from a pool of human leukocytes as template, as recommended by the manufacturer. The resulting PCR product was cloned into PCRA) blunt (Invitrogen, NV Leek, The Netherlands) and subcloned as EcoRI/PstI fragment into pT7T3-Pac vector (Pharmacia) containing EST clone T87299. Full-length hBAFF cDNA was therefore obtained by combining 5' and 3' fragments using the internal PstI site of BAFF. Sequence has been assigned GenBank accession number AF116456.

A partial 617 bp sequence of murine BAFF was contained in two overlapping EST clones (AA422749 and AA254047). A PCR fragment spanning nucleotides 158 to 391 of this sequence was used as a probe to screen a mouse spleen cDNA library (Stratagene, La Jolla, Calif.).

Expression of Recombinant BAFF

Full length hBAFF was amplified using oligos JT1069 (5'-GACAAGCTTGCCACCATGGATGACTCCACA-3') [SEQ. ID. NO.: 10] and JT637 (5'-ACTAGTCACAGCAGTTTCAATGC-3') [SEQ. ID. NO.: 11]. The PCR product was cloned into PCR-0 blunt and re-subcloned as HindIII/EcoRI fragment into PCR-3 mammalian expression vector. A short version of soluble BAFF (amino acids Q136-L285) was amplified using oligos JT636 (5'-CTGCAGGGTCCAGAAGAAACAG-3') [SEQ. ID. NO.: 12] and JT637. A long version of soluble BAFF (aa L83-L285) was obtained from full length BAFF using internal PstI site. Soluble BAFFs were resubcloned as PstI/EcoRI fragments behind the haemaglutinin signal peptide and Flag sequence of a modified PCR-3 vector, and as PstI/SpeI fragments into a modified pQE16 bacterial expression vector in frame with a N-terminal Flag sequence (14). Constructs were sequenced on both strands. The establishment of stable 293 cell lines expressing the short soluble form or full length BAFF, and the expression and purification of recombinant soluble BAFF from bacteria and mammalian 293 cells was performed as described (14, 15).

Reverse Transcriptase PCR

Total RNA extracted from T cells, B cells, in vitro derived immature dendritic cells, 293 wt and 293-BAFF (full length) cells was reverse transcribed using the Ready to Go system (Pharmacia) according to the manufacturer's instructions. BAFF and β-actin cDNAs were detected by PCR amplification with Taq DNA polymerase (steps of 1 min each at 94° C., 55° C. and 72° C. for 30 cycles) using specific oligonucleotides: for BAFF, JT1322 5'-GGAGAAGGCAACTCCAGTCAGAAC-3' [SEQ. ID. NO.: 13] and JT1323 5'-CAATTCATCCCCAAAGACATGGAC-3' [SEQ. ID. NO.: 14]; for IL-2 receptor alpha chain, JT1368 5'-TCGGAACACAACGAAACAAGTC-3' [SEQ. ID. NO.: 15] and JT1369 5'-CTTCTCCTTCACCTGGAAACTGACTG-3' [SEQ. ID NO.: 16]; for β-actin, 5'-GGCATCGTGATGGACTCCG-3' [SEQ. ID. NO.: 17] and 5'-GGAAGGTGGACAGCGA-3' [SEQ. ID. NO.: 18].

Gel Permeation Chromatography 293T cells were transiently transfected with the short form of soluble BAFF and grown in serum-free Optimem medium for 7 d. Conditioned supernatants were concentrated 20×, mixed with internal standards catalase and ovalbumin, and loaded onto a Superdex-200 HR10/30 column. Proteins were eluted in PBS at 0.5 ml/min and fractions (0.25 ml) were precipitated with trichloroacetic acid and analyzed by Western blotting using anti-Flag M2 antibody. The column was calibrated with standard proteins: ferritin (440 kDa), catalase (232 kDa), aldolase (158 kDa), bovine serum albumine (67 kDa), ovalbumine (43 kDa), chymotrypsinogen A (25 kDa) and ribonuclease A (13.7 kDa).

PNGase, F Treatment

Samples were heated in 20 μl of 0.5% SDS, 1% 2-mercaptoethanol for 3 min at 95° C., then cooled and supplemented with 10% Nonidet P40 (2 μl), 0.5 M sodium phosphate, pH 7.5 (2 μl) and Peptide N-glycanase F (125 units/μl, 1 μl, or no enzyme in controls). Samples were incubated for 3 h at 37° C. prior to analysis by Western blotting.

EDMAN Sequencing

293 T cells were transiently transfected, with the long form of soluble BAFF and grown in serum-free Optimem medium for 7 d. Conditioned supernatants were concentrated 20×, fractionated by SDS-PAGE and blotted onto polyvinylidene difluoride membrane (BioRad Labs, Hercules, Calif.) as previously described (16), and then sequenced using a gas phase sequencer (ABI 120A, Perkin Elmer, Foster City, Calif.) coupled to an analyzer (ABI 120A, Perkin Elmer) equipped with a phenylthiohydantoin C18 2.1×250 mm column. Data was analyzed using software ABI 610 (Perkin Elmer).

Antibodies

Polyclonal antibodies were generated by immunizing rabbits (Eurogentec, Seraing, Belgium) with recombinant soluble BAFF. Spleen of rats immunized with the same antigen were fused to x63Ag8.653 mouse myeloma cells, and hybridoma were screened for BAFF-specific IgGs. One of these monoclonal antibodies, 43.9, is an IgG2a that specifically recognizes hBAFF.

Cells were stained in 50 μl of FACS buffer (PBS, 10% FCS, 0.02% $NaN_3$) with 50 ng (or the indicated amount) of Flag tagged short soluble hBAFF for 20 min at 4° C., followed by anti-Flag M2 (1 μg) and secondary antibody. Anti-BAFF mAb 43.9 was used at 40 μg/ml. For two color FACS analysis, peripheral blood lymphocytes were stained with Flag tagged soluble BAFF/long (2 μg/ml), followed by biotinylated anti-Flag M2 (1/400) and PE-labeled streptavidin (1/100), followed by either FITC-labeled anti-CD4, antiCD8 or anti-CD19.

PBL Proliferation Assay

Peripheral blood leukocytes were incubated in 96-well plates ($10^5$ cells/well in 100 μl RPMI supplemented with 10% FCS) for 72 h in the presence or absence of 2 μg/ml of goat anti-human μ chain antibody (Sigma) or control $F(ab')_2$ and with the indicated concentration of native or boiled soluble BAFF/long. Cells were pulsed for an additional 6 h with [$^3$H]thymidine (1 μCi/well) and harvested. [$^3$H]thymidine incorporation was monitored by liquid scintillation counting. In some experiments, recombinant soluble BAFF was replaced by 293 cells stably transfected with full length BAFF (or 293 wt as control) that had been fixed for 5 min at −25° C. in 1% paraformaldeyde. Assay was performed as described (17). In further experiments, CD19$^+$ cells were isolated form PBL with magnetic beads and the remaining CD19$^-$ cells were irradiated (3000 rads) prior to reconstitution with CD19$^+$ cells. Proliferation assay with sBAFF was then performed as described above.

B Cell Activation Assay

Purified B cells were activated in the EL-4 culture system as described (13). Briefly, $10^4$ B cells mixed with $5 \times 10^4$ irradiated murine EL-4 thymoma cells (clone B5) were cultured for 5-6 d in 200 μl medium containing 5% v/v of culture supernatants from human T cells ($10^6$/ml) which had been activated for 48 h with PHA, (1 μg/ml) and PMA (1 ng/ml). B cells were then reisolated with anti-CD19 beads and cultured for another 7 d ($5 \times 10^4$ cells in 200 μl, duplicate or triplicate culture in flat bottomed 96 well plates) in medium alone or in medium supplemented with 5% T cell supernatants, or with 50 ng/ml IL-2 (a kind gift from the former Glaxo Institute for Molecular Biology, Geneva) and 10 ng/ml each IL-4 and IL-10 (Peprotech, London, UK), in the presence or absence of sBAFF. The anti-Flag M antibody was added at a concentration of 2 μg/ml and had no effect by itself. IgM, IgG and IgA in culture supernatants wee quantitated by ELISA assays as described (13).

Figure 1A:
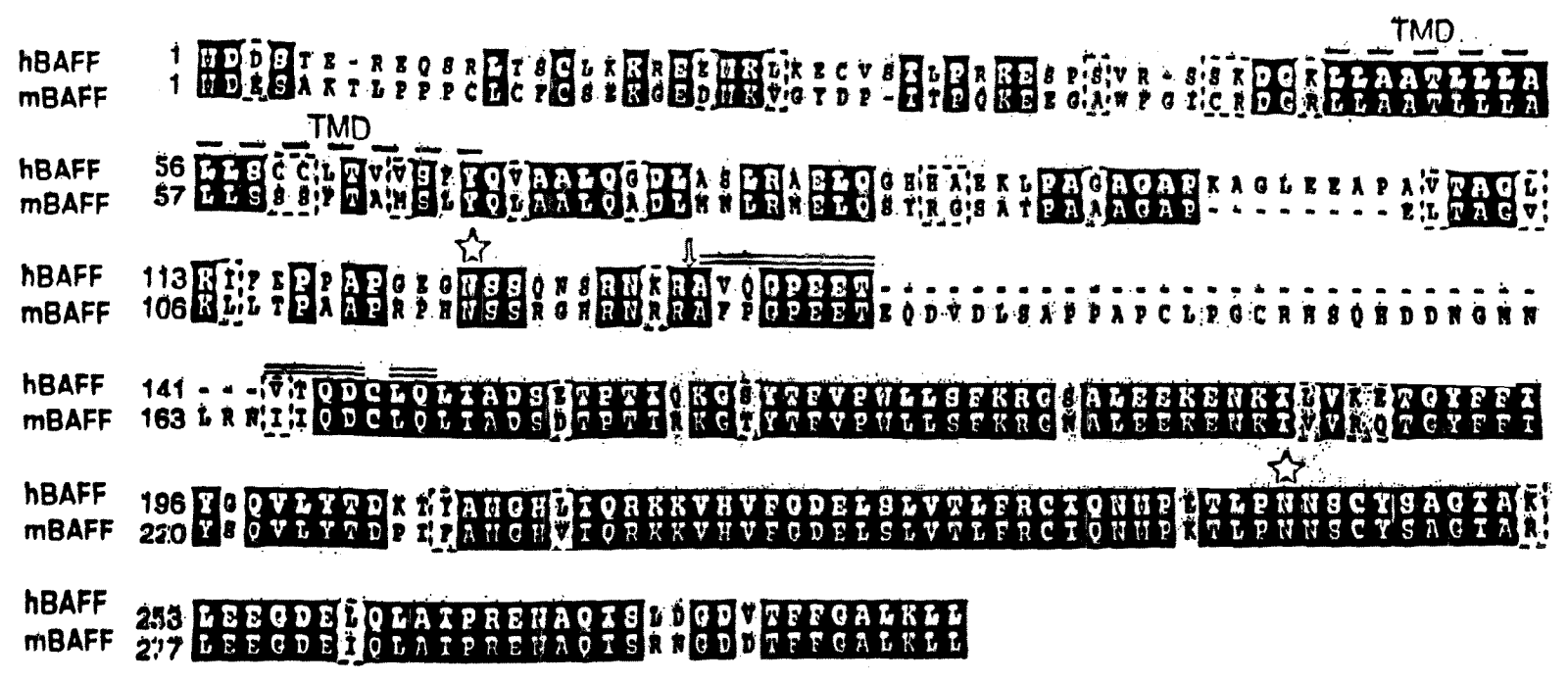
Figure 1B:
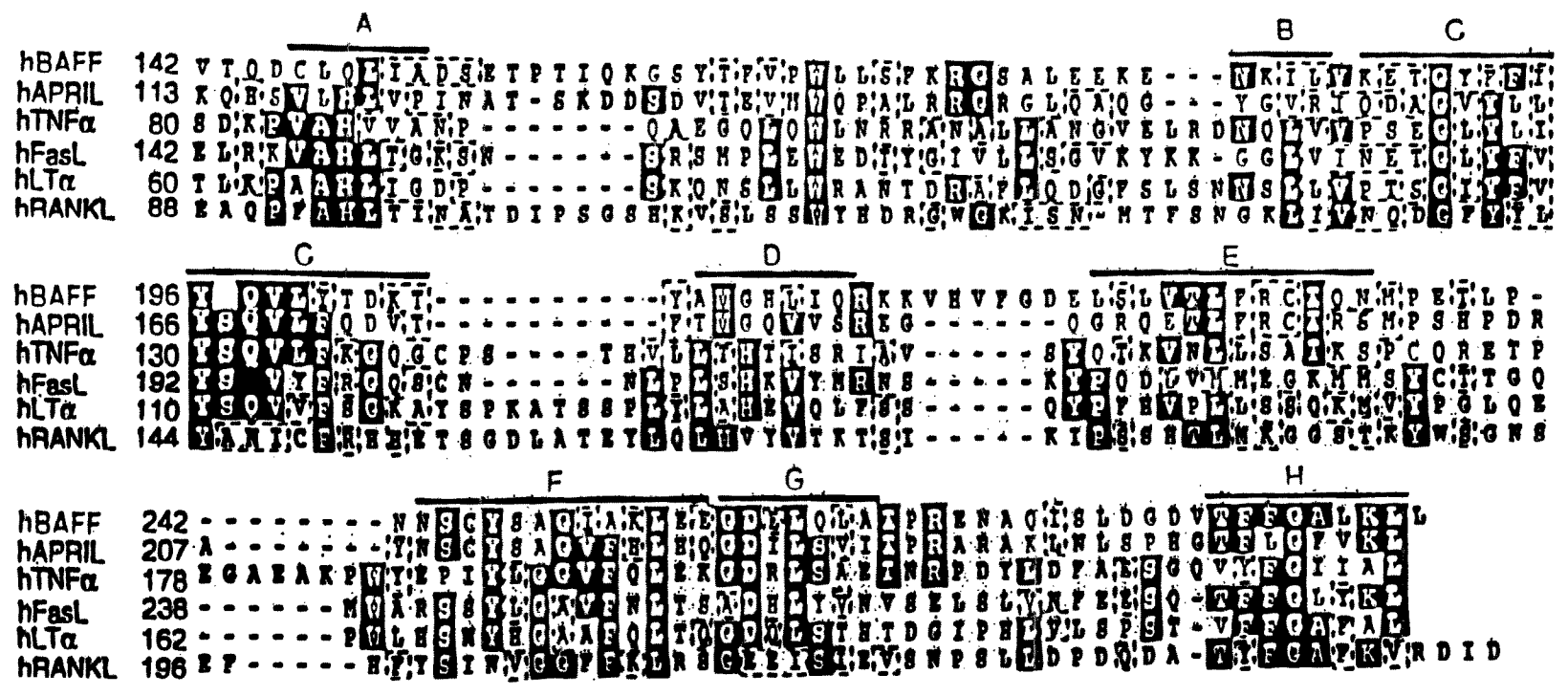
Figure 1C:
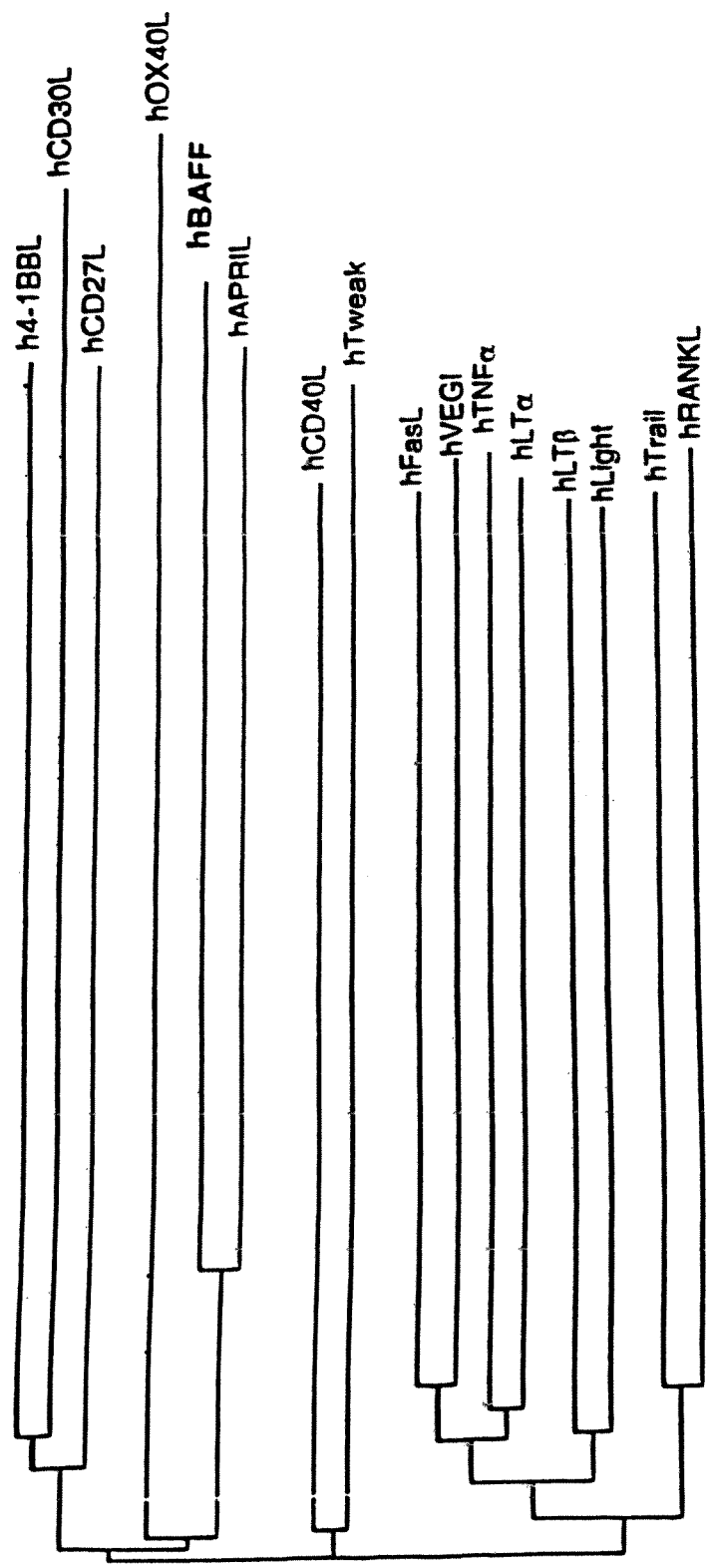
FIG. 1(A) depicts the predicted amino acid sequence of human [SEQ. ID. NO.: 1] and mouse BAFF [SEQ. ID. NO.:2]. The predicted transmembrane domain (TMD, dashed line), the potential N-linked glycosylation sites (stars) and the natural processing site of human BAFF (arrow) are indicated. The double line above hBAFF indicates the sequence obtained by Edman degradation of the processed form of BAFF. (B) Depicts a comparison of the extracellular protein sequence of BAFF [SEQ. ID. NO.: 3] and some members of the TNF ligand family [SEQ. ED. NO.: 4 (hAPRIL); SEQ. ID. NO.: 5 (hTNF alpha); SEQ. ID. NO.: 6 (hFasL); SEQ. ID. NO.: 7 (hLT alpha); SEQ. ID. NO.: 8 (hRANKL)]. Identical and homologous residues are represented in black and shaded boxes, respectively. (C) Depicts dendrogram of TNF family ligands.

Human BAFF was identified by sequence homology as a possible novel member of the TNF ligand family while we screened public databases using an improved profile search (18). A cDNA encoding the complete protein of 285 amino acids (aa) was obtained by combining EST-clones (covering the 3' region) with a fragment (5' region) amplified by PCR. The absence of a signal peptide suggested that BAFF was a type II membrane protein that is typical of the members of the TNF-ligand family. The protein has a predicted cytoplasmic domain of 46 aa, a hydrophobic transmembrane region, and an extracellular domain of 218 aa containing two potential N-glycosylation sites (FIG. 1A). The sequence of the extracellular domain of BAFF shows highest homology with APRIL (33% amino acid identities, 48% homology), whereas the identity with other members of the family such as TNF, FasL, LTα, TRAIL or RANKL is below 20% (FIGS. 1B, C). The mouse BAFF cDNA clone isolated from a spleen library encoded a slightly longer protein (309 aa) due to an insertion between the transmembrane region and the first of several β-strands which constitute the receptor binding domain in all TNF ligand members (19). This β-strand rich ectodomain is almost identical in mouse and human BAFF (86% identity, 93% homology) suggesting that the BAFF gene has been highly conserved during evolution (FIG. 1A).

Figure 2A:
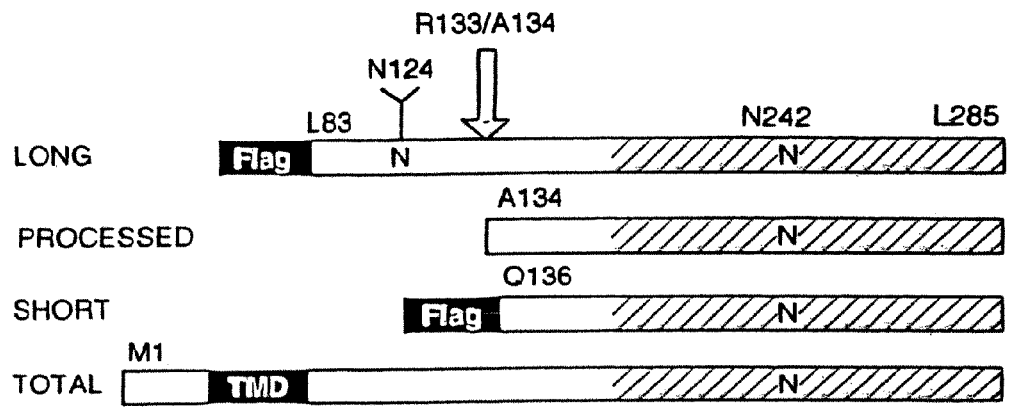
FIG. 2 is a schematic characterization of recombinant BAFF (A) Schematic representation of recombinant BAFF constructs. Soluble recombinant BAFFs starting at $Leu_{83}$ and $Gln_{136}$ are expressed fused to a N-terminal Flag tag and a 6 amino acid linker. The long form is cleaved between $Arg_{133}$ and $Ala_{134}$ (arrow) in 293 T cells, to yield a processed form of BAFF. $Asn_{124}$ and $Asn_{242}$ belong to N-glycosylation consensus sites. N-linked glycan present on $Asn_{124}$ is shown as a Y. TMD: transmembrane domain. (B) Peptide N-glycanase F (PNGase F) treatment of recombinant BAFF.
Figure 2B:
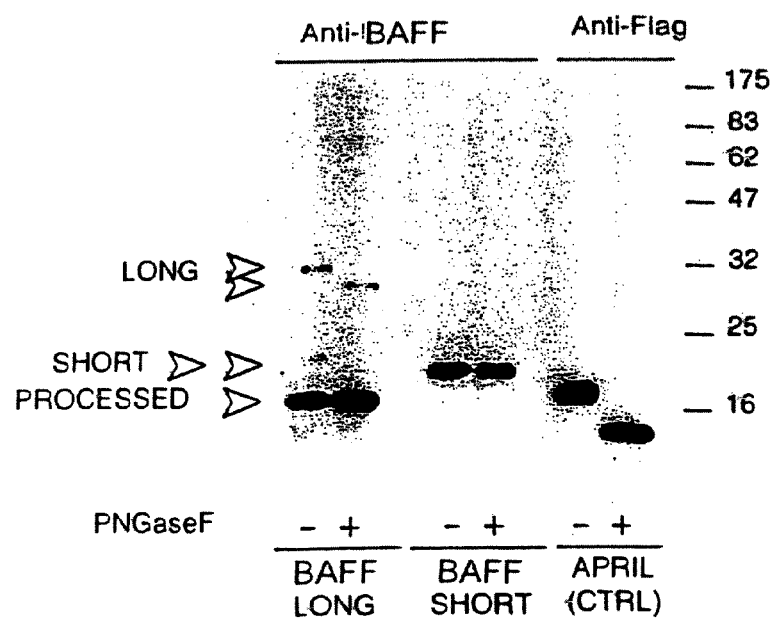
Figure 2C:
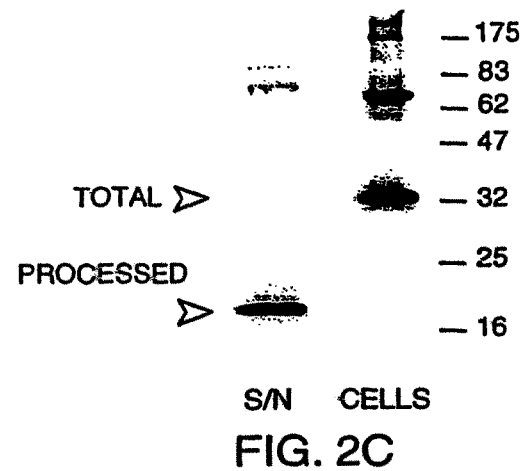

Although TNF family members are synthesized as membrane inserted ligands, cleavage in the stalk region between transmembrane and receptor binding domain is frequently observed. For example, TNF or FasL are readily cleaved from the cell surface by metalloproteinases (20, 21). While producing several forms of recombinant BAFF in 293T cells, we noticed that a recombinant soluble 32 kDa form of BAFF (aa 83-285, sBAFF/long), containing the complete stalk region and a N-terminal Flag-tag in addition to the receptor binding domain, was extensively processed to a smaller 18 kDa fragment (FIGS. 2A, B). Cleavage occurred in the stalk region since the fragment was detectable only with antibodies raised against the complete receptor interaction domain of BAFF but not with anti-Flag antibodies (data not shown). Also revealed was that only N124 (located in the stalk) but not N242 (located at the entry of the F-□ sheet) was glycosylated, since the molecular mass of the non-processed sBAFF/long was reduced from 32 kDa to 30 kDa upon removal of the N-linked carbohydrates with PNGase F whereas the 18 kDa cleaved form was insensitive to this treatment. Peptide sequence analysis of the 18 kDa fragment indeed showed that cleavage occurred between R133 and A134 (FIG. 1A). R133 lies at the end of a polybasic region which is conserved between human (R-N-K-R) and mouse (R-N-R-R). To test whether cleavage was not merely an artifact of expressing soluble, non-natural forms of BAFF, membrane-bound full length BAFF was expressed in 293T cells (FIG. 2C). The 32 kDa complete BAFF and some higher molecular mass species probably corresponding to non-dissociated dimers and trimers) were readily detectable in cellular extracts, but more than 95% of BAFF recovered from the supernatant corresponded to the processed 18 kDa form, indicating that BAFF was also processed when synthesized as a membrane-bound ligand.

Figure 2D:
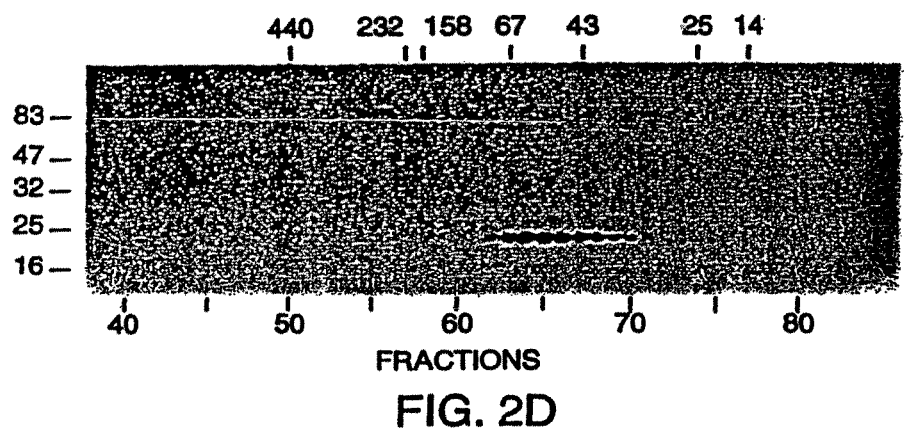

A soluble BAFF was engineered (Q136-L285, sBAFF/short) whose sequence started 2 aa downstream of the processing site (FIG. 1B). As predicted, the Flag-tag attached to the N-terminus of this recombinant molecule was not removed (data not shown) which allowed its purification by an anti-Flag affinity column. To test its correct folding, the purified sBAFF/short was analyzed by gel filtration where the protein eluted at an apparent molecular mass of 55 kDa (FIG. 2D). The sBAFF/short correctly assembles into a homotrimer (3×20 kDa) in agreement with the quaternary structure of other TNF family members (19). Finally, unprocessed sBAFF/long was readily expressed in bacteria, indicating that the cleavage event was specific to eukaryotic cells.

Figure 3A:
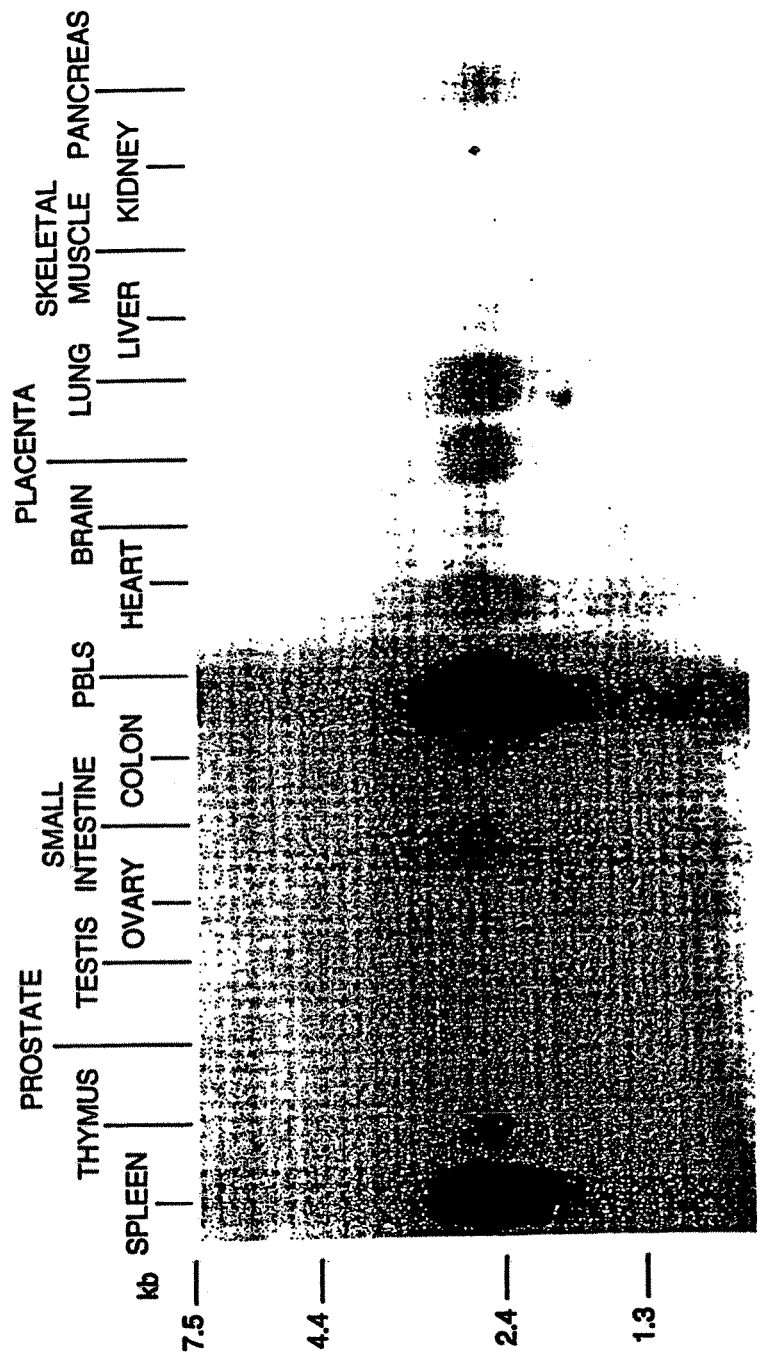
Figure 3B:
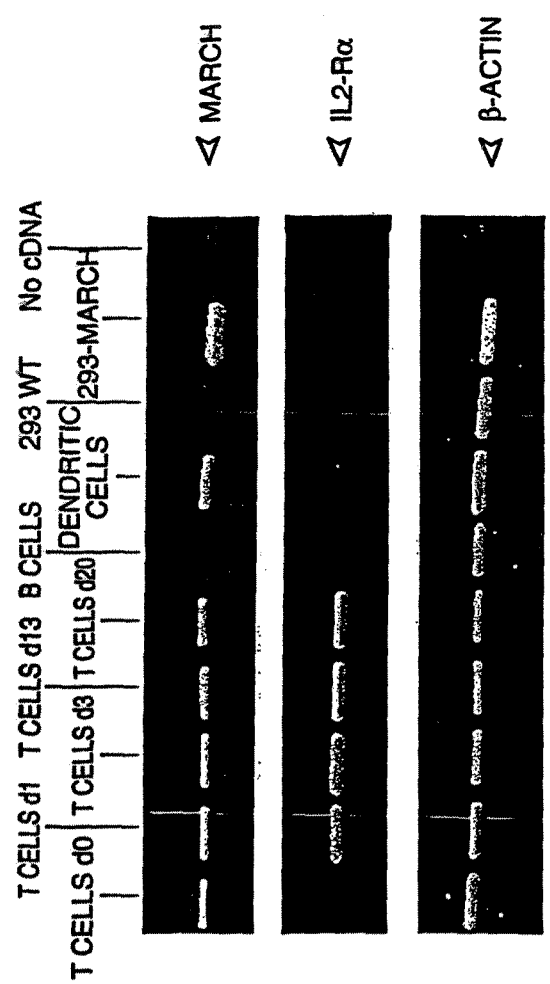

Northern blot analysis of BAFF revealed that the 2.5 kb BAFF mRNA was abundant in the spleen and PBLs (FIG. 3A). Thymus, heart, placenta, small intestine and lung showed weak expression. This restricted distribution suggested that cells present in lymphoid tissues were the main source of BAFF. Through PCR analysis, we found that BAFF mRNA was present in T cells and peripheral blood monocyte-derived dendritic cells but not in B cells (FIG. 3B). Even naive, non-stimulated T cells appeared to express some BAFF mRNA.

A sequence tagged site (STS, SHGC-36171) was found in the database which included the human BAFF sequence. This site maps to human chromosome 13, in a 9 cM interval between the markers D13S286 und D13S1315. On the cytogenetic map, this interval corresponds to 13q32-34. Of the known TNF ligand family members, only RANKL (Trance) has been localized to this chromosome (22) though quite distant to BAFF (13q14).

In order for the ligand to exert maximal biological effects, it was likely that the BAFF receptor (BAFF-R) would be expressed either on the same cells or on neighboring cells present in lymphoid tissues. Using the recombinant sBAFF as a tool to specifically determine BAFF-R expression by FACS, we indeed found high levels of receptor expression in various B cell lines such as the Burkitt lymphomas Raji and BJAB (FIG. 4A, Table 1). In contrast, cell lines of T cell, fibroblastic, epithelial and endothelial origin were all negative. Very weak staining was observed with the monocyte line THP-1 which, however, could be due to Fc receptor binding. Thus, BAFF-R expression appears to be restricted to B cell lines. The two mouse B cell lines tested were negative using the human BAFF as a probe, although weak binding was observed on mouse splenocytes (data not shown). The presence of BAFF-R on B cells was corroborated by analysis of umbilical cord and peripheral blood lymphocytes. While CD8$^+$ and CD4$^+$ T cells lacked BAFF-R (FIG. 4B and data not shown), abundant staining was observed on CD19$^+$ B cells (FIGS. 4A and 4B), indicating that BAFF-R is expressed on all blood B cells, including naive and memory ones.

Figure 5A:
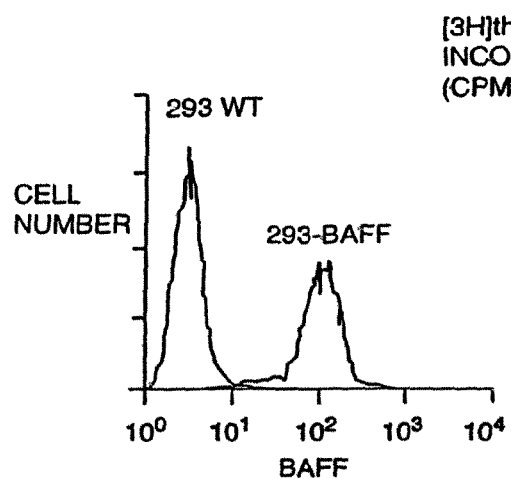
Figure 5B:
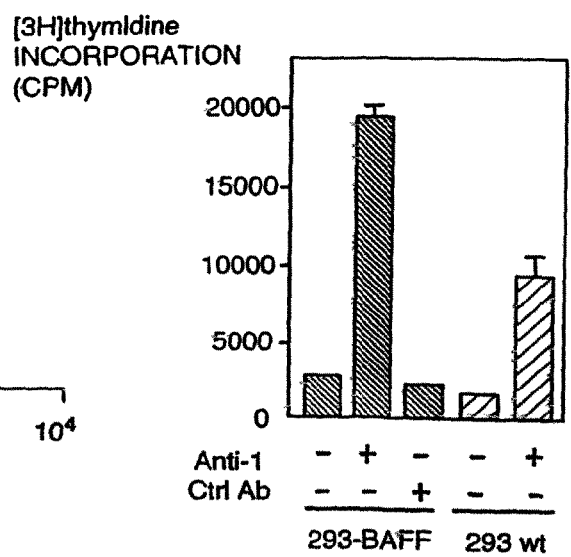
Figure 5C:
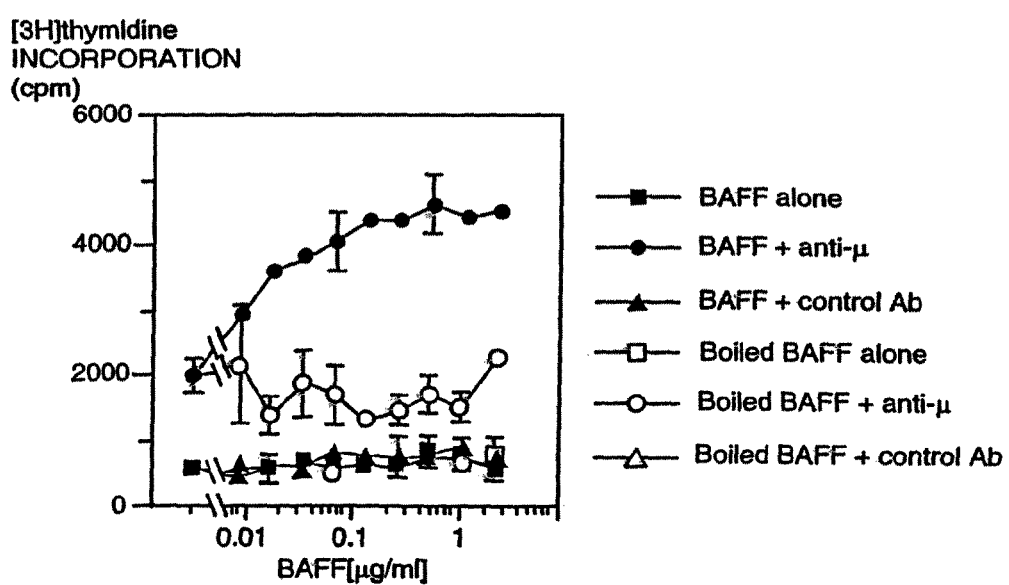
Figure 5D:
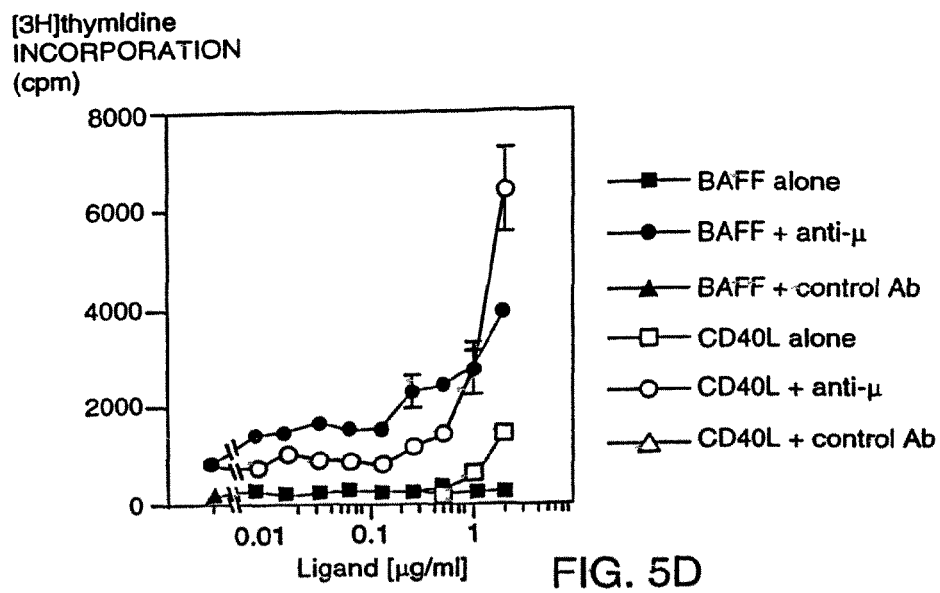

Since BAFF bound to blood-derived B cells, experiments were performed to determine whether the ligand could deliver growth-stimulatory or -inhibitory signals. Peripheral blood lymphocytes (PBL) were stimulated with anti-IgM (μ) antibodies together with fixed 293 sells stably expressing surface BAFF (FIG. 5A). The levels of [$^3$H]thymidine incorporation induced by anti-μ alone was not altered by the presence of control cells but was increased two-fold in the presence of BAFF-transfected cells (FIG. 5B). A dose-dependent proliferation of PBL was also obtained when BAFF-transfected cells were replaced by purified sBAFF (FIG. 5C), indicating that BAFF does not require membrane attachment to exert its activity. In this experimental setup, proliferation induced by sCD40L required concentrations exceeding 1 μg/ml but was less dependent on the presence of anti-μ than that mediated by BAFF (FIG. 5D). When purified CD19$^+$ B cells were co-cultured with irradiated autologous CD19$^-$ PBL, costimulation of proliferation by BAFF was unaffected, demonstrating that [$^3$H]thymidine uptake was mainly due to B cell proliferation and not to an indirect stimulation of another cell type data not shown).

The observed B cell proliferation in response to BAFF was entirely dependent on the presence of anti-μ antibodies, indicating that BAFF functioned as costimulator of B cell proliferation.

Figure 5E:
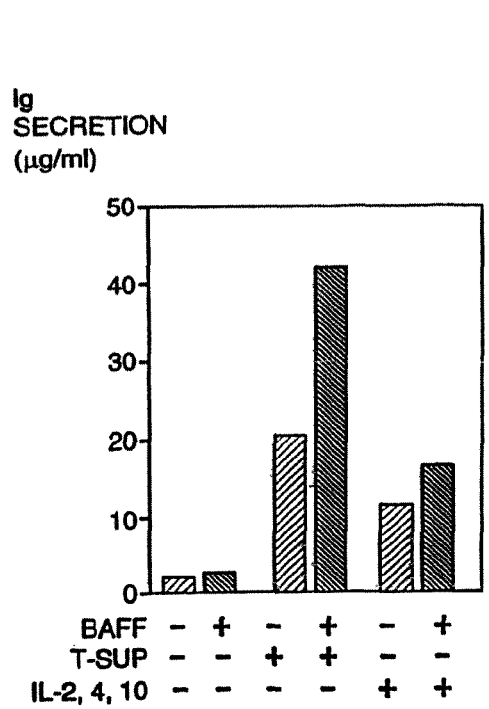
Figure 5F:
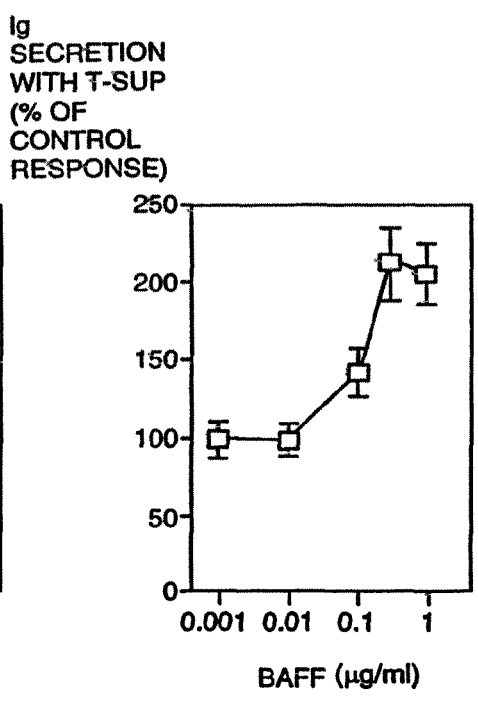

To investigate a possible effect of BAFF on immunoglobulin secretion, purified peripheral or cord blood B cells were preactivated by culture with EL-4 T cells in the presence of a cytokine mixture from supernatants of PHA/PMA stimulated T cells (23). These B cells were reisolated to 98% purity and yielded a two-fold increase in Ig secretion during a secondary culture in the presence of BAFF and activated T cell cytokines as compared to cytokines alone. A very modest effect occurred in the absence of exogenous cytokines, and an intermediate (1.5-fold) effect was observed in the presence of the recombinant cytokines IL-2, IL-4 and IL-10 (FIGS. 5E, F).

The biochemical analysis of BAFF is also consistent with the typical homotrimeric structure of TNF family members. Among this family of ligands, BAFF exhibits the highest level of sequence similarity with APRIL which we have recently characterized as a ligand stimulating growth of various tumor cells (11). Unlike TNF and LT□ which are two family members with equally high homology (33% identity) and whose genes are linked on chromosome 6, APRIL and BAFF are not clustered on the same chromosome. APRIL is located on chromosome 17 (J. L. B., unpublished data) whereas BAFF maps to the distal arm of human chromosome 13 (13q34). Abnormalities in this locus were characterized in Burkitt lymphomas as the second most frequent defect (24) besides the translocation involving the myc gene into the Ig locus (25). Considering the high expression levels of BAFF-R on all Burkitt lymphoma cell lines analyzed (see Table 1), this raises the intriguing possibility that some Burkitt lymphomas may have deregulated BAFF expression, thus stimulating growth in an autocrine manner.

The role of antigen-specific B lymphocytes during the different stages of the immune response is highly dependent on signals and contacts from helper T cells and antigen-presenting cells such as dendritic cells (20). B lymphocytes first receive these signals early on during the immune response when they interact with T cells at the edge of the B cell follicles in lymphoid tissues, leading to their proliferation and differentiation into low affinity antibody forming cells (18). At the same time some antigen-specific B cells also migrate to the B cell follicle and contribute to the formation of germinal centers, another site of B cell proliferation but also affinity maturation and generation of memory B cells and high affinity plasma cells (19).

Signals triggered by another member of the TNF super family CD40L have been shown to be critical for the function of B lymphocytes at multiple steps of the T cell-dependent immune response. However, several studies clearly showed that CD40L/CD40 interaction does not account for all contact-dependent T-cell help for B cells. Indeed, CD40L-deficient T cells isolated from either knock-out mice or patients with X-linked hyper IgM syndrome have been shown to successfully induce proliferation of B cells and their differentiation into plasma cells. Studies using blocking antibodies against CD40L showed that a subset of surface IgD positive B cells isolated from human tonsils proliferate and differentiate in response to activated T cells in a CD40-independent manner. Other members of the TNF family such as membrane-bound TNF and CD30L have also been shown to be involved in a CD40- and surface Ig-independent stimulation of B cells. Similar to our results with BAFF, it has been shown that CD40-deficient B cells can be stimulated to proliferate and differentiate into plasma cells by helper T cells as long as the surface Ig receptors are triggered at the same time. BAFF as well as CD30L and CD40L is expressed by T cells but its originality resides in its expression by dendritic cells as well as the highly specific location of its receptor on B cells which is in contrast to CD40, CD30 and the TNF receptor which expression has been described on many different cell. This observation suggests independent and specific BAFF-induced functions on B cells.

In support of a role for BAFF in T cell- and dendritic cell-induced B cell growth and potential maturation, we found that BAFF costimulates proliferation of blood-derived B cells concomitantly with cross-linking of the B cell receptors, and thus, independently of CD40 signalling. Moreover, using CD19 positive B cells differentiated in vitro into a pre-plasma-cell/GC-like B cell (14), we observed a costimulatory effect of BAFF on Ig secretion by these B cells in the presence of supernatant from activated T cells or a blend of IL-2, IL-4 and IL-10. Interestingly, the costimulatory effect was stronger in presence of the activated T cell supernatant when compared to the cytokine blend, suggesting additional soluble factors secreted by activated T cells involved in antibody production which can synergize with BAFF or additional BAFF itself. It is, therefore, possible that BAFF actively contributes to the differentiation of these GC-like B cells into plasma.

It is clear that BAFF can signal in both naive B cells as well as GC-committed B cells in vitro. Whether this observation will translate or not during a normal immune response will have to be addressed by proper in vivo experiments.

The biological responses induced in B cells by BAFF are distinct from that of CD40L, since proliferation triggered by CD40L was less dependent on an anti-μ costimulus (17) (and FIG. 5D). Moreover, CD40L can counteract apoptotic signals in B cells following engagement of the B cell receptor (29), whereas BAFF was not able to rescue the B cell line Ramos from anti-μ-mediated apoptosis, despite the fact that Ramos cells do express BAFF-R (Table 1; F. M. and J. L. B., unpublished observations). It is therefore likely that CD40L and BAFF fulfill distinct functions. In this respect, it is noteworthy that BAFF did not interact with any of 16 recombinant receptors of the TNF family tested, including CD40 (P. S and J. T, unpublished observations).

B cell growth was efficiently costimulated with recombinant soluble BAFF lacking the transmembrane domain. This activity is in contrast to several TNF family members which are active only as membrane-bound ligand such as TRAIL, FasL and CD40L. Soluble forms of these ligands have poor biological activity which can be enhanced by their cross-linking, thereby mimicking the membrane-bound ligand (15). In contrast, cross-linking Flag-tagged sBAFF with anti-FLAG antibodies or the use of membrane-bound BAFF expressed on the surface of epithelial cells did not further enhance the mitogenic activity of BAFF, suggesting that it can act systemically as a secreted cytokine, like TNF does. This is in agreement with the observation that a polybasic sequence present in the stalk of BAFF acted as a substrate for a protease. Similar polybasic sequences are also present at corresponding locations in both APRIL and TWEAK and for both of them there is evidence of proteolytic processing (30) (N. H. and J. T, unpublished observation). Although the protease responsible for the cleavage remains to be determined, it is unlikely to be the metalloproteinase responsible for the release of membrane-bound TNF as their sequence preferences differ completely (21). The multibasic motifs in BAFF (R-N-K-R) (SEQ ID NO:23), APRIL (R-K-R-R) (SEQ ID NO:24) and Tweak (R-P-R-R) (SEQ ID NO:25) are reminiscent of the minimal cleavage signal for furin (R-X-K/R-R) (SEQ ID NO:26), the prototype of a proprotein convertase family (31).

Practice of the present invention will employ, unless indicated otherwise, conventional techniques of cell biology, cell culture, molecular biology, microbiology, recombinant DNA, protein chemistry, and immunology, which are within the skill of the art. Such techniques are described in the literature. See, for example, *Molecular Cloning: A Laboratory Manual*, $2^{nd}$ edition. (Sambrook, Fritsch and Maniatis, eds.), Cold Spring Harbor Laboratory Press, 1989; *DNA Cloning*, Volumes I and II (D. N. Glover, ed), 1985; *Oligonucleotide Synthesis*, (M. J. Gait, ed.), 1984; U.S. Pat. No. 4,683,195 (Mullis et al.); *Nucleic Acid Hybridization* (B. D. Hames and S. J. Higgins, eds.), 1984; Transcription and Translation (B. D. Hames and S. J. Higgins, eds.), 1984; Culture of Animal Cells (R. I. Freshney, ed). Alan R. Liss, Inc., 1987; *Immobilized Cells and Enzymes*, IRL Press, 1986; *A Practical Guide to Molecular Cloning* (B. Perbal), 1984; *Methods in Enzymology*, Volumes 154 and 155 (Wu et al., eds), Academic Press, New York; *Gene Transfer Vectors for Mammalian Cells* (J. H. Miller and M. P. Calos, eds.), 1987, Cold Spring Harbor Laboratory; *Immunochemical Methods in Cell and Molecular Biology* (Mayer and Walker, eds.), Academic Press, London, 1987; *Handbook of Experiment Immunology*, Volumes I-IV (D. M. Weir and C. C. Blackwell, eds.), 1986; *Manipulating the Mouse Embryo*, Cold Spring Harbor Laboratory Press, 1986.

The following Examples are provided to illustrate the present invention, and should not be construed as limiting thereof.

EXAMPLES

The following experimental procedures were utilized in Examples 1-6.

DNA Construct for the Generation of Murine BAFF Tg Mice

Both human and murine cDNA sequences have been described previously (Schneider et al., 1999). A PCR fragment encoding full-length murine BAFF was generated by RT-PCR. First strand cDNA was synthesized from mouse lung polyA+ (Clontech, Palo Alto, Calif.) using oligo dT according to the manufacturer's protocol (GibcoBRL, Grand Island, N.Y.). The PCR reaction contained 1×Pfu buffer (Stratagene, La Jola, Calif.), 0.2 mM dNTPs, 10% DMSO, 12.5 pM primers, 5 units Pfu enzyme (Stratagene) and the following primers with Not1 restriction sites 5'-TAAGAAT-GCGGCCGCGGAATGGATGAGTCTGCAAA-3' [SEQ. ID. NO.: 19] and 5'-TAAGAATGCGGCCGCGGGAT-CACGCACTCCAGCAA-3' [SEQ. ID. NO.: 20]. The template was amplified for 30 cycles at 94° C. for 1 min, 54° C. for 2 min and 72° C. for 3 min, followed by a 10 min extension at 72° C. This sequence corresponds to nucleotides 214 to 1171 of the GenBank file AF119383. The PCR fragment was digested with Not1 and then cloned into a modified pCEP4 vector (Invitrogen, Carlsbad, Calif.). The fragment containing murine BAFF was removed with Xba1 in order to include the SV40 polyA addition site sequence. This fragment was cloned into a pUC based vector where the promoter sequence was added. The promoter, a 1 Kb blunt Bgl2-Not1 fragment containing the human ApoE enhancer and AAT (alpha anti-trypsin) promoter was purified from the plasmid clone 540B (a kind gift from Dr. Katherine Parker Ponder Washington University, St. Louis, Mo.). An EcoRV/ Bgl2 fragment was purified from the final vector and used for the generation of transgenic mice. The injected offspring of C57BL/6J female×DBA/2J male F1 (BDF1) mice were backcrossed onto C57BL/6 mice. Techniques of microinjection and generation of transgenic mice have been previously described (Mcknights et al., 1983).

Analytical Methods:

Serum samples were subject to reduced SDS-PAGE analysis using a linear 12.5% gel. Total RNA from mouse liver was prepared and processed for Northern Blot analysis using an isolation kit from Promega (Madison, Wis.) according to the manufacturer's guidelines. BAFF transgene-specific mRNA was detected using a probe spanning the SV40 poly A tail of the transgene construct and obtained by digestion of the modified pCEP4 vector with Xba1 and BamH1. The probe recognizes a 1.8-2 Kd band corresponding to mRNA from the BAFF transgene. PCR analysis of tail DNA from BAFF Tg mice was carried using 12.5 pM of the following primers 5'-GCAGTTTCACAGCGATGTCCT-3' [SEQ. ID. NO.: 21] and 5'-GTCTCCGTTGCGT-GAAATCTG-3' [SEQ. ID. NO.: 22] in a reaction containing 1× Taq polymerase buffer (Stratagene), 0.2 nM dNTPs, 10% DMSO and 5 units of Taq polymerase (Stratagene). A 719 bp of the transgene was amplified for 35 cycles at 94° C. for 30-sec., 54° C. for 1 min. and 72° C. for 1.5 min. followed by a 10 min. extension at 72° C.

The presence of proteins in mouse urine was measured using Multistix 10S-G reagent strips for urinalysis (Bayer-Corporation, Diagnostics Division, Elkhart, Ind.).

Cell-Dyn and Cytofluorimetric Analysis (FACS).

Differential WBC counts of fresh EDTA anticoagulated whole blood were performed with an Abbott Cell Dyne 3500 apparatus (Chicago, Ill.). For FACS analysis, Fluorescein (FITC)-, Cy-chrome- and Phycoerydirin-(PE)-labeled rat anti-mouse antibodies: anti-B220, anti-CD4, anti-CD8, anti-CD43, anti-IgM, anti-CD5, anti-CD25, anti-CD24, anti-CD38, anti-CD21, anti-CD44, anti-L-selectin and hamster anti-Bcl-2/control hamster Ig kit were purchased from Pharmingen (San Diego, Calif.). Production of recombinant *E. coli* as well as mammalian cell-derived human and mouse Flag-tagged BAFF were previously described (Schneider et al., 1999). All antibodies were used according to the manufacturer's specifications. PBL were purified from mouse blood as follows: mouse blood was collected in microtubes containing EDTA and was diluted 1/2 with PBS. Five hundred μl of diluted blood was applied on top of 1 ml of ficoll (Celardane, Hornby, Ontario, Canada) in a 4 ml glass tube, the gradient was performed at 2000 rpm for 30 min at room temperature and the interface-containing the lymphocytes was collected and washed twice in PBS prior to FACS staining. Spleen, bone marrow and mesenteric lymph nodes were ground into a single cell suspension in RPMI medium (Life Technologies, Inc., Grand Island, N.Y.) and washed in FACS buffer (PBS supplemented with 2% fetal calf serum (JRH Biosciences, Lenexa, Kans.). Cells were first suspended in FACS buffer supplemented with the following blocking reagents: 10 μg/ml human Ig (Sandoz, Basel, Switzerland) and 10 μg/ml anti-mouse Fc blocking antibody (Pharmingen) and incubated 30 min on ice prior to staining with fluorochrome-labeled antibodies. All antibodies were diluted in FACS buffer with the blocking reagent mentioned above. Samples were analyzed using a FACScan cytofluorometer (Becton Dickinson).

Detection of Total Mouse Ig and Rheumatoid Factors in Mouse Sera by ELISA Assays.

ELISA plates (Corning glass works, Corning, N.Y.) were coated overnight at 4° C. with a solution of 10 μg/ml of goat anti-total mouse Ig (Southern Biotechnology Associates, Inc. Birmingham, Ala.) in 50 mM sodium bicarbonate buffer pH 9.6. Plates were washed 3 times with PBS/0.1% Tween and blocked overnight with 1% gelatin in PBS. One hundred µl/well of serum serial dilutions or standard dilutions was added to the plates for 30 min at 37° C. Mouse Ig were detected using 100 µl/well of a 1 pa/ml solution of an Alkaline Phosphatase (AP)-labeled goat anti-total mouse Ig (Southern Biotechnology Associates) for 30 min at 37° C. After a last wash, 3 times with PBS/0.1% Tween, the enzymatic reaction was developed using a solution of 10 µg/ml of p-nitrophenyl phosphate (Boehringer Mannheim, Indianapolis, Ind.) in 10% diethanolamine. The reaction was stopped by adding 100 µl of 3N NaOH/well. The optical density (O.D.) was measured at 405 nm using a spectrophotometer from Molecular Devices (Sunnyvale, Calif.). Standard curves were obtained using purified mouse Ig purchased from Southern Biotechnology Associates. In the case of detection of rheumatoid factors (RF), the plates were coated with normal goat Ig (Jackson ImmunoResearch laboratories, Inc., West Grove, Pa.) instead of goat anti-mouse Ig and detection of mouse Ig was performed as described above. Detection of mouse isotypes in the RF assay was done using AP-labeled goat anti-mouse IgA, IgM, IgG2a, IgG2b and IgG3, as well as purified mouse IgA, IgM, IgG2a, IgG2b and IgG3 for standard curves (Southern Biotechnology Associates Inc.). All statistical comparisons were performed by analysis of variance.

Detection of Circulating Immune Complexes (CIC) and Precipitation of Cryoglobulins in Mouse Sera.

The assay was performed as previously described (June et al., 1979; Singh and Tingle, 1982) with the following modifications: ELISA plates (Corning glass works) were coated overnight at 4° C. with 5 µg/ml of human C1q (Quidel, San Diego, Calif.) in 50 mM sodium bicarbonate buffer pH 9.6. The plates were washed 3 times with PBS/0.1% Tween. Fifty µl/well of 0.3 M EDTA was added to the plates plus 50 µl/well of serum serial dilutions or solutions of known concentrations of a standard immune complex (peroxidase-mouse anti-peroxidase (PAP) from DAKO (Carpinteria, Calif.). The plates were incubated 30 min at 37° C. The plates were washed 3 times with PBS/0.1% Tween. Mouse Ig in the immune complexes were detected using 100 µl/well of a 1 µg/ml solution of an AP-labeled goat anti-mouse Ig (Southern Biotechnology Associates, Inc.) as described above for the ELISA assays. Cryoglobulins were detected by incubating overnight at 4° C. mouse serum diluted 1/15 in water and precipitates were scored visually.

Anti-Double Stranded (Ds) and Single-Stranded (Ss) DNA Assays.

Anti-ssDNA were performed using NUNC-immuno Plate MaxiSorp plates (NARC A/S, Denmark). Plates were coated overnight at 4° C. first with 100 µg/ml methylated BSA (Calbochem Corp., La Jolla, Calif.), then with 50 µg/ml grade I calf thymus DNA (Sigma, St. Louis, Mo.). The calf thymus DNA was sheared by sonication and then digested with S1 nuclease before use. For the anti-ssDNA assay, the DNA was boiled for 10 min and chilled on ice before use. After blocking, serial dilutions of the serum samples were added and incubated at room temperature for 2 h. Autoantibodies were detected with goat anti-mouse IgG-AP (Sigma) and develop as described above for the ELISA assays. Standard curves were obtained using known quantities of anti-DNA mAb 205, which is specific for both ss- and dsDNA (Datta et al., 1987).

Immunohistochemistry

Spleen and lymph nodes were frozen in O.C.T. embedding medium (Miles, Elkhart, Ind.) and mounted for cryostat sectioning. Sections 7-10 µm thick were dried and fixed in acetone. All Ab incubations (10 µg/ml) were done for 1 hr at room temperature in a humidified box after dilution in Tris-buffered saline A (TBS-A, 0.05M Tris, 0.15M NaCl, 0.05% Tween-20 (v/v), 0.25% BSA), rinsed in TBS-B (0.05M Tris, 0.15M NaCl, 0.05% Tween-20) and fixed 1 min in methanol before initiating the enzymatic reaction. Horseradish peroxidase (HRP) and alkaline phosphatase (AP) activities were developed using the diaminobenzidine (DAB) tablet substrate kit (Sigma) and the 5-bromo-4-chloro-3-indolyl phosphate/nitro blue tetrazolium (BCIP/NBT, Pierce, Rockford, Ill.), respectively. Stained tissue sections were finally fixed 5 min in methanol and counter stained with Giemsa (Fluka, Buchs, Switzerland). Biotin-labeled antibodies rat anti-B220, anti-CD11c, anti-syndecan-1 as well as unlabeled rat anti-CD4, anti-CD8α and anti-CD8β were purchased from Pharmingen. Biotin-labeled peanut agglutinin (PNA) was obtained from Vector laboratories (Burlingame, Calif.). (HRP)-labeled mouse anti-rat Ig and (HRP)-streptavidin were purchased from Jackson ImmunoResearch laboratories, Inc. and AP-labeled strepvidin from Southern Biotechnology Associates, Inc. In the case of immunohistochemistry on kidney tissue to detect Ig deposition, paraffin section were used, dewaxed and blocked using diluted horse serum from Vector (Burlingame, Calif.), followed by staining with HRP-goat anti-mouse Ig from Jackson immunoresearch. Detection was performed as described above.

Example 1

BAFF Transgenic (BAFF Tg) Founder Mice have an Abnormal Phenotype

Full length murine BAFF was expressed in transgenic mice using the liver specific alpha-1 antitrypsin promoter with the APO E enhancer. The full length version was chosen with the expectation that BAFF would be either cleaved and act systemically or if retained in a membrane bound form that local liver specific abnormalities would be observed possibly providing functional clues. We obtained 13 founder mice positive for the BAFF transgene (Table 2). Four of these mice died at a young age. Routine pathology was carried out on mice 811 and 816 (Table 2). There was no obvious infection in these mice; however, cardiovascular and renal abnormalities were apparent and similar to those described for severe hypertension (Fu, 1995) (Table 2). Hematoxylin and eosin (H&E)-stained kidney tissue-sections of founder 816 showed that the morphology of glomeruli in that mouse was abnormal, whereas the rest of the kidney tissue seemed normal (data not shown). Many BAFF transgenic founder mice had proteinuria (Table 2). Immunohistochemistry on spleen frozen tissue sections from mouse 816, revealed an abnormal and extensive B cell staining and reduced staining for T cells and this observation was confirmed in the progeny (see below, FIG. 12).

Using two color FACS analysis, the ratio of % B220 positive B cells over % CD4 positive T cells was calculated. This ratio was two to seven times higher in BAFF Tg founder mice when compared to control negative BDF1 nice (Table 2), suggesting an increase of the B cell population in BAFF Tg mice. We selected nine of these founder mice to generate our different lines of transgenic mice as underlined in Table 2. None of the remaining BAFF Tg founder mice or the derived progeny showed any signs of ill health months after the early death of founders 696, 700, 811 and 816, suggesting that these 4 mice might have expressed higher levels of BAFF which caused their death. BAFF overexpression in the liver of transgenic mice was confined by Northern blot analysis (data not shown). In all BAFF-Tg mice examined histologically, the livers showed no abnormalities indicating that local overexpression of BAFF did not induce any immunological or pathological events. An ELISA assay for murine BAFF is not available; however, we showed that 2% serum from BAFF Tg mice, but not from control mice, blocked the binding of mammalian cell-derived mouse soluble Flag-tagged BAFF to BJAB cells. Moreover, 5% serum from BAFF Tg mice but not from control mice increased the proliferation of human B cells from PBL in the presence of anti-µ (data not shown). These data suggest that substantial amounts of soluble BAFF are present in the blood of BAFF Tg.

Example 2

Peripheral Lymphocytosis in BAFF Tg Mice is Due to Elevated B Cell Numbers

Figure 7A:
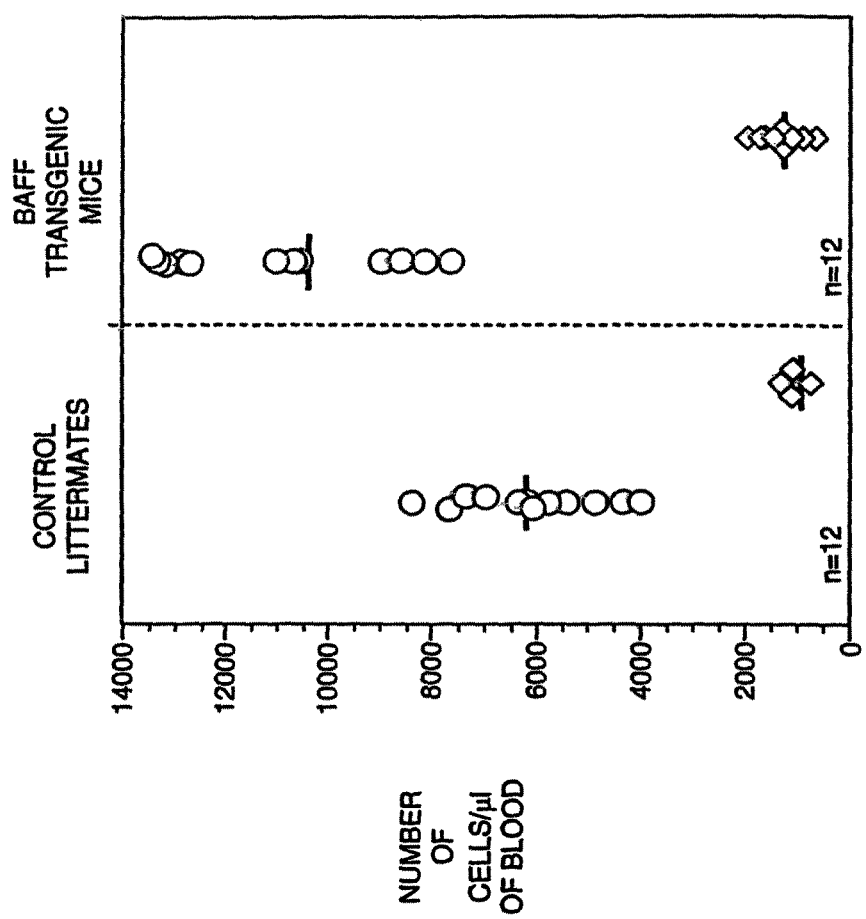
Figure 7C:
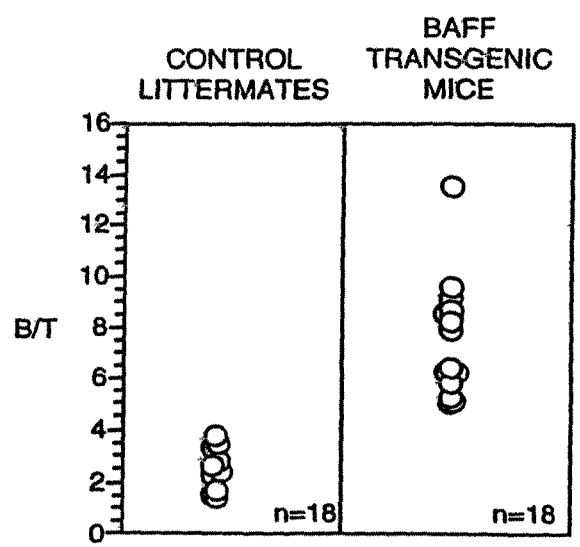
Figure 7D:
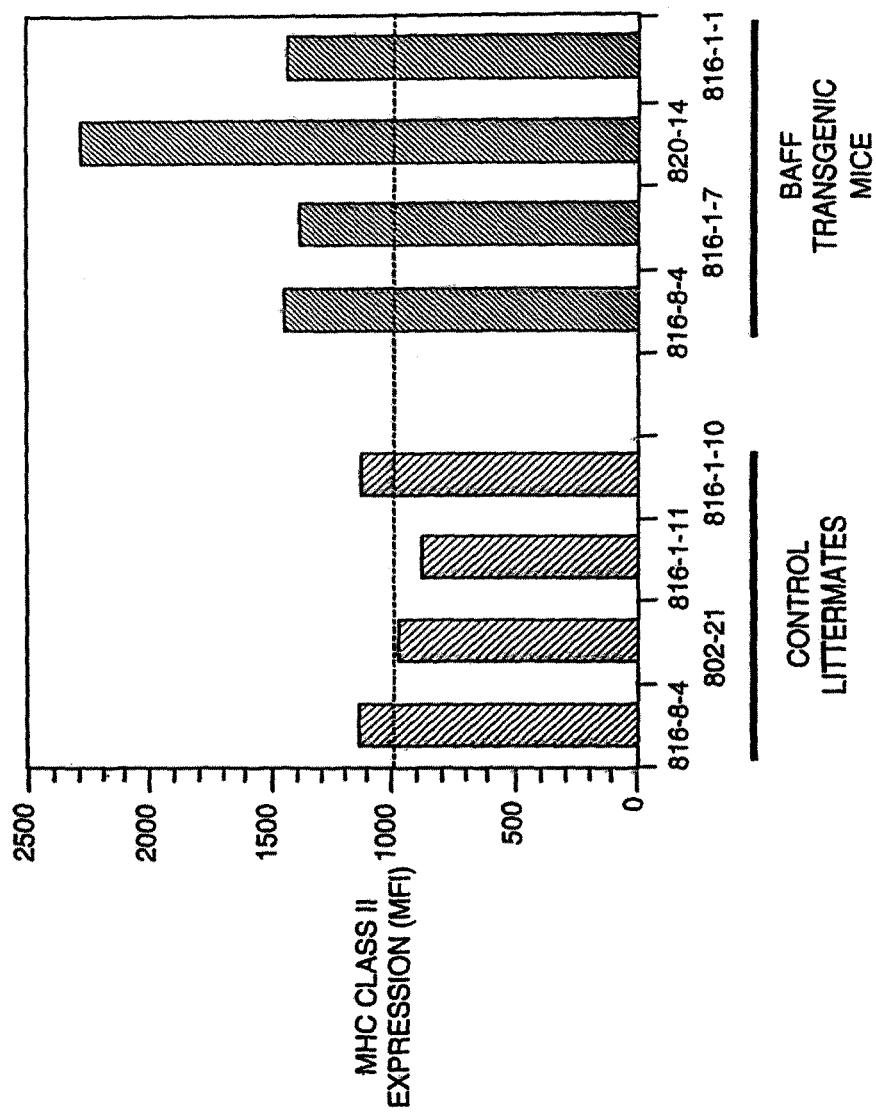
Figure 7F:
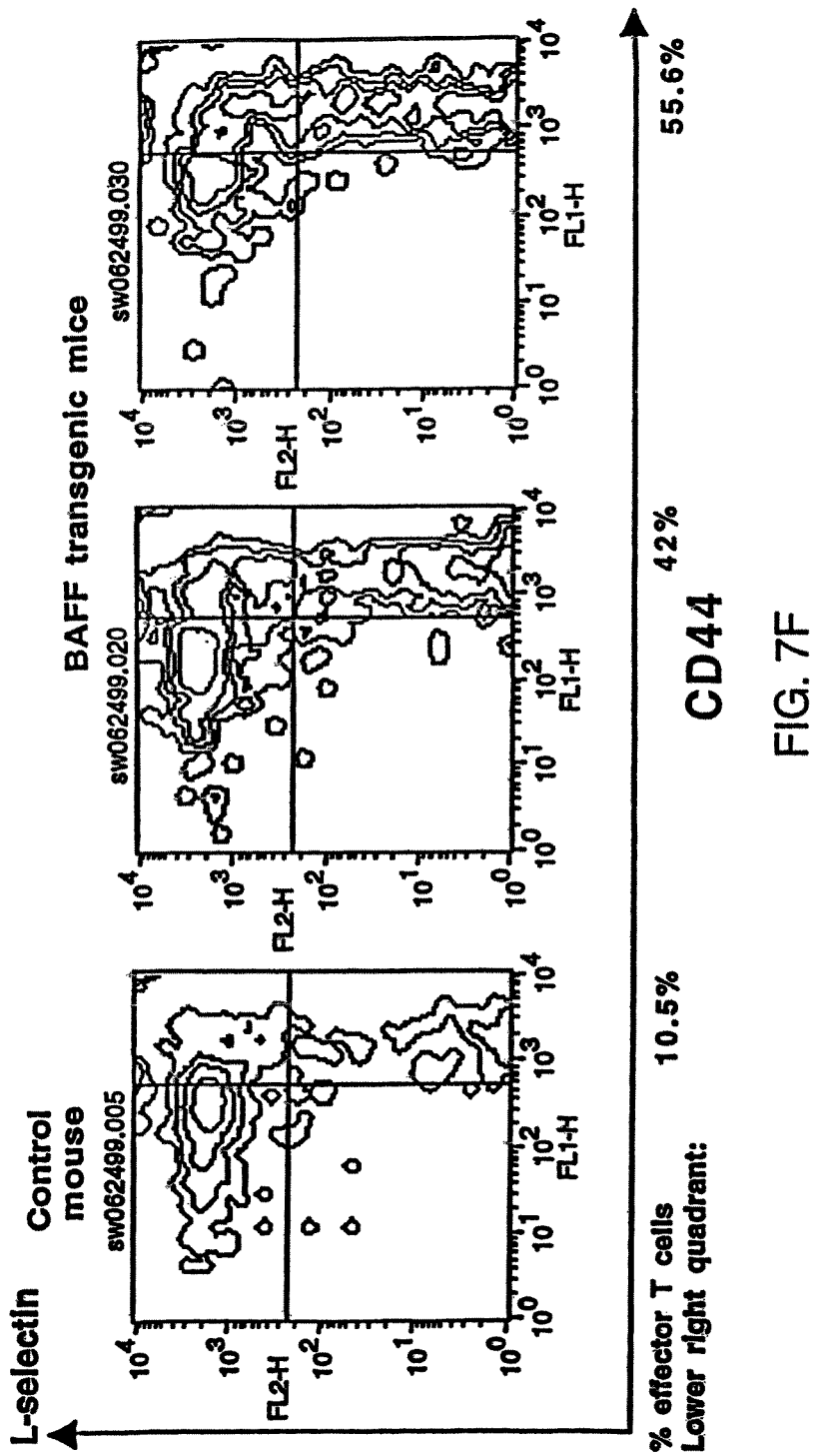

The transgenic mice population was found to have more lymphocytes in the blood when compared to control negative littermates, reaching values as high as 13000 lymphocytes/µl of blood (FIG. 7A). In contrast, the number of granulocytes per µl of blood in both BAFF Tg mice and control mice remained within normal limits (FIG. 7A). Since FACS analysis, using anti-CD4 and anti-B220 antibodies, of peripheral blood cells (PBL) from 18 BAFF Tg mice issued from six different founder mice showed increased B/T ratios FIGS. 7B and 7C), the elevated lymphocyte levels resulted from an expanded B cell subset. Likewise, using this method, calculation of absolute numbers of CD4 circulating T cells revealed a 50% reduction of this T cell subset in BAFF Tg mice when compared to control mice, and the same observation was made for the CD8 T cell subset (data not shown). All B cells from the PBL of BAFF Tg mice have increased MHC class II and Bcl-2 expression when compared to B cells from control mice (FIGS. 7D and 7E, respectively), indicating some level of B cell activation in PBL of BAFF Tg mice. T cells in the blood of BAFF Tg mice did not express the early activation markers CD69 or CD25; however, 40 to 56% of CD4 or CD8 T cells were activated effector T cells with a $CD44^{hi}$, L-selectin$^{lo}$ phenotype versus only 8% to 12% in control littermates FIG. 7F). Thus BAFF Tg mice clearly show signs of B cell lymphocytosis and global B cell activation along with T cell alterations.

Example 3

Expanded B Cell Compartments are Composed of Mature Cells

Figure 8B:
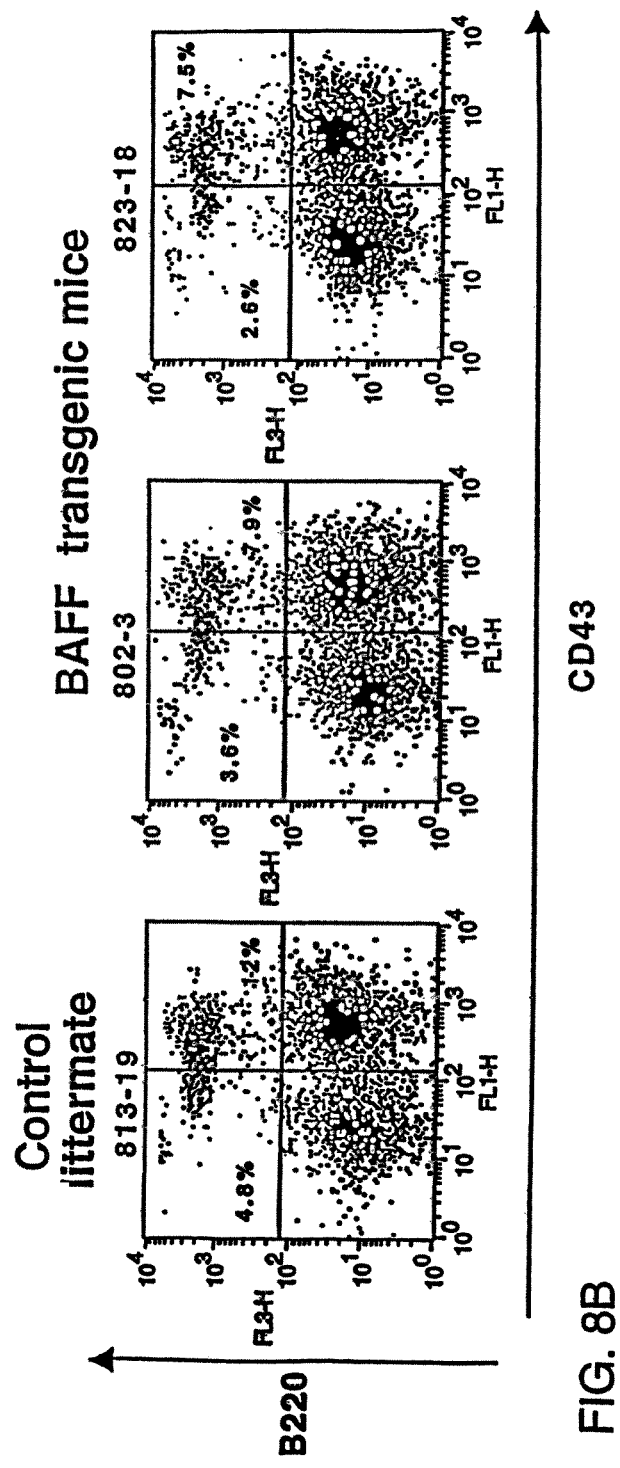

To see whether overexpression of BAN in the transgenic mice was affecting the B cell compartment centrally in the bone marrow and peripherally in secondary lymphoid organs, we examined by FACS the spleen, bone marrow and mesenteric lymph nodes from a total of seven BAFF Tg mice and seven control littermates derived from four different founder mice. The mature B cell compartment was analyzed by staining with both anti-B220 and anti-IgM antibodies. Two representative BAFF Tg mice and one representative control littermate are shown in FIG. 8. The mature B cell compartment (IgM+. B220+) was increased in both the spleen and the mesenteric lymph nodes (FIG. 8A, top and bottom panels, respectively). Analysis of B220+/IgM+ B cells (FIG. 7A, middle panel) or the proB cell (CD43+/B220+) and the preB cell (CD43−/B220+) compartments in the bone marrow (FIG. 8B) showed that BAFF Tg mice and control littermates were similar. These data indicate that overexpression of BAFF is affecting the proliferation of mature B cells in the periphery but not progenitor B cells in the bone marrow. Analysis by FACS of the B cell subpopulations in the spleen, revealed an increased proportion of marginal zone (MZ) B cells in BAFF Tg mice when compared to control mice (Table 3). The population of follicular B cells remained proportional in both BAFF Tg and control mice whereas the fraction of newly formed B cells is slightly decreased in BAFF Tg mice (Table 3). This result was also confirmed on B220$^+$ splenic B cells using anti-CD38 versus anti-CD24 antibodies and anti-IgM versus anti-IgD antibodies and analyzing for at the $CD38^{hi}/CD24^+$ and $IgM^{hi}/IgD^{lo}$ for the MZ B cell population, respectively, as previously described (Oliver et al., 1997)(data not shown). Immunohistochemical analysis using an anti-mouse IgM antibody revealed the expansion of the IgM-bright MZ B cell area in the spleen of BAFF Tg mice when compared to control mice (data not shown). All BAFF T-g B220$^+$ splenic B cells also express higher levels of MHC class II (Table 3) and Bcl-2 (data not shown) compared to splenic B cells from control mice, indicating that splenic B cells as well as B cells from PBL are in an activated state.

Example 4

Figure 9B:
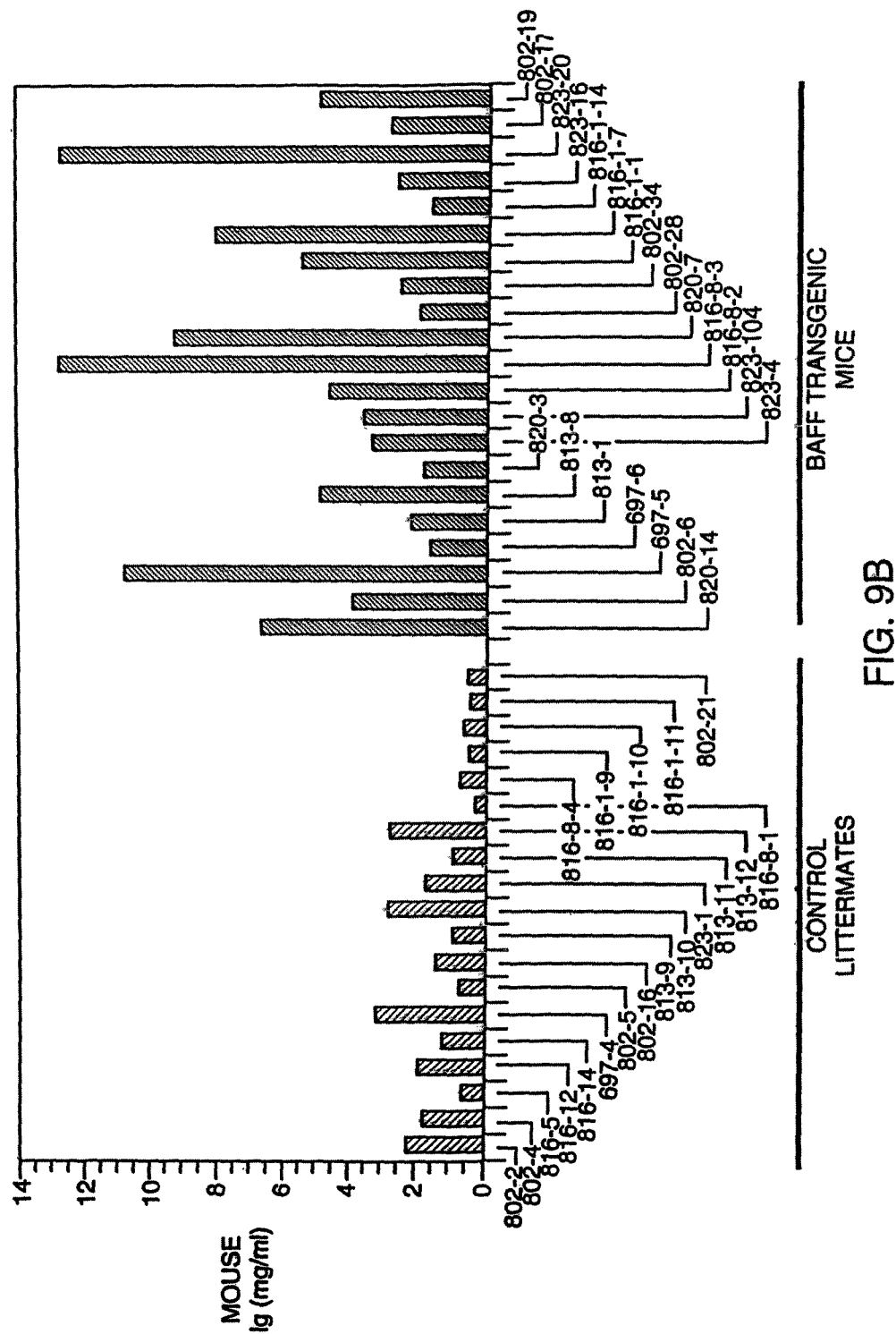

BAFF Tg Mice have High Levels of Total Immunoglobulins, Rheumatoid Factors and Circulating Immune Complexes in their Serum The increased B cell compartment in BAFF Tg mice suggested that the level of total Ig in the blood of these animals might also be increased. SDS-PAGE, analysis of serum from BAFF Tg mice and control littermates showed that the heavy and light chains IgG bands were at least 10 fold more intense in 3 out of 4 BAFF Tg mice compared to the control sera (FIG. 9A). Likewise, an ELISA determination on the sera from BAFF Tg mice show significantly higher total Ig levels when compared to that of the control mice (FIG. 9B).

Figure 9C:
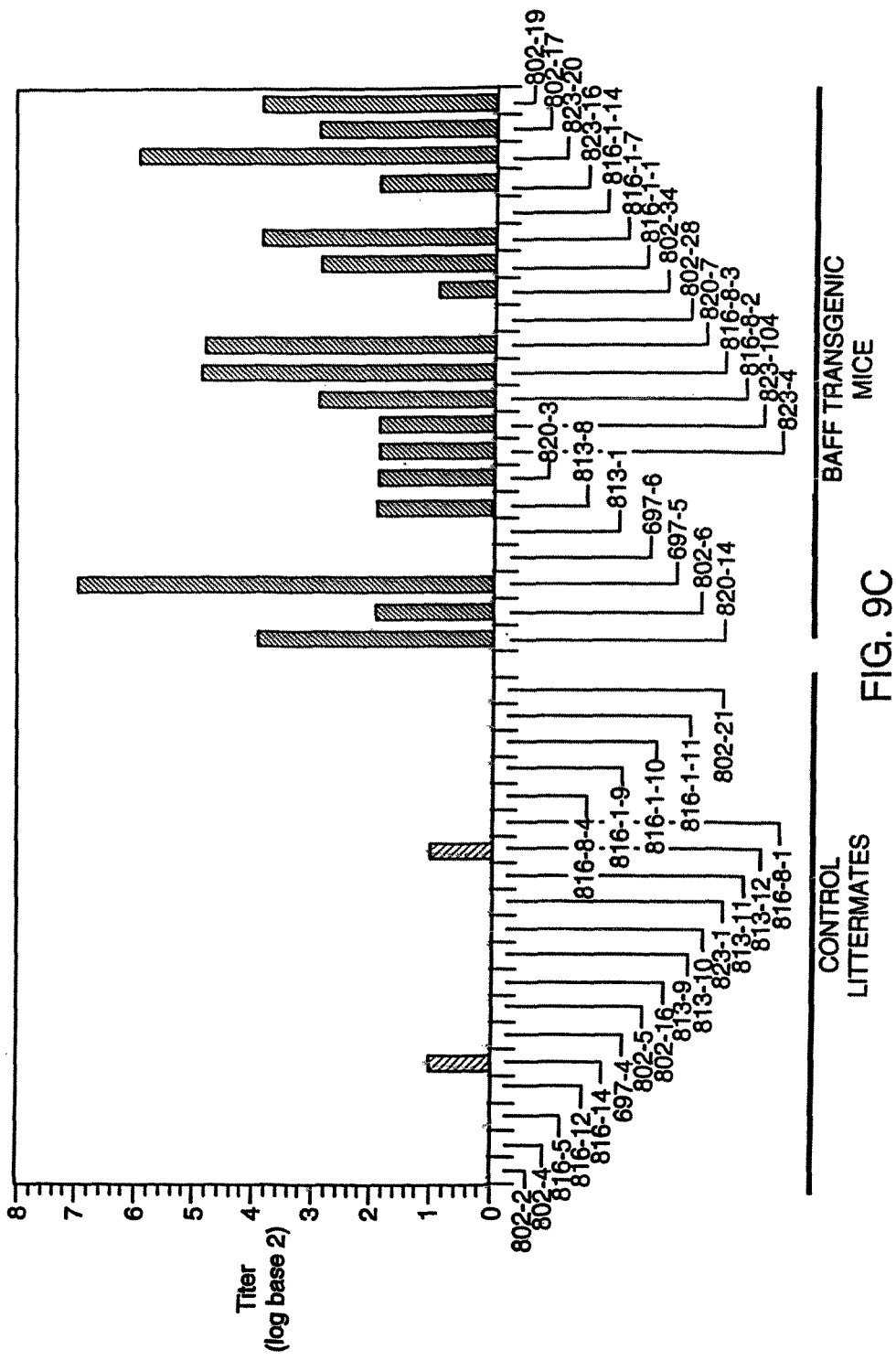

Despite the high levels seen by SDS-PAGE, the excessively high levels of Ig seen by ELISA determination in some mice, e.g., 697-5, 816-8-3 and 823-20, led us to suspect the presence of rheumatoid factors (RF) in the sera, or autoantibodies directed against antigenic determinants on the Fc fragment of IgG (Jefferis, 1995). These antibodies could bind to the goat anti-mouse Ig used to coat the ELISA plates and give erroneously high values. ELISA plates were coated with normal irrelevant goat Ig and the binding of BAFF Tg Ig to normal goat Ig was measured. FIG. 9C shows that sera from most BAFF Tg mice contained Ig reacting with normal goat Ig, whereas only two out of 19 control mice exhibited reactivity in the same assay. These RF were mainly of the IgM, IgA and IgG2a isotypes (data not shown).

Figure 9D:
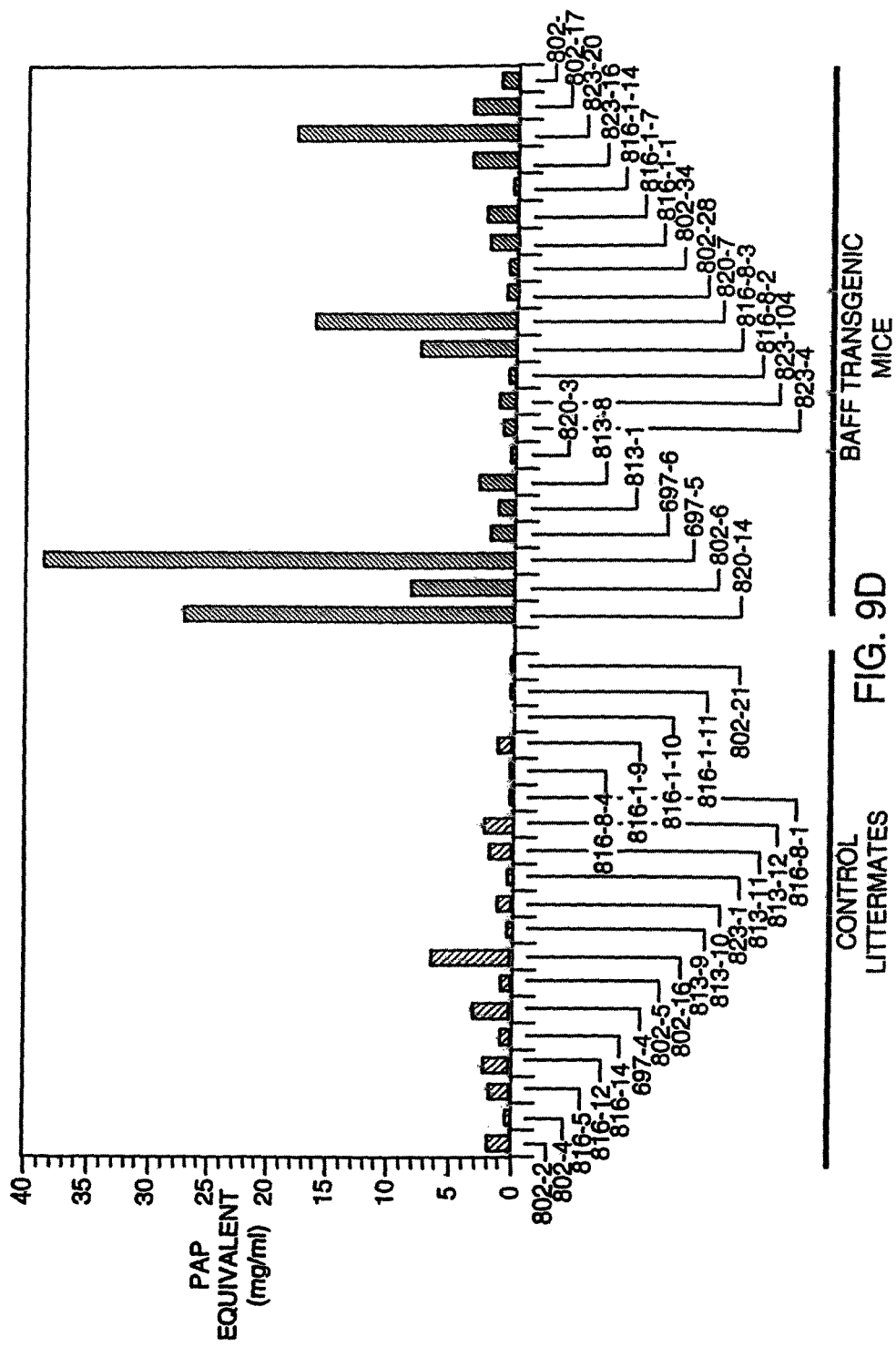

Presence of RF can be associated with the presence of high levels of circulating immune complexes (CIC) and cryoglobulin in the blood (Jefferis, 1995). To verify whether or not BAFF Tg mice have abnormal serum levels of CIC, a C1q-based binding assay was used to detect CIC in the 21 BAFF Tg mice analyzed above. Only 5 BAFF T-g showed significantly high levels of CIC when compared to control mice, nonetheless these mice corresponded to the animals having the highest total Ig and rheumatoid factor levels (FIG. 9D). We also observed precipitate formation when BAFF Tg mice sera were diluted 1/15 in water but not control sera indicating the presence of cryoglobulin in these mice (data not shown). Thus, in addition to B cell hyperplasia, BAFF Tg mice display severe hyperglobulinermia associated with RF and CIC.

Example 5

Figure 10A:
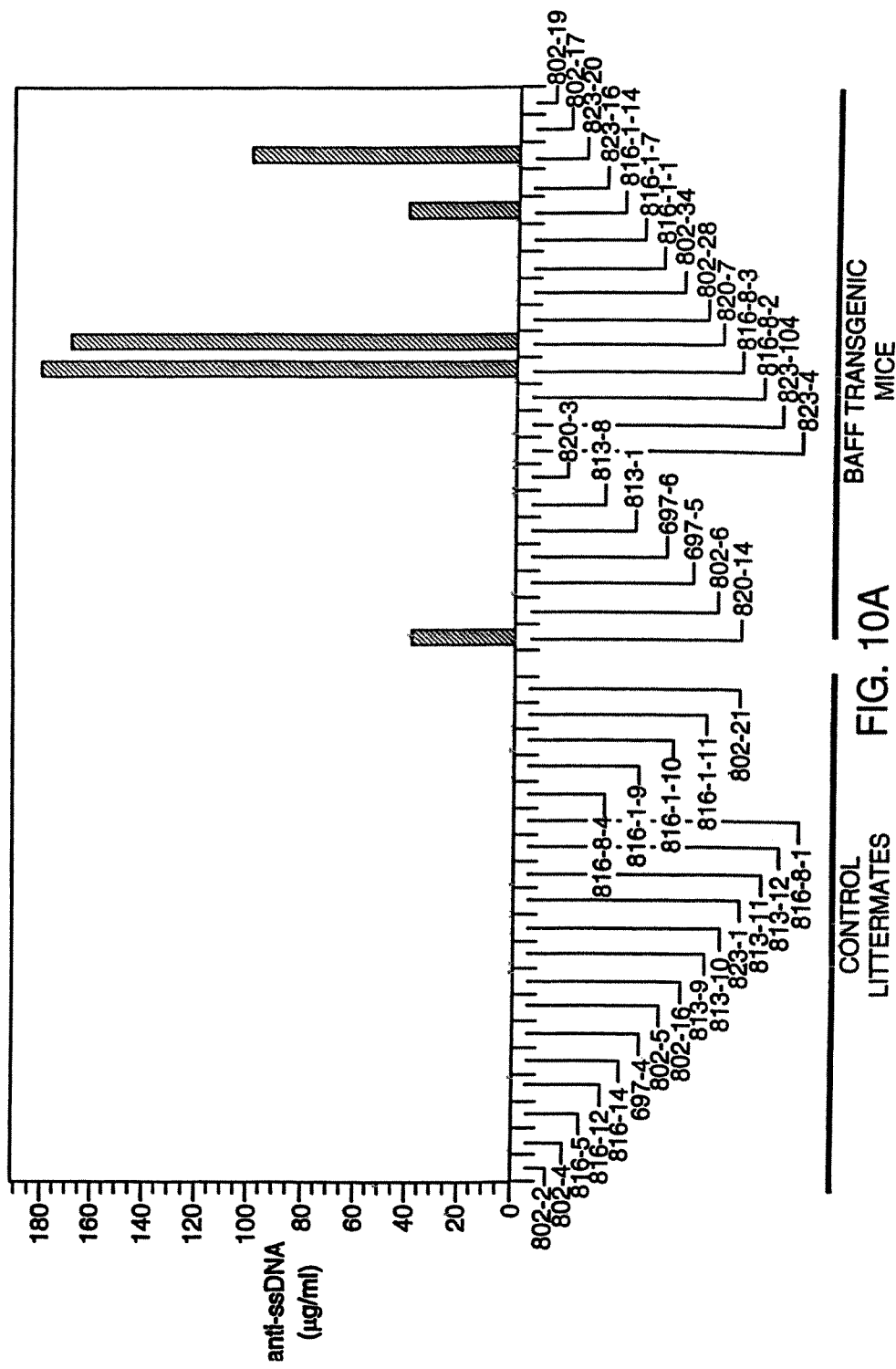
Figure 10B:
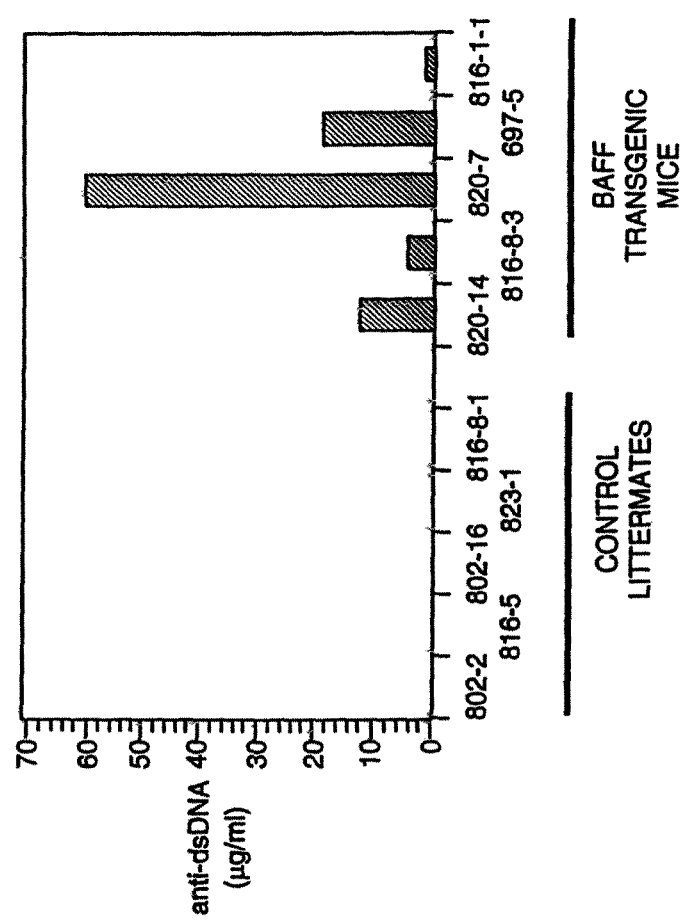
Figure 10C:
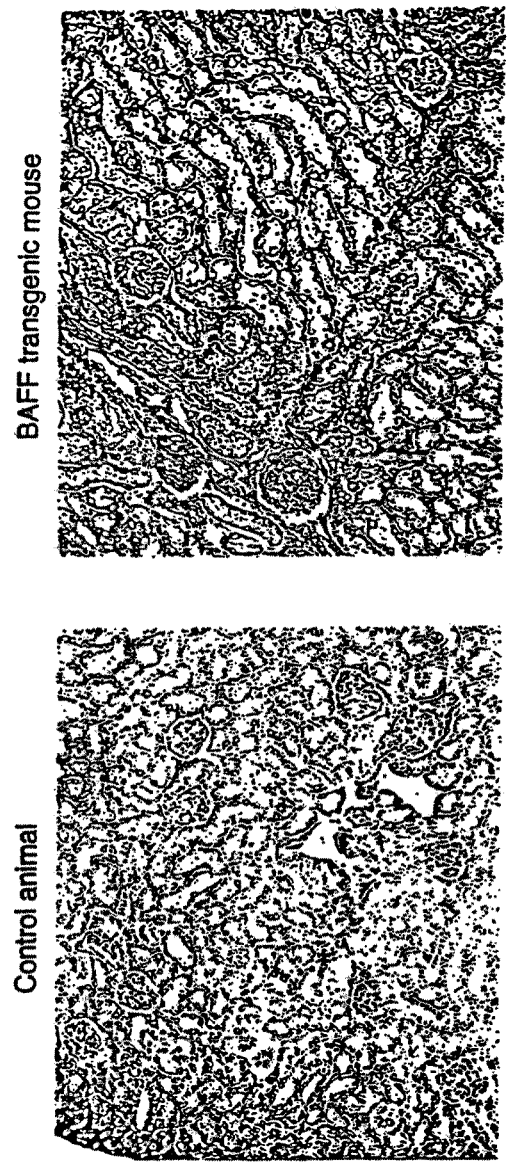

Some BAFF Tg Mice have High Levels of Anti-Single Stranded (Ss) and Double-Stranded (Ds) DNA Autoantibodies Initially, we observed kidney abnormalities reminiscent of a lupus-like disease in two of our founder mice (Table II). The presence of anti-DNA autoantibodies have also been described in SLE patients or the SLE-like (SWR×NZB)F1 (SNF1) mouse (Datta et al., 1987). Anti-ssDNA autoantibody levels were detected in BAFF Tg mice previously shown to have the highest level of total serum Ig (FIG. 10A). We analyzed the serum of two BAFF Tg mice negative for antibodies against ssDNA (697-5 and 8161-1) and three transgenic mice secreting anti-ssDNA antibodies (820-14, 816-8-3 and 820-7) for the presence of anti-dsDNA antibodies in parallel with five control littermates. BAFF Tg mice also secreted anti-dsDNA, however, the levels of secretion did not always correlate with that of anti-ssDNA antibodies, as serum from BAFF Tg mouse 697-5 which did not contain detectable levels of anti-ssDNA antibodies, was clearly positive for the presence of anti-dsDNA (FIG. 10B). Therefore, BAFF Tg mice showing the most severe hyperglobulinemia secrete pathological levels of anti-DNA autoantibodies. Additionally, and also reminiscent of a lupus-like problem in these mice we detected immunoglobulin deposition in the kidney of six BAFF Tg mice analyzed (FIG. 10C), three of these mice did not secrete detectable levels anti-DNA antibodies (data not shown).

Example 6

BAFF Tg Mice have Enlarged B Cell Follicles, Numerous Germinal Centers, Reduced Dendritic Cell Numbers and Increased Plasma Cell Numbers in Both the Spleen and Mesenteric Lymph Nodes (MLN)

BAFF Tg mice had large spleens, M (data not shown) and Peyer's patches (FIG. 11). Immunohistochemistry showed the presence of enlarged B cell follicles and reduced peripheral arteriolar lymphoid sheets (PALS or T cell area) in BAFF Tg mice (FIG. 12B). Interestingly, few germinal centers were observed in non-immunized control littermates (and is typical of this colony in general) and those present were small (FIGS. 1-2C), whereas BAFF Tg mice possessed numerous germinal centers in the absence of immunization (FIG. 12D). Staining with anti-CD11c for dendritic cells in the T cell zone and the marginal zone of control mice (FIG. 12E) was considerably reduced in BAFF Tg mice (FIG. 1-2F). Syndecan-1-positive plasma cells were almost undetectable in the spleen from control littermates (FIG. 12G), yet the red pulp of BAFF Tg mice was strongly positive for syndecan-1 (FIG. 12H). Very similar observations were made for the MLN (FIG. 13). In the MLN of BAFF Tg mice the B cell areas were dramatically expanded (FIG. 13B) in contrast to the normal node where B cell follicles were easily recognizable at the periphery of the node under the capsule with a typical paracortical T cell zone (FIG. 13A). The medulla of MLN from BAFF Tg mice were filled with syndecan-1 positive cells which presumably are plasma cells (FIG. 13H). In conclusion, analysis of secondary lymphoid organs in BAFF Tg mice was consistent with the expanded B cell phenotype showing multiple cellular abnormalities and intense immune activity.

The following experimental procedures were used in Examples 7-13.

Mice and Reagents.

Full length murine BAFF was expressed in transgenic mice using the liver-specific alpha 1 antitrypsin promoter with the Apo E enhancer as previously described. MacKay et al. (1999) J. Exp. Med. 190:1697-1710). C57BL/6 mice were purchased from ARC (Perth, Australia). BAFF transgenic mice are maintained as heterozygotes for the transgene by backcrossing onto C57BL/6 mice. BAFF Tg mice are screened for the presence of the transgene, both by PCR and southern blot analysis using genomic DNA isolated from 2-3 mm long tail snips. (MacKay et al.). We used animals from two separate lines of BAFF Tg mice issued after 10-12 backcrossings to C57BL/6. Age-matched negative littermates were used as controls. Animals between 8 and 17 months of age were used. Animals were housed under conventional barrier protection and handled in accordance with the Animal Experimentation and Ethic Committee (AEEC), which complies with the Australian code of practice for the care and use of animals for scientific purposes. Flag-tagged soluble human BAFF amino acids (aa) 83-285) was expressed by E. coli and purified as described previously. (Schneider et al. (1999) J. Exp. Med. 189:1747-1756.) Anti-human BAFF antibodies Buffy-2 (rat IgM), Buffy-5 (Rat IgG1) and A21G3.3 (mouse IgG1, κ) were obtained after immunization of rats or mice with recombinant soluble human BAFF as previously detailed. (Schneider et al.). These antibodies recognize the TNF homology domain of soluble BAFF. The antibody A21G3.3 was purified as follows: 500 ml of medium from hybridoma cultures were diluted 1 to 1 with 0.1 M Sodium Phosphate (pH 7.2) buffer containing 150 mM of NaCl. The diluted media was loaded onto a protein-L column (Clontech, Palo Alto, Calif.) at 1 ml/minute and eluted with 0.1 M Glycine (pH 2.8). The eluted solution was neutralized with 1 M Sodium Phosphate buffer (pH 7.2). The peak fractions were confirmed by SDS-PAGE. Centricon Plus-20 (Millipore, Bedford, Mass.) was used to exchange the buffer to PBS and to concentrate the purified antibody. The purified A21G3.3 antibody was labelled with 10× mole of EZ link sulfo-NHS-LC Biotin (Pierce, Rockford, Ill.) and incubated at room temperature for 30 minutes. The biotinylation reaction was stopped with 150 mM glycine. The sample was further purified with a desalting column to remove the free biotin (Amersham Pharmacia, Uppsala, Sweden).

Flow Cytometry.

Mice were sacrificed and spleen and submaxillary glands were collected. Spleens and lymph nodes were dissociated by grinding between frosted glass slides (Menzel-Glaser, Braunschweig, Germany). Cells were filtered through a 70 µm nylon Cell Strainer (Falcon, Becton Dickinson, Franklin Lakes, N.J.) and erythrocytes (only for spleen) removed by osmotic lysis with red blood cell lysis solution (8.34 mg/ml ammonium chloride, 0.84 mg/ml sodium bicarbonate, 1 mM EDTA, pH 8.0). Submaxillary glands were cut into pieces of 2-3 millimeters and incubated in a sterile collagenase solution troche Diagnostics, Mannheim, Germany), 1 mg/ml in PBS ($Ca^{2+}$ and $Mg^{2+}$ free), for 1 h at 37° C., until leukocytes were released from the tissue. After digestion, the cell suspension was filtered through a 70 µm nylon cell strainer (Falcon) and filtered cells were washed twice with PBS. Leukocytes obtained from spleens or submaxillary glands were resuspended in FACS buffer (1% BSA, 0.05% sodium azide in PBS) at a concentration of $5 \times 10^6$ cells/ml. Surface staining was done using various combinations of FITC-, PE-, Cy5- and Cychome™-labelled antibodies. Fluorescent-labeled anti-mouse antibodies anti-CD4 (L3T4), anti-CD8a (Ly-2) anti-CD45R/B220 (RA3-6B2), anti-Ly6-G (GR1), anti-IgD (11-26c.2a), anti-CD11b (Mac1), anti-Ly55 (NK1.1, NKR-P1C), anti-IgM R6-60.2), anti-CD23 (IgE Fc Receptor, clone B3B4), anti-CD24 (Heat Stable Antigen, 30F1), anti-CD43 (S7), anti-L-selectin ML-14), anti-CD1 (1B1) and anti-CD21 (7G6) were supplied by BD PharMingen (San Diego, Calif.). Cy5-conjugated anti-IgM antibody was purchased from Jackson ImmunoResearch laboratories Inc. (West Grove, Pa.). FITC-labeled antibodies were used diluted 1/100 whereas other fluorochrome-labelled antibodies were used at 1/200 final dilution. For flow cytometry we acquired 30,000-100,000 events per sample. Data was collected on a FACSCalibur flow cytometer and analysed using CELLQuest™ software (Becton Dickinson).

Immunohistochemistry.

Spleen (removed comma) and submaxillary glands were collected from both control and BAFF Tg mice. Tissues were either frozen in OCT compound (Tissue-Tek, Sakura Finetek, Torrance, Calif., USA) or fixed in 10% buffered formalin and embedded in parafiln. Biopsies of human parotid glands were processed into paraffin blocks by pathologists at the Flinders Medial center in Adelaide. Paraffin sections, 5 µm thick, were re-hydrated in successive baths of xylene, 100% ethanol and $H_2O$. Slides were cooked under pressure in citrate buffer (8.2 nM trisodium citrate, 1.7 mM citrate acid, pH 6.0). Slides were either stained with hematoxylin-eosin (H&E) for histologic examination or used for immunohistochemical staining. Prior to immunohistochemical staining tissue sections were pre-incubated with human Ig (Sandoz, Basel, Switzerland) 10 µg/ml in TBS-Triton (0.5% Triton) to block non-specific binding and washed twice with TBS-Triton. Sections were incubated with rat anti-human BAFF (Buffy-2) or an isotype-matched control rat antibody (Jackson ImmunoResearch Laboratories, Inc.), 5 µg/ml for 30 min at room temperature, and washed with TBS-Triton. Slides were then incubated with biotin-labelled rabbit anti-rat Ig (1/100, DAKO (Australia) PTY LTD, Botany, Australia) for 30 min at room temperature, followed by horseradish peroxidase-labelled (HRP)-Streptavidin (Jackson ImmunoResearch Laboratories Inc.) 30 min and visualized using the substrate 3,3' diaminobenzidine (DAB) (Vector laboratories, Inc., Burlingame, Calif.). Sections were counterstained using hematoxylin (Sigma) and Scott's blueing solution and dehydrated in successive baths of $H_2O$, 100% ethanol and xylene. Slides were mounted with cover slips and Eukitt mounting solution (Calibrated Instruments Inc., Hawthorne, N.Y.). Endogenous peroxidase activity was blocked using 2% hydrogen peroxide in methanol for 20 min before staining with the primary antibody. Frozen sections of spleen and submaxillary glands were subjected to immunohistochemical analysis as previously described (32). Biotin-labelled anti-mouse B220 and anti-mouse Syndecan-1 were purchased from BD PharMingen and the staining was detected using HRP-streptavidin (Jackson ImmunoResearch Laboratories Inc.) and visualized using DAB. All slides were observed under a Leica light microscope and images were captured using a Leica DC 200 camera (Leica, Bannockburn, Ill.).

Scoring of SS Disease Activity in Mice.

Tissue sections of mouse submaxillary glands stained with H&E were examined at 100× under the microscope and scored as previously described. (White et al. (1974) *J. Immunol.* 112:178-185). The degree of inflammatory infiltrates is graded as follows: 1 indicated that 1 to 5 foci of mononuclear cells were seen (more than 20 cells per focus), 2 indicated that more than 5 foci of mononuclear cells were seen but without significant parenchymal destruction, 3 indicated that multiple confluent foci were seen with moderate degeneration of parenchymal tissue and 4 indicated extensive infiltration of the gland with mononuclear cells and extensive parenchymal destruction.

Measurement of Salivary Flow.

Mice were anaesthetized and injected ip with 50 µg of sterile pilocarpine in PBS (Sigma, St Luis, Mo.) per 100 g body weight. After 4 min, saliva was collected for 5 min on a cotton swab. The weight of the cotton swab was measured before and after saliva collection. The amount of saliva collected was normalized to □g of saliva per g of body weight.

Patients with Primary SS and Sera.

Sera were Collected from 41 Patients Followed Between 1995 and 2001 at Flinders Medical Centre who fulfilled at least four of six European consensus criteria for the diagnosis of primary SS. (Vitali et al. (1993) *Arthritis Rheum.* 36:340-347. No patient was treated with corticosteroids or immunosuppressive agents. Control sera were collected from 39 healthy donors. Labial salivary gland biopsies with lymphocyte focus scores of >1 per 4 $mm^2$ of salivary gland tissue were obtained from 4 patients with primary SS (Chisholm, et al. (1968) *J. Clin. Pathol.* 21:656-660), and histologically normal labial salivary gland tissues obtained from 3 controls.

ELISA Assays for Detection of Human BAFF in Sera from Patients with Primary SS.

Sera from patients were diluted 1/10 and precleared from human Ig on protein-A-Sepharose beads (10% beads (pelleted beads) v/v, Amersham Pharmacia) overnight at 4° C. ELISA plates (NUNC Nalge International, Rochester, N.Y.) were coated with 2 µg/ml rat anti-human BAFF antibody (Buffy-5), overnight at 4° C. Following blocking, serial dilutions of the precleared sera were added, followed by the detection antibody, biotin-conjugated mouse anti-human BAFF (0.5 µg/ml, clone A21G3.3), Alkaline phosphatase (AP)-labelled streptavidin (AP-SA, Jackson ImmunoResearch Laboratories Inc.) and the corresponding AP substrate Sigma 104 (Sigma) were used for detection. The reaction was stopped using 3N NaOH. Plates were read at an OD of 405 nm, and a standard curve was generated using known quantities of recombinant human BAFF diluted in human serum and treated as described above for patients' samples. Statistical analyses were done using the StatView software and ANOVA.

Example 7

BAFF Tg Mice Develop a Sjögren-Like Syndrome with Age

Figure 14A:
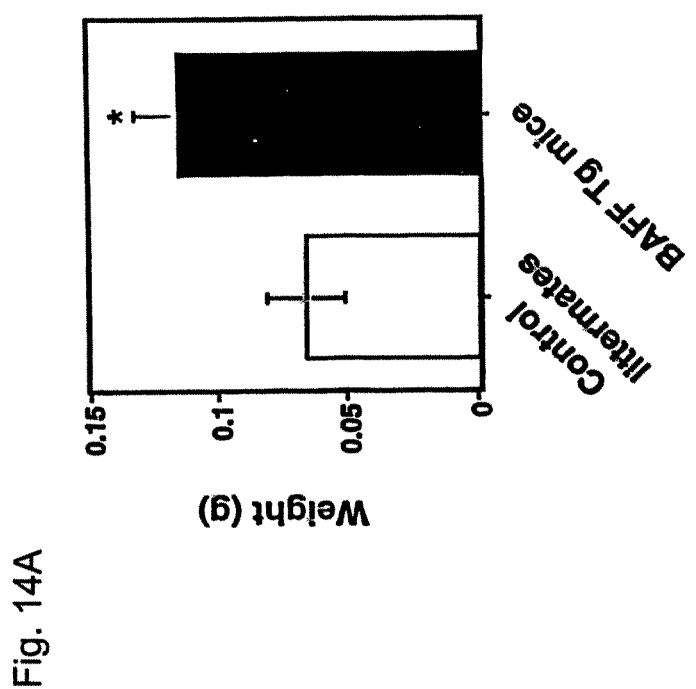

Following routine dissections of more than 50 BAFF Tg mice and over 20 age-matched littermate controls, we observed that many mice over age 13 months had enlarged salivary (submaxillary) glands (FIG. 14A). Histological preparations from 22 BAFF Tg mice 12-17 months-old and 7 age-matched control mice were examined and scored for disease severity. The scoring system used (White et al.) takes into consideration the number of foci of infiltrating leukocytes in the gland and the extent of destruction of the parenchymal tissue.

Figure 14B:
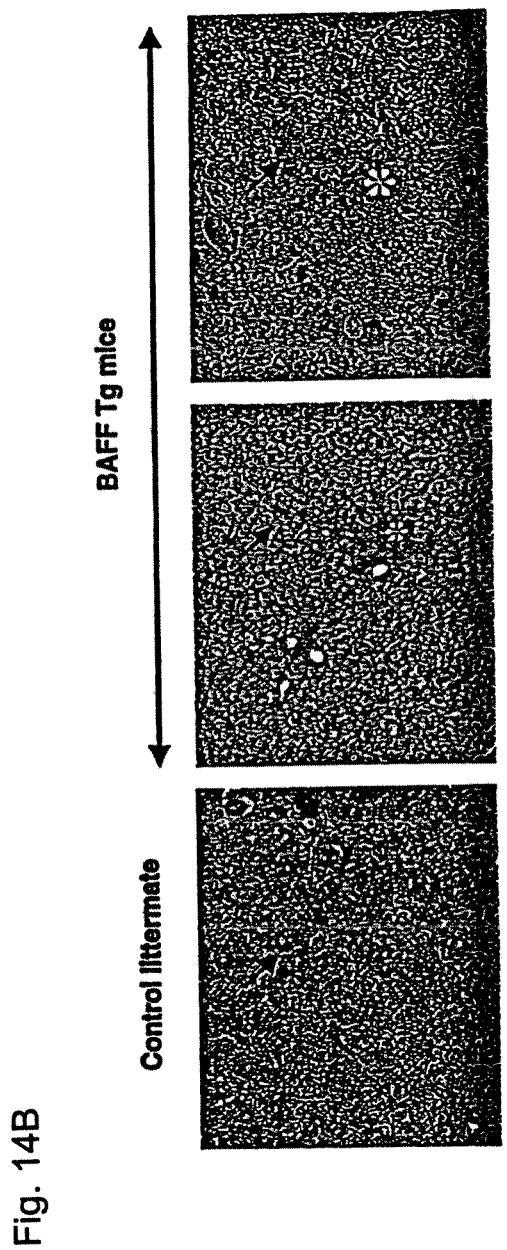
Figure 14C:
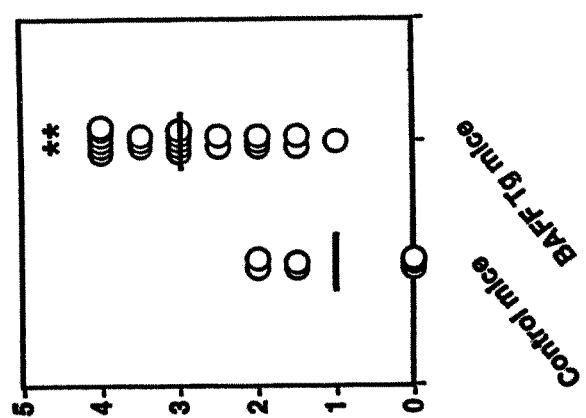

A massive destruction of epithelial duct/acinar cells with small periductal foci, as well as large leukocytic infiltrates, was observed in submaxillary glands from BAFF tg animals (FIG. 14B, middle and right panel). Although small foci of infiltrating leukocytes were detected in the submaxillary glands of age-matched control mice, disease grades remained between 0 and 2, while the majority of BAFF tg mice scored 3 or greater. Overall, our analysis revealed that 40% of BAFF Tg mice over 12 months of age exhibited severe disease (grade 3 or above, FIG. 14C), an incidence which is significantly greater than that observed for control mice (FIG. 14C). Furthermore, the pathology observed in the BAFF tg mice was independent of the sex of the animals (data not shown). Lacrimal glands were not examined as mice did not develop obvious ocular disorders (keratoconjunctivitis).

Example 8

Presence of Tumor-Like Infiltrates in Salivary Glands of BAFF Tg Mice

Interestingly. 3 BAFF Tg mice between 13 and 15 months-old, developed a large submaxillary tumor (over 1 cm of diameter), while no such tumors were observed in age-matched controls. Histological analysis revealed that these tumors contained hyperplastic lymphoid tissue composed mainly of activated B-lymphocytes (FIG. 15D) and numerous germinal centers (FIG. 15B). It is not known whether the tumors arose from infiltrates within submaxillary glands or from neighbouring lymph nodes, as no remaining glandular tissue was evident by histology. However, as only one submaxillary gland was found in these mice, it is likely that the tumors arose from infiltrates within the gland which ultimately overwhelmed and destroyed all glandular tissue. Unusual aggregates of cells organised in diffused foci (small lymphocytes in sinusoids) (FIGS. 15A, B and C) were detected in these tumors (FIG. 15B), as well as in the large leukocyte infiltrates-found in salivary glands of 4 independent BAFF Tg mice (two examples are shown in FIGS. 15A and C). Cells in these infiltrates were B-lymphoid cells expressing high levels of B220 (FIG. 15D), however they were not plasma cells since they were not positive for the plasma cell marker, syndecan-1 (FIG. 15E). A consulting pathologist indicated that because no lympho-epithelial aggregates were seen, the infiltrating B cells could not be definitively classified as malignant. Studies to examine the clonality of these unusual B cells are in progress to determine whether they are simply tumor-like clusters of lymphoid cells that do not meet criteria for malignancy or cells with real neoplastic potential Example 9

Submaxillary Glands from Older BAFF Tg Mice are Infiltrated by a Large Number of B-Lymphocytes Seven BAFF Tg mice that had significantly larger submaxillary glands compared to age-matched control mice were selected for a detailed assessment of infiltrating cells. One gland from each mouse was digested with collagenase, after which mononuclear-cells were purified and analysed by flow cytometry. Absolute counts of various cell types showed a consistent and significant increase in the number of B-lymphocytes infiltrating submaxillary glands of aging BUFF Tg mice (Table 1). Numbers of T cells, NK cells, macrophages and granulocytes also increased, however a large variation was seen between animals (Table 1). Hematoxylin and eosin staining done on the second gland collected from each Tg animal confirmed that the disease score on these tissues was at least 3 (data not shown). Mice with severe lesions in their submaxillary glands (disease grade above 3) did not secrete anti-Ro/SSA and/or anti-La/SSB autoantibodies, which are often associated with human SS (data not shown).

TABLE 1

Analysis of leukocytes present in salivary glands of BAFF transgenic mice and control littermates by flow cytometry.

| | Age (months) | Total Leukocytes ($\times 10^6$) | B cells ($\times 10^6$) | CD4+ T cells ($\times 10^6$) | CD8+ T cells ($\times 10^6$) | NK cells ($\times 10^6$) | Mac-1+ cells ($\times 10^6$) | GRI+ cells ($\times 10^6$) |
|---|---|---|---|---|---|---|---|---|
| Control Littermates | | | | | | | | |
| Control 1 | 14 | 8.4 | 0.048 | — | ND | 0.04 | 0.22 | ND |
| Control 2 | 14 | 5.6 | 0.045 | — | ND | 0.03 | 0.17 | ND |
| Control 3 | 14 | 5.9 | 0.028 | — | ND | 0.02 | 0.23 | ND |
| Control 4 | 15 | 1.5 | 0.0014 | 0.0082 | 0.0011 | 0.02 | 0.57 | 0.062 |
| Mean ± SD | 14.25 ±0.5 | 5.35 ±2.8 | 0.03 ±0.02 | | | 0.027 ±0.009 | 0.29 ±0.18 | |
| BAFF Tg mice | | | | | | | | |
| BAFF Tg1 | 14 | 30 | 1.1 | — | ND | 0.27 | 0.7 | ND |
| BAFF Tg2 | 14 | 31.7 | 0.14 | — | ND | 0.31 | 1.03 | ND |
| BAFF Tg3 | 16 | 42.3 | 0.6 | — | ND | 0.02 | 0.23 | ND |
| BAFF Tg4 | 8 | 6 | 0.35 | 0.039 | 0.028 | 0.13 | 0.29 | 0.45 |
| BAFF Tg5 | 16 | 11 | 4.6 | 0.084 | 1.6 | 0.64 | 0.27 | 43 |
| BAFF Tg6 | 17 | 2.5 | 0.03 | 0.027 | 0.022 | 0.087 | 0.17 | 0.23 |
| BAFF Tg7 | 16 | 22 | 9.3 | 0.34 | 1.6 | 1.4 | 0.5 | 8.7 |
| Mean ± SD | 14.4 | 21 | 2.3 | | | 0.41 | 0.46 | |

TABLE 1-continued

Analysis of leukocytes present in salivary glands of BAFF transgenic mice and control littermates by flow cytometry.

| | Age (months) | Total Leukocytes ($\times 10^6$) | B cells ($\times 10^6$) | CD4+ T cells ($\times 10^6$) | CD8+ T cells ($\times 10^6$) | NK cells ($\times 10^6$) | Mac-1+ cells ($\times 10^6$) | GRI+ cells ($\times 10^6$) |
|---|---|---|---|---|---|---|---|---|
| | ±3 | ±14 | ±3.5 | | | ±0.5 | ±0.31 | |
| p values | | $P < 0.05$ | $P < 0.05$ | | | | | |

Animals were sacrificed and submaxillary glands dissected. Tissues were digested and leukocytes purified as described in materials and methods. The Total number of leukocytes per gland was counted using an hemocytometer. Cells were stained with anti-B220 (B cells), anti-CD4 and anti-CD8 (T cells), anti-NK1.1 (NK cells), anti-Mac1 (macrophages) and anti-GR1 (granulocytes) fluorochrome-labelled antibodies. Flow cytometry analysis provided percentage values for each subpopulation of cells and absolute numbers were calculated relative to the total number of cells collected per gland. ND: not detected, -: not done. Only significant p values are indicated.

Example 10

Figure 16A:
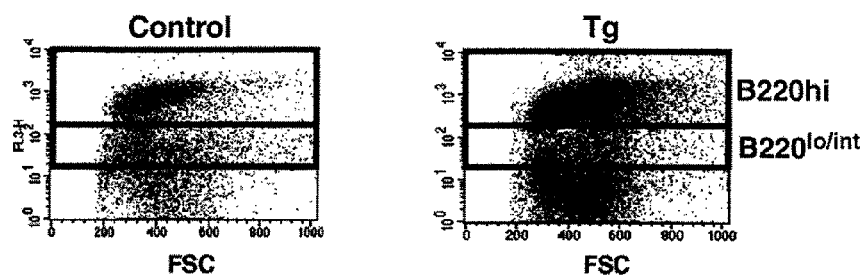
Figure 16B:
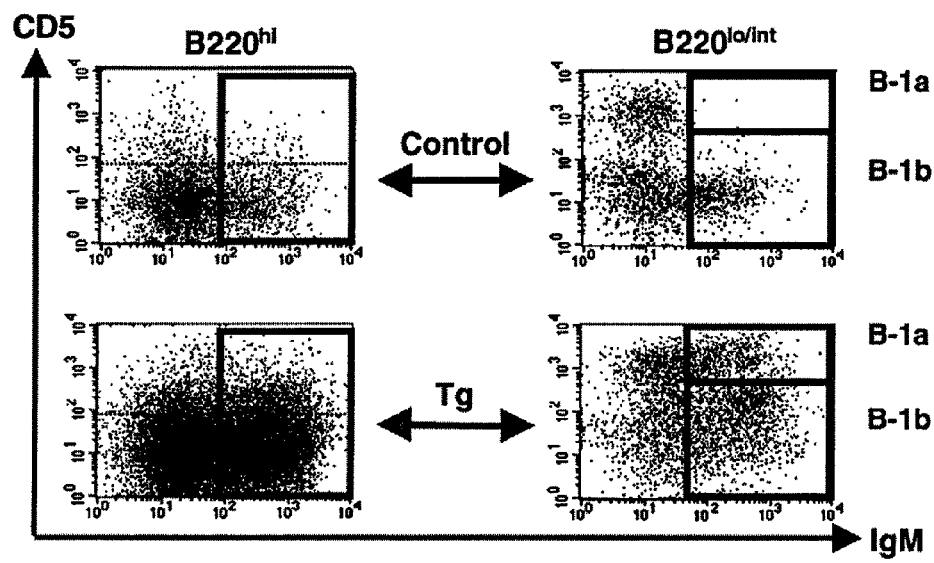
Figure 16C:
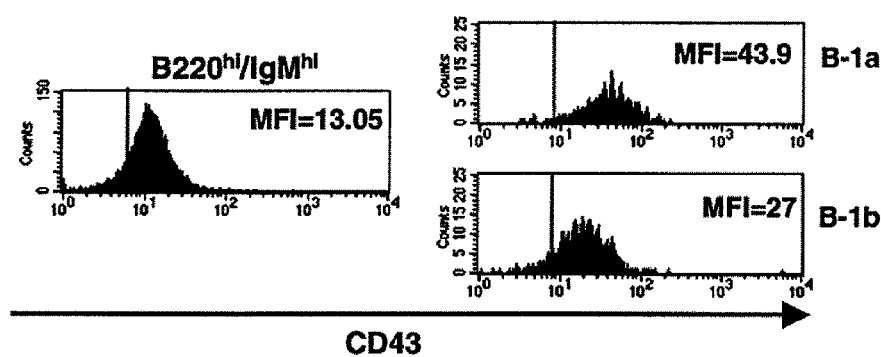
Figure 16D:
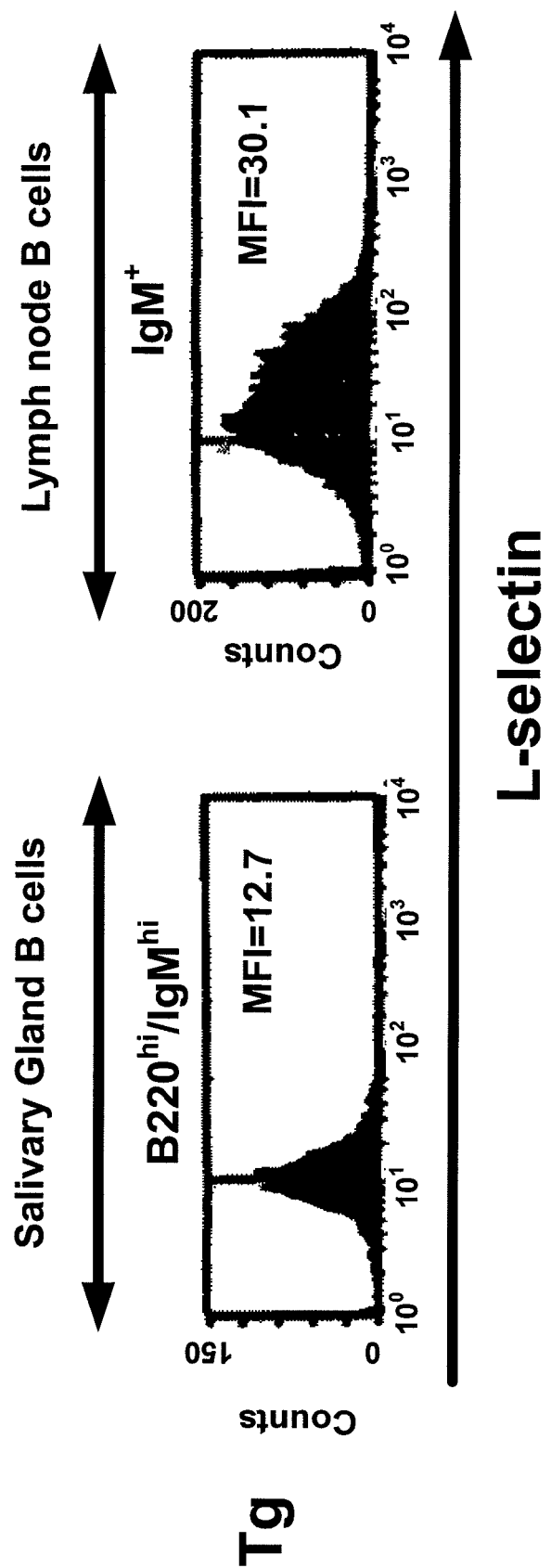
Figure 16E:
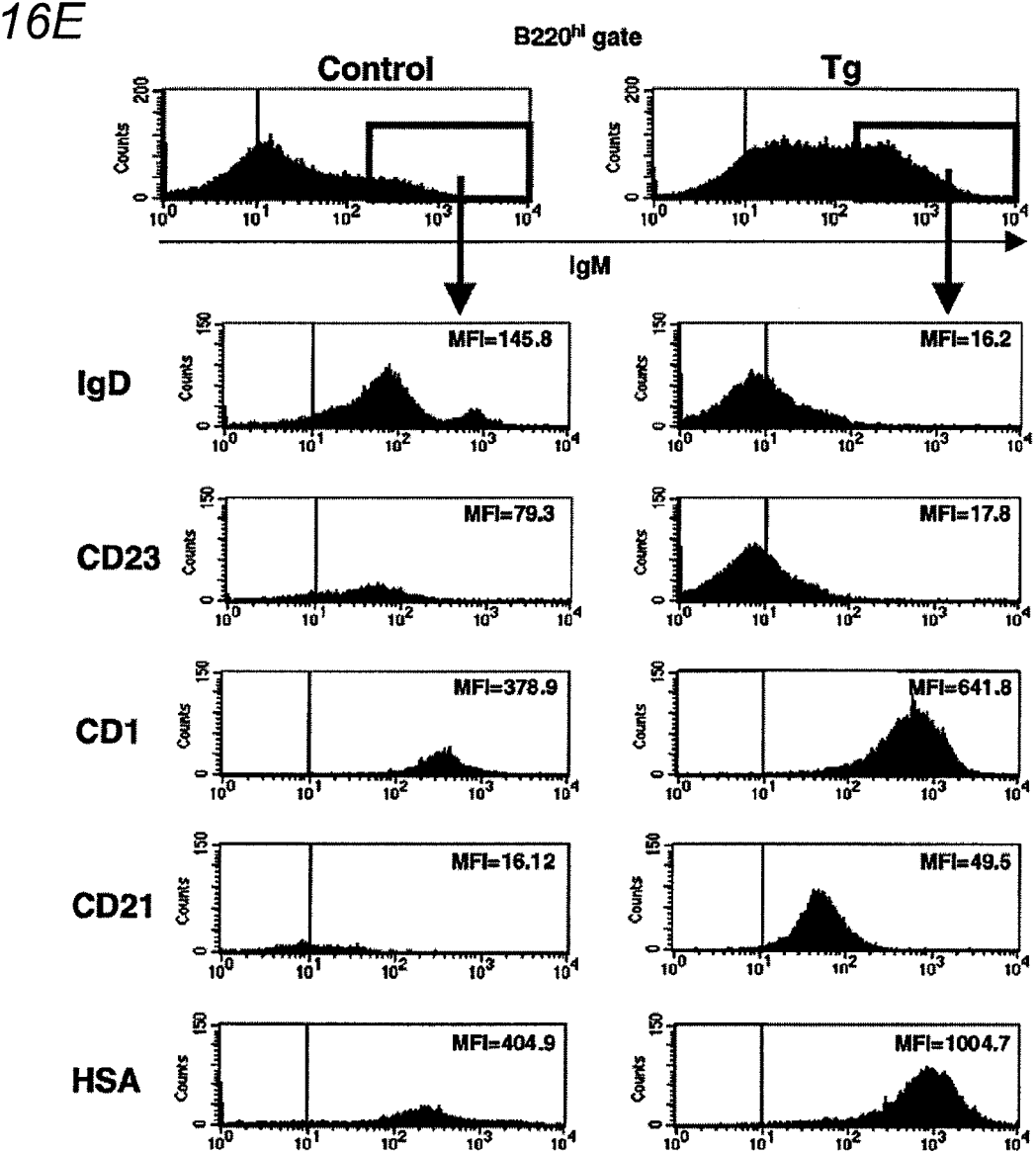
Figure 16F:
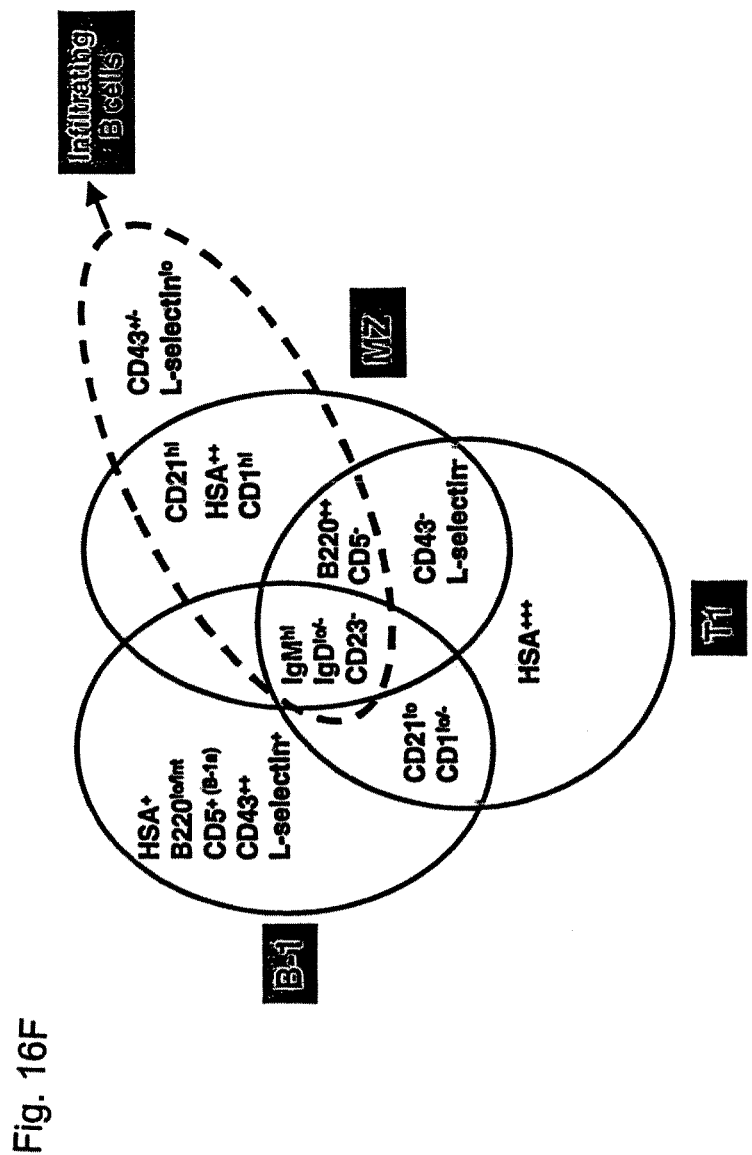

A Large Proportion of B Cells Infiltrating Submaxillary Glands of BAFF Tg Mice have a Marginal Zone (MZ)-Like Phenotype A flow cytometric profiling analysis of B cells infiltrating the submaxillary glands of BAFF Tg mice revealed two B cell subsets based on their level of expression of B220 (FIG. 16A). Analysis of the B-1 B cell population in the B220 low/intermediate ($B220^{lo/int}$) gate revealed a 3-fold increase of B-1b ($CD5^-$) B cells and presence of B-1a ($CD5^+$) B cells not detected in control mice (FIG. 16B). In the B220 high ($B220^{hi}$) gate, cells were further analysed based on their level of IgM expression. The IgM dull ($IgM^{dull}$) subset of B cells is present in both control and BAFF Tg mice, however this population is larger in BAFF Tg mice compared to control animals (FIG. 16B). The $IgM^{dull}$ subset in both control and BAFF Tg mice contains B-2-like cells, which are $CD21^{lo/int}$, $IgD^+$ and $CD23^+$ (data not shown). The $B220^{hi}/IgM^{hi}$ B cell subset is greatly increased in BAFF Tg mice compared to control mice (FIG. 16B). Moreover, the $IgM^{hi}$ B cells found in BAFF Tg mice are phenotypically different than $IgM^{hi}$ B cells from control mice. Indeed, the small $IgM^{hi}$ B cell subset detected in control mice had characteristics of B-2 B cells ($CD21^{lo/int}$, $IgD^+$ and $CD23^+$, add HSA and L-selectin (FIGS. 16D, 16E), whereas the large $IgM^{hi}$ B cell subset of BAFF Tg mice had no counterpart in control mice and resembled MZ B cells in many respects. These cells were $IgD^{lo}$, $CD-21^{hi}$, $CD23^{lo/-}$, $CD1^{hi}$, $HSA^{++}$ (FIG. 16E) and L-selectin$^{lo}$ (FIG. 16D). These cells also express lower levels of CD43 when compared to B-1 B cells (FIG. 16C). We therefore refer to these cells as MZ-like B-cells because their profile is closer to that of MZ B cells than to other phenotypically-related B cell subsets such as B-1 and splenic transitional T1 B cells (FIG. 16F). (Wells et al. (1994) *J. Immunol.* 153:5503-5515; Amano et al. (1998) *J. Immunol.* 161:1710-1717). However, these cells also share some similarities with B-1b cells, such as low expression of D43.

Example 11

Older BAFF Tg Mice Exhibit Impaired Saliva Production

The inflammation seen in the salivary glands of BAFF Tg mice was reminiscent of the inflammation described for SS patients. Therefore, we aimed to determine if the inflammation in BAFF Tg mice caused an impairment of normal saliva production. To this end, 13 BAFF Tg mice and 14 control littermates between 8 and 15.5 months of age received pilocarpine, a known stimulant for salivary flow, 4 min prior to the collection and measurement of saliva We found that mice between 13 and 15 months of age had a significantly reduced production of saliva when compared to age-matched control animals (FIG. 17A). However, this difference was not seen with mice between 8 and 10 months of age (FIG. 17B). Interestingly, reduction in saliva flow correlated with the highest numbers of B-lymphocytes detected in submaxillary-glands of these Tg animals (data not shown).

Example 12

Figure 18A:
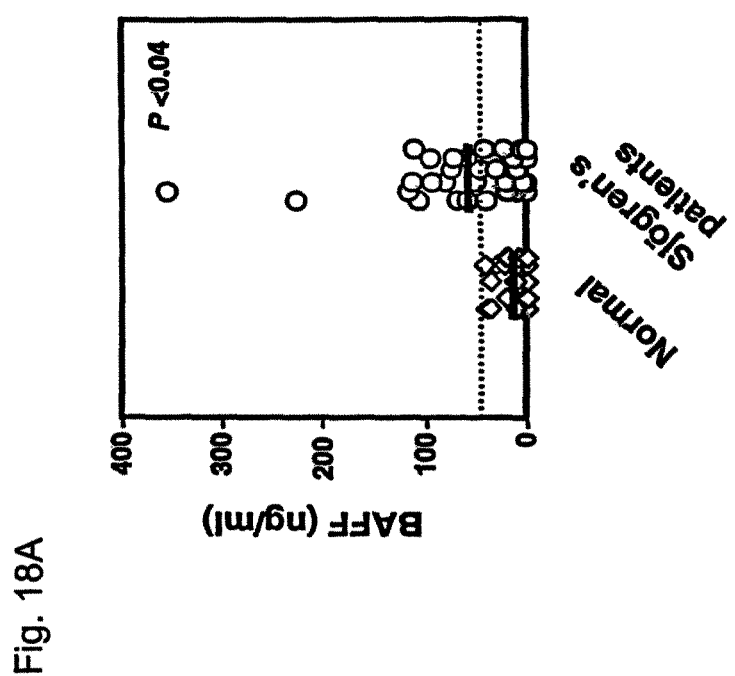
Figure 18C:
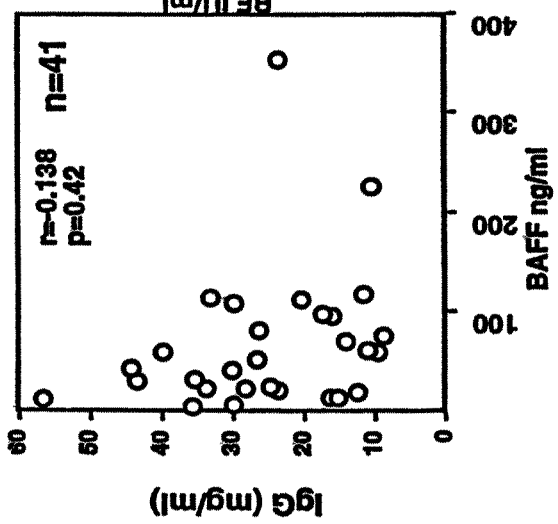
Figure 18B:
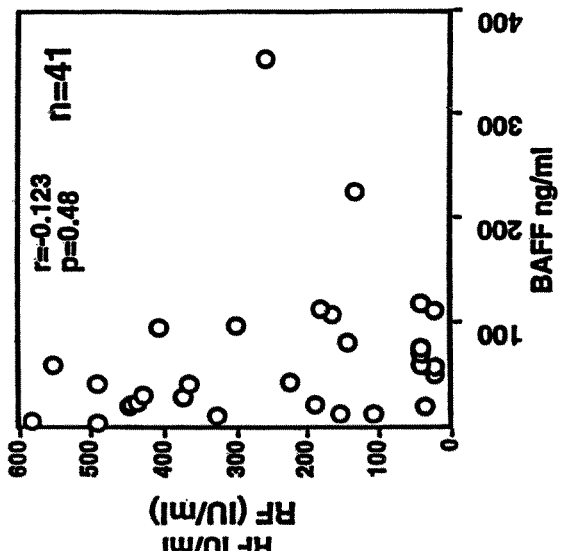
Figure 18D:
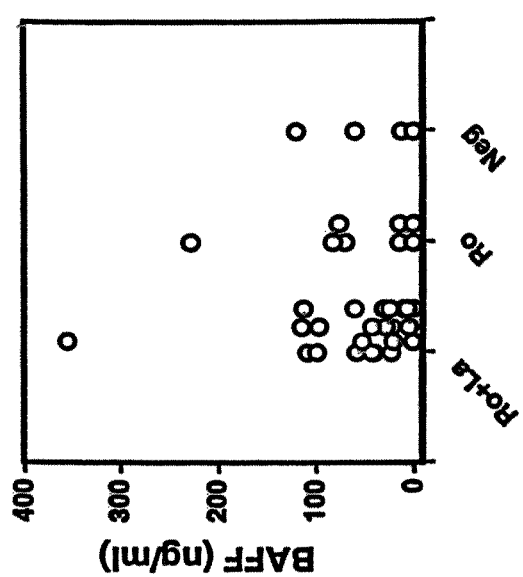

Elevated Levels of BAFF Detected in the Serum of Patients Suffering from Primary Sjögren's Syndrome As the Sjögren's-like pathology observed in some BAFF Tg mice showed similar features to human SS, we measured BAFF levels in sera of patients suffering from this disease. Sera from 41 patients with primary SS and 39 healthy individuals were analysed using a human BAFF-specific ELISA assay. This assay showed that at least 15 patients out of 41 (36%) clearly had higher levels of serum BAFF when compared to healthy individuals (FIG. 18A). Two patients had very high BAFF levels (over 200 ng/ml, FIG. 18A). BAFF levels in patients' sera did not correlate with the levels of total IgG or RF (FIGS. 18B and C, respectively). These BAFF levels also did not correlate with the presence of precipitins such as anti-Ro and/or anti-La (FIG. 18D). We confirmed human BAFF levels in patients' sera using BAFF-specific immunoprecipitation procedures followed by western blotting techniques (data not shown).

Example 13

Figure 18E:
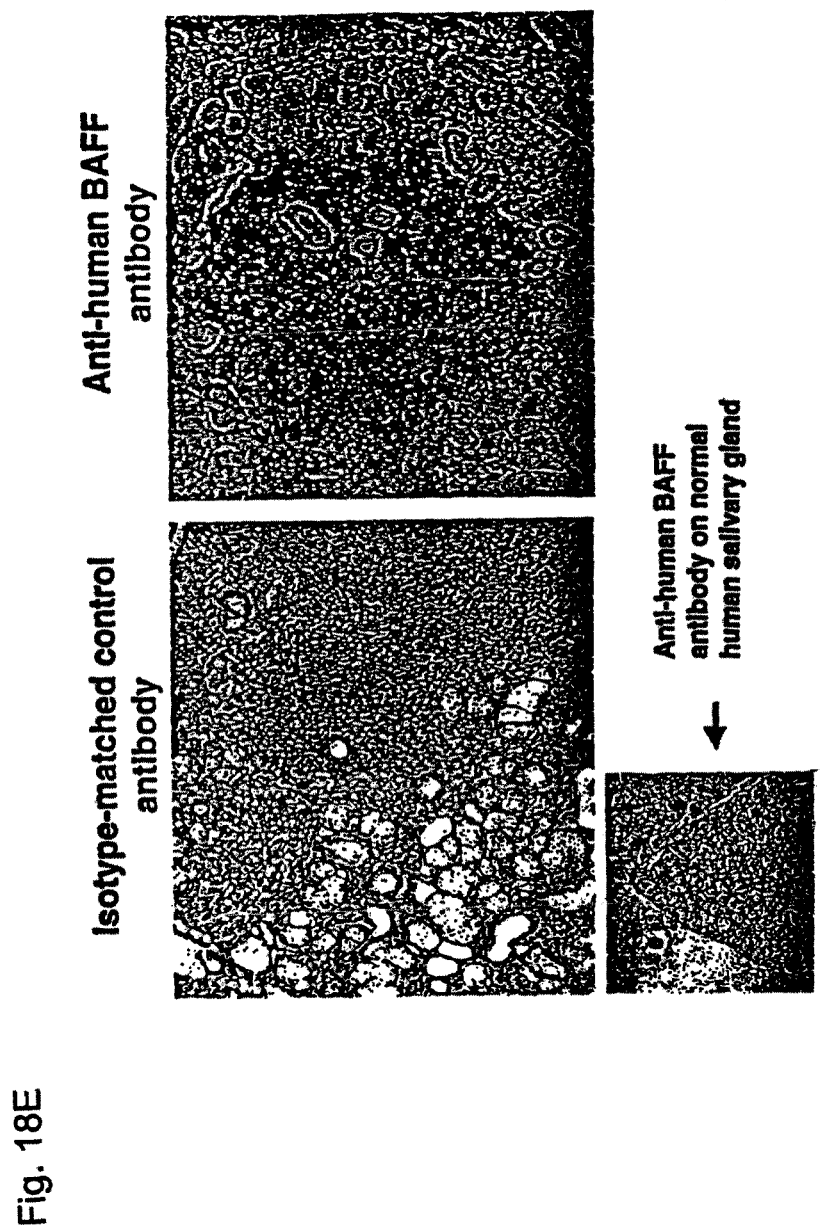

Detection of BAFF Expressing Cells in Tissue Sections from Labial Glands of Patients with SS We examined the expression of BAFF at the site of abnormal lymphocyte infiltrates in biopsies of labial glands from SS patients. A strong BAFF+ signal was detected on leukocytic infiltrates within patient tissues, although clearly not all cells were positive for BAFF within the infiltrate (FIG. 18E, right panel). The positive signal detected was specific since it could be competed away by the addition of recombinant human BAFF (data not shown). The antibody did not stain normal labial salivary gland tissue (FIG. 18E, bottom left). Preliminary experiments using 2-color staining on tissues indicate that infiltrating macrophages/monocytes are the likely source of BAFF in these inflamed tissues (data not shown).

REFERENCES

1. Smith et al. (1994) *Cell* 76:959-962.
2. Vassalli (1992) *Annu. Rev. Immunol.* 10:411-452.
3. De Togni et al. (1994) *Science* 264:703-707.
4. Koni et al. (1997) *Immunity* 6:491-500.
5. Amakawa et al. (1996) *Cell* 84:551-562.
6. Russell et al. (1993) *Proc. Natl. Acad. Sci. USA* 90:4409-4413.
7. Zheng et al. (1995) *Nature* 377:348-351.
8. van Kooten and Banchereau (1997) *Curr. Opin. Immunol.* 9:330-337.
9. Stuber and Strober (1996). *J. Exp. Med.* 183:979-989.
10. Schneider et al. (1997) *J. Biol. Chem.* 272:18827-18833.
11. Hahne et al. (1998) *J. Exp. Med.* 188:1185-1190.
12. Hahne et al. (1996) *Science* 274:1363-1366.
13. Grimaitre et al. (1997) *Eur. J. Immunol.* 27:199-205.
14. Thome et al. (1997) *Nature* 386:517-521.
15. Schneider et al. (1998) *J. Exp. Med.* 187:1-205-1213.
16. Matsudaira, P. (1987) *J. Biol. Chem.* 262:10035-10038.
17. Armitage et al. (1992) *Nature* 357:80-82.
18. Bucher et al. (1996) *Computer Chem.* 20:3-24.
19. Banner et al. (1993) *Cell* 73:431-445.
20. Nagata (1997) *Cell* 88:355-365.
21. Black-et al. (1997) *Nature* 385:729-733.
22. Wong et al. (1997) *J. Biol. Chem.* 272:25190-25194.
23. Kindler and Zubler. (1997) *J. Immunol.* 159:2085-2090.
24. Sonoki et al. (1995) *Leukemia* 9:2093-2099.
25. Magrath, I. (1990) *Adv Cancer Res* 55:133-270.
26. Garside et al. (1998) *Science* 281:96-99.
27. MacLennan et al. (1997) *Immunol. Rev.* 156:53-66.
28. Dubois et al. (1997). *J. Exp. Med.* 185:941-951.
29. Tsubata et al. (1993) *Nature* 364:645-648.
30. Chicheportiche et al. (1997) *J. Biol. Chem.* 272:32401-32410.
31. Nakayama (1997) *Biochem. J.* 3, 27:625-635.
32. Jefferis, R. (1995). Rheumatoid factors, B cells and immunoglobulin genes. Br. Med. Bull. 51, 312-331.
33. Schneider et al. (1999) *J. Exp. Med.* 189, 1747-1756.
34. Mcknights et al. (1983) Cell 34, 335-341.
35. Datta et al. (1987) J. Exp. Med. 165, 1252-1261.

What is claimed is:

1. A method of treating a mammal, the method comprising administering to a mammal having Sjögren's syndrome a composition comprising a BAFF blocking agent selected from the group consisting of:
   (a) a soluble BAFF receptor selected from a BAFF-R:Fc fusion, a BCMA:Fc fusion, and a TACI:Fc fusion; and
   (b) an antibody against a BAFF receptor selected from BAFF-R, BCMA, and TACI,
thereby reducing immunoglobulin production or B cell growth in the mammal.

2. The method of claim 1, wherein the mammal is a human.

3. The method of claim 1, wherein the mammal is a mouse.

4. The method of claim 3, wherein the mouse is a BAFF Tg mouse.

5. The method of claim 1, wherein the salivary gland of the mammal is infiltrated by MZ like B cells.

6. The method of claim 1, wherein the BAFF receptor is BAFF-R.

7. The method of claim 1, wherein the BAFF receptor is TACI.

8. The method of claim 1, wherein the BAFF receptor is BCMA.

9. The method of claim 6, wherein the BAFF-R is human.

10. The method of claim 1, wherein the soluble BAFF receptor comprises a portion of SEQ ID NO:27 that binds to BAFF.

11. The method of claim 6, wherein the BAFF-R is murine.

12. The method of claim 1, wherein the soluble BAFF receptor comprises a portion of SEQ ID NO:28 that binds to BAFF.

13. The method of claim 1, further comprising detecting the level of B cell growth in the mammal.

14. The method of claim 1, further comprising detecting the level of immunoglobulin production in the mammal.

15. The method of claim 1, further comprising detecting the levels of B cell growth and immunoglobulin production in the mammal.

16. The method of claim 1, further comprising detecting circulating levels of a rheumatoid factor in the mammal.

17. The method of claim 1, further comprising detecting circulating levels of anti-DNA autoantibody in the mammal.

* * * * *

UNITED STATES PATENT AND TRADEMARK OFFICE
CERTIFICATE OF CORRECTION

PATENT NO. : 9,545,086 B2  
APPLICATION NO. : 12/061398  
DATED : January 17, 2017  
INVENTOR(S) : Fabienne MacKay et al.

Page 1 of 1

It is certified that error appears in the above-identified patent and that said Letters Patent is hereby corrected as shown below:

On the Title Page

After "Related U.S. Application Data", the paragraph labeled Item (60), is replaced with the following new paragraphs:

(60) Divisional of application No. 11/065,669, filed on Feb. 24, 2005, now abandoned, which is a continuation of application No. 10/045,574, filed on Nov. 7, 2001, now abandoned, which is a continuation-in-part of application No. 09/911,777, filed on Jul. 24, 2001, now U.S. Pat. No. 6,869,605, which claims a continuation of PCT application No. PCT/US2000/001788, filed on Jan. 25, 2000.

Provisional application No. 60/117,169, filed on Jan. 25, 1999, and Provisional application No. 60/143,228, filed on July 9, 2001.

Signed and Sealed this  
Ninth Day of May, 2017

Michelle K. Lee  
*Director of the United States Patent and Trademark Office*

SEQUENCE LISTING

```
<160> NUMBER OF SEQ ID NOS: 28

<210> SEQ ID NO 1
<211> LENGTH: 218
<212> TYPE: PRT
<213> ORGANISM: Homo sapiens

<400> SEQUENCE: 1

Met Asp Asp Ser Thr Glu Arg Glu Gln Ser Arg Leu Thr Ser Cys Leu
  1               5                  10                  15

Lys Lys Arg Glu Glu Met Lys Leu Lys Glu Cys Val Ser Ile Leu Pro
             20                  25                  30

Arg Lys Glu Ser Pro Ser Val Leu Leu Ser Cys Cys Leu Thr Val Val
         35                  40                  45

Ser Phe Tyr Gln Val Ala Ala Leu Gln Gly Asp Leu Ala Ser Leu Arg
     50                  55                  60

Ala Glu Leu Gln Gly His His Ala Glu Lys Leu Pro Ala Gly Ala Lys
 65                  70                  75                  80

Ile Phe Glu Pro Pro Ala Pro Gly Glu Gly Asn Ser Ser Gln Asn Ser
                 85                  90                  95

Arg Asn Lys Arg Ala Val Gln Gly Pro Glu Glu Thr Val Thr Gln Asp
            100                 105                 110

Cys Leu Gln Leu Ile Ala Asp Ser Glu Thr Pro Thr Ile Gln Lys Gly
        115                 120                 125

Ser Tyr Thr Phe Val Pro Trp Leu Leu Ser Phe Lys Arg Gly Ser Ala
    130                 135                 140

Leu Tyr Gly Gln Val Leu Tyr Thr Asp Lys Thr Tyr Ala Met Gly His
145                 150                 155                 160

Leu Ile Gln Arg Lys Lys Val His Val Phe Gly Asp Glu Leu Ser Leu
                165                 170                 175

Val Thr Leu Phe Arg Cys Ile Gln Asn Leu Glu Glu Gly Asp Glu Leu
            180                 185                 190

Gln Leu Ala Ile Pro Arg Glu Asn Ala Gln Ile Ser Leu Asp Gly Asp
        195                 200                 205
```

```
Val Thr Phe Phe Gly Ala Leu Lys Leu Leu
    210                 215
```

```
<210> SEQ ID NO 2
<211> LENGTH: 232
<212> TYPE: PRT
<213> ORGANISM: Mus sp.

<400> SEQUENCE: 2

Met Asp Glu Ser Ala Lys Thr Leu Pro Pro Cys Leu Cys Phe Cys
  1               5                  10                  15

Ser Glu Lys Gly Glu Asp Met Lys Val Gly Tyr Asp Pro Ile Thr Pro
                 20                  25                  30

Gln Lys Glu Glu Gly Ala Val Leu Leu Ser Ser Ser Phe Thr Ala Met
             35                  40                  45

Ser Leu Tyr Gln Leu Ala Ala Leu Gln Ala Asp Leu Met Asn Leu Arg
         50                  55                  60

Met Glu Leu Gln Ser Tyr Arg Gly Ser Ala Thr Pro Ala Ala Ala Lys
 65                  70                  75                  80

Leu Leu Thr Pro Ala Ala Pro Arg Pro His Asn Ser Ser Arg Gly His
                 85                  90                  95

Arg Asn Arg Arg Ala Phe Pro Gly Pro Glu Thr Glu Gln Asp Val
                100                 105                 110

Asp Leu Ser Ala Pro Pro Ala Leu Arg Asn Ile Ile Gln Asp Cys Leu
            115                 120                 125

Gln Leu Ile Ala Asp Ser Asp Thr Pro Thr Ile Arg Lys Gly Thr Tyr
        130                 135                 140

Thr Phe Val Pro Trp Leu Leu Ser Phe Lys Arg Gly Asn Ala Leu Tyr
145                 150                 155                 160

Ser Gln Val Leu Tyr Thr Asp Pro Ile Phe Ala Met Gly His Val Ile
                165                 170                 175

Gln Arg Lys Lys Val His Val Phe Gly Asp Glu Leu Ser Leu Val Thr
            180                 185                 190

Leu Phe Arg Cys Ile Gln Asn Leu Glu Glu Gly Asp Glu Ile Gln Leu
        195                 200                 205

Ala Ile Pro Arg Glu Asn Ala Gln Ile Ser Arg Asn Gly Asp Asp Thr
    210                 215                 220

Phe Phe Gly Ala Leu Lys Leu Leu
225                 230
```

```
<210> SEQ ID NO 3
<211> LENGTH: 102
<212> TYPE: PRT
<213> ORGANISM: Homo sapiens

<400> SEQUENCE: 3

Val Thr Gln Asp Cys Leu Gln Leu Ile Ala Asp Ser Glu Thr Pro Thr
  1               5                  10                  15

Ile Gln Lys Gly Ser Tyr Thr Phe Val Pro Trp Leu Leu Ser Phe Lys
                 20                  25                  30

Arg Gly Ser Ala Leu Glu Glu Lys Tyr Gly Gln Val Leu Tyr Thr Asp
             35                  40                  45

Lys Thr Tyr Ala Met Gly His Leu Ile Gln Arg Lys Lys Val His Val
         50                  55                  60

Phe Gly Asp Glu Leu Ser Asn Asn Ser Cys Tyr Ser Ala Gly Ile Ala
 65                  70                  75                  80
```

```
Lys Leu Glu Glu Gly Asp Glu Leu Gln Leu Ala Ile Pro Arg Glu Asn
                85                  90                  95

Ala Gln Ile Ser Leu Asp
            100

<210> SEQ ID NO 4
<211> LENGTH: 96
<212> TYPE: PRT
<213> ORGANISM: Homo sapiens

<400> SEQUENCE: 4

Lys Gln His Ser Val Leu His Leu Val Pro Ile Asn Ala Thr Ser Lys
  1               5                  10                  15

Asp Asp Ser Asp Val Thr Glu Val Met Trp Gln Pro Ala Leu Arg Arg
                20                  25                  30

Gly Arg Gly Leu Gln Ala Gln Tyr Ser Gln Val Leu Phe Gln Asp Val
            35                  40                  45

Thr Phe Thr Met Gly Gln Val Val Ser Arg Glu Gly Gln Gly Arg Ala
        50                  55                  60

Tyr Asn Ser Cys Tyr Ser Ala Gly Val Phe His Leu His Gln Gly Asp
 65                  70                  75                  80

Ile Leu Ser Val Ile Ile Pro Arg Ala Arg Ala Lys Leu Asn Leu Ser
                85                  90                  95

<210> SEQ ID NO 5
<211> LENGTH: 104
<212> TYPE: PRT
<213> ORGANISM: Homo sapiens

<400> SEQUENCE: 5

Ser Asp Lys Pro Val Ala His Val Val Ala Asn Pro Gln Ala Glu Gly
  1               5                  10                  15

Gln Leu Gln Trp Leu Asn Arg Arg Ala Asn Ala Leu Leu Ala Asn Gly
                20                  25                  30

Val Tyr Ser Gln Val Leu Phe Lys Gly Gln Gly Cys Pro Ser Thr His
            35                  40                  45

Val Leu Leu Thr His Thr Ile Ser Arg Ile Ala Val Ser Tyr Gln Thr
        50                  55                  60

Glu Gly Ala Glu Ala Lys Pro Trp Tyr Glu Pro Ile Tyr Leu Gly Gly
 65                  70                  75                  80

Val Phe Gln Leu Glu Lys Gly Asp Arg Leu Ser Ala Glu Ile Asn Arg
                85                  90                  95

Pro Asp Tyr Leu Asp Phe Ala Glu
            100

<210> SEQ ID NO 6
<211> LENGTH: 97
<212> TYPE: PRT
<213> ORGANISM: Homo sapiens

<400> SEQUENCE: 6

Glu Leu Arg Lys Val Ala His Leu Thr Gly Lys Ser Asn Ser Arg Ser
  1               5                  10                  15

Met Pro Leu Glu Trp Glu Asp Thr Tyr Gly Ile Val Leu Leu Ser Gly
                20                  25                  30

Val Lys Tyr Ser Lys Val Tyr Phe Arg Gly Gln Ser Cys Asn Asn Leu
            35                  40                  45

Pro Leu Ser His Lys Val Tyr Met Arg Asn Ser Lys Tyr Pro Gln Met
```

```
                  50                  55                  60

Trp Ala Arg Ser Ser Tyr Leu Gly Ala Val Phe Asn Leu Thr Ser Ala
 65                  70                  75                  80

Asp His Leu Tyr Val Asn Val Ser Glu Leu Ser Leu Val Asn Phe Glu
                 85                  90                  95

Glu

<210> SEQ ID NO 7
<211> LENGTH: 102
<212> TYPE: PRT
<213> ORGANISM: Homo sapiens

<400> SEQUENCE: 7

Thr Leu Lys Pro Ala Ala His Leu Ile Gly Asp Pro Ser Lys Gln Asn
 1               5                  10                  15

Ser Leu Leu Trp Arg Ala Asn Thr Asp Arg Ala Phe Leu Gln Asp Gly
                20                  25                  30

Phe Tyr Ser Gln Val Val Phe Ser Gly Lys Ala Tyr Ser Pro Lys Ala
             35                  40                  45

Thr Ser Ser Pro Leu Tyr Leu Ala His Glu Val Gln Leu Phe Ser Ser
         50                  55                  60

Gln Tyr Pro Phe Pro Trp Leu His Ser Met Tyr His Gly Ala Ala Phe
 65                  70                  75                  80

Gln Leu Thr Gln Gly Asp Gln Leu Ser Thr His Thr Asp Gly Ile Pro
                 85                  90                  95

His Leu Val Leu Ser Phe
            100

<210> SEQ ID NO 8
<211> LENGTH: 109
<212> TYPE: PRT
<213> ORGANISM: Homo sapiens

<400> SEQUENCE: 8

Glu Ala Gln Pro Phe Ala His Leu Thr Ile Asn Ala Thr Asp Ile Pro
 1               5                  10                  15

Ser Gly Ser His Lys Val Ser Leu Ser Ser Trp Tyr His Asp Arg Gly
                20                  25                  30

Trp Gly Lys Ile Ser Asn Met Tyr Ala Asn Ile Cys Phe Arg His His
             35                  40                  45

Glu Thr Ser Gly Asp Leu Ala Thr Glu Tyr Leu Gln Leu Met Val Tyr
         50                  55                  60

Val Thr Lys Thr Ser Ile Lys Ile Pro Ser Glu Phe His Phe Tyr Ser
 65                  70                  75                  80

Ile Asn Val Gly Gly Phe Phe Lys Leu Arg Ser Gly Glu Glu Ile Ser
                 85                  90                  95

Ile Glu Val Ser Asn Pro Ser Leu Leu Asp Pro Asp Gln
            100                 105

<210> SEQ ID NO 9
<211> LENGTH: 26
<212> TYPE: DNA
<213> ORGANISM: Homo sapiens

<400> SEQUENCE: 9
actgtttctt ctggaccctg aacggc                                        26
```

```
<210> SEQ ID NO 10
<211> LENGTH: 30
<212> TYPE: DNA
<213> ORGANISM: Homo sapiens

<400> SEQUENCE: 10
gacaagcttg ccaccatgga tgactccaca                              30

<210> SEQ ID NO 11
<211> LENGTH: 23
<212> TYPE: DNA
<213> ORGANISM: Homo sapiens

<400> SEQUENCE: 11
actagtcaca gcagtttcaa tgc                                     23

<210> SEQ ID NO 12
<211> LENGTH: 22
<212> TYPE: DNA
<213> ORGANISM: Homo sapiens

<400> SEQUENCE: 12
ctgcagggtc cagaagaaac ag                                      22

<210> SEQ ID NO 13
<211> LENGTH: 24
<212> TYPE: DNA
<213> ORGANISM: Homo sapiens

<400> SEQUENCE: 13
ggagaaggca actccagtca gaac                                    24

<210> SEQ ID NO 14
<211> LENGTH: 24
<212> TYPE: DNA
<213> ORGANISM: Homo sapiens

<400> SEQUENCE: 14
caattcatcc ccaaagacat ggac                                    24

<210> SEQ ID NO 15
<211> LENGTH: 22
<212> TYPE: DNA
<213> ORGANISM: Homo sapiens

<400> SEQUENCE: 15
tcggaacaca acgaaacaag tc                                      22

<210> SEQ ID NO 16
<211> LENGTH: 26
<212> TYPE: DNA
<213> ORGANISM: Homo sapiens

<400> SEQUENCE: 16
cttctccttc acctggaaac tgactg                                  26

<210> SEQ ID NO 17
<211> LENGTH: 19
<212> TYPE: DNA
<213> ORGANISM: Homo sapiens

<400> SEQUENCE: 17
ggcatcgtga tggactccg                                          19
```

-continued

```
<210> SEQ ID NO 18
<211> LENGTH: 19
<212> TYPE: DNA
<213> ORGANISM: Homo sapiens

<400> SEQUENCE: 18
gctggaaggt ggacagcga                                              19

<210> SEQ ID NO 19
<211> LENGTH: 35
<212> TYPE: DNA
<213> ORGANISM: Homo sapiens

<400> SEQUENCE: 19
taagaatgcg gccgcggaat ggatgagtct gcaaa                            35

<210> SEQ ID NO 20
<211> LENGTH: 35
<212> TYPE: DNA
<213> ORGANISM: Homo sapiens

<400> SEQUENCE: 20
taagaatgcg gccgcgggat cacgcactcc agcaa                            35

<210> SEQ ID NO 21
<211> LENGTH: 21
<212> TYPE: DNA
<213> ORGANISM: Homo sapiens

<400> SEQUENCE: 21
gcagtttcac agcgatgtcc t                                           21

<210> SEQ ID NO 22
<211> LENGTH: 21
<212> TYPE: DNA
<213> ORGANISM: Homo sapiens

<400> SEQUENCE: 22
gtctccgttg cgtgaaatct g                                           21

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence:
      Illustrative motif

<400> SEQUENCE: 23

Arg Asn Lys Arg
  1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence:
      Illustrative motif

<400> SEQUENCE: 24

Arg Lys Arg Arg
  1
```

-continued

```
<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence:
      Illustrative motif

<400> SEQUENCE: 25

Arg Pro Arg Arg
  1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence:
      Illustrative motif
<220> FEATURE:
<221> NAME/KEY: MOD_RES
<222> LOCATION: (2)
<223> OTHER INFORMATION: Any amino acid
<220> FEATURE:
<221> NAME/KEY: MOD_RES
<222> LOCATION: (3)
<223> OTHER INFORMATION: Lys or Arg

<400> SEQUENCE: 26

Arg Xaa Xaa Arg
  1

<210> SEQ ID NO 27
<211> LENGTH: 185
<212> TYPE: PRT
<213> ORGANISM: Human
<220> FEATURE:
<221> NAME/KEY: MISC_FEATURE
<222> LOCATION: (46)..(46)
<223> OTHER INFORMATION: Insertion of alanine; splice variant

<400> SEQUENCE: 27

Met Arg Arg Gly Pro Arg Ser Leu Arg Gly Arg Asp Ala Pro Ala Pro
  1               5                  10                  15

Thr Pro Cys Val Pro Ala Glu Cys Phe Asp Leu Leu Val Arg His Cys
                 20                  25                  30

Val Ala Cys Gly Leu Leu Arg Thr Pro Arg Pro Lys Pro Xaa Ala Gly
             35                  40                  45

Ala Ser Ser Pro Ala Pro Arg Thr Ala Leu Gln Pro Gln Glu Ser Val
         50                  55                  60

Gly Ala Gly Ala Gly Glu Ala Ala Leu Pro Leu Pro Gly Leu Leu Phe
 65                  70                  75                  80

Gly Ala Pro Ala Leu Leu Gly Leu Ala Leu Val Leu Ala Leu Val Leu
                 85                  90                  95

Val Gly Leu Val Ser Trp Arg Arg Arg Gln Arg Arg Leu Arg Gly Ala
            100                 105                 110

Ser Ser Ala Glu Ala Pro Asp Gly Asp Lys Asp Ala Pro Glu Pro Leu
        115                 120                 125

Asp Lys Val Ile Ile Leu Ser Pro Gly Ile Ser Asp Ala Thr Ala Pro
    130                 135                 140

Ala Trp Pro Pro Pro Gly Glu Asp Pro Gly Thr Thr Pro Pro Gly His
145                 150                 155                 160

Ser Val Pro Val Pro Ala Thr Glu Leu Gly Ser Thr Glu Leu Val Thr
                165                 170                 175
```

```
Thr Lys Thr Ala Gly Pro Glu Gln Gln
        180                 185

<210> SEQ ID NO 28
<211> LENGTH: 175
<212> TYPE: PRT
<213> ORGANISM: Mouse

<400> SEQUENCE: 28

Met Gly Ala Arg Arg Leu Arg Val Arg Ser Gln Arg Ser Arg Asp Ser
 1               5                  10                  15

Ser Val Pro Thr Gln Cys Asn Gln Thr Glu Cys Phe Asp Pro Leu Val
            20                  25                  30

Arg Asn Cys Val Ser Cys Glu Leu Phe His Thr Pro Asp Thr Gly His
        35                  40                  45

Thr Ser Ser Leu Glu Pro Gly Thr Ala Leu Gln Pro Gln Glu Gly Ser
    50                  55                  60

Ala Leu Arg Pro Asp Val Ala Leu Leu Val Gly Ala Pro Ala Leu Leu
65                  70                  75                  80

Gly Leu Ile Leu Ala Leu Thr Leu Val Gly Leu Val Ser Leu Val Ser
                85                  90                  95

Trp Arg Trp Arg Gln Gln Leu Arg Thr Ala Ser Pro Asp Thr Ser Glu
            100                 105                 110

Gly Val Gln Gln Glu Ser Leu Glu Asn Val Phe Val Pro Ser Ser Glu
        115                 120                 125

Thr Pro His Ala Ser Ala Pro Thr Trp Pro Pro Leu Lys Glu Asp Ala
    130                 135                 140

Asp Ser Ala Leu Pro Arg His Ser Val Pro Val Pro Ala Thr Glu Leu
145                 150                 155                 160

Gly Ser Thr Glu Leu Val Thr Thr Lys Thr Ala Gly Pro Glu Gln
                165                 170                 175
```